US012629420B2

(12) United States Patent
Francis et al.

(10) Patent No.: US 12,629,420 B2
(45) Date of Patent: May 19, 2026

(54) CXCR5 ANTIBODY FORMULATIONS

(71) Applicant: SANOFI, Paris (FR)

(72) Inventors: Donny Francis, Frankfurt am Main (DE); Ahmed Youssef, Frankfurt am Main (DE); Stefaniya Korueva, Frankfurt am Main (DE); Martina Kirsch, Frankfurt am Main (DE)

(73) Assignee: SANOFI, Paris (FR)

( * ) Notice: Subject to any disclaimer, the term of this patent is extended or adjusted under 35 U.S.C. 154(b) by 519 days.

(21) Appl. No.: 17/562,480

(22) Filed: Dec. 27, 2021

(65) Prior Publication Data

US 2022/0111048 A1      Apr. 14, 2022

Related U.S. Application Data

(62) Division of application No. 16/315,533, filed as application No. PCT/EP2017/066803 on Jul. 5, 2017, now Pat. No. 11,207,407.

(60) Provisional application No. 62/358,404, filed on Jul. 5, 2016.

(30) Foreign Application Priority Data

Aug. 30, 2016 (EP) .................................... 16306090

(51) Int. Cl.
| | |
|---|---|
| *A61K 39/395* | (2006.01) |
| *A61K 9/00* | (2006.01) |
| *A61K 9/19* | (2006.01) |
| *A61K 47/12* | (2006.01) |
| *A61K 47/18* | (2017.01) |
| *A61K 47/20* | (2006.01) |
| *A61K 47/26* | (2006.01) |
| *C07K 16/28* | (2006.01) |

(52) U.S. Cl.
CPC ...... *A61K 39/39591* (2013.01); *A61K 9/0019* (2013.01); *A61K 9/19* (2013.01); *A61K 39/3955* (2013.01); *A61K 47/12* (2013.01); *A61K 47/183* (2013.01); *A61K 47/20* (2013.01); *A61K 47/26* (2013.01); *C07K 16/2866* (2013.01); *C07K 2317/24* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 8,647,622 | B2 | 2/2014 | Lee et al. |
| 9,592,289 | B2 | 3/2017 | Schnieders et al. |
| 2010/0285011 | A1 | 11/2010 | Morichika et al. |
| 2014/0004106 | A1 | 1/2014 | Schnieders et al. |

FOREIGN PATENT DOCUMENTS

| | | |
|---|---|---|
| WO | 2009/032661 | 3/2009 |
| WO | 2013/148686 | 3/2013 |

OTHER PUBLICATIONS

Alyautdin R.N. "Pharmacology" edited by Alyautdin R.N.; M.: GEOTAR-MED.—Year: 2004; p. 77.
Daugherty, Ann L. et al. "Formulation and Delivery Issues for Monoclonal Antibody Therapeutics" Current Trends in Monoclonal Antibody Development and Manufacturing (2010), pp. 103-129.
Dunaev S. F. Practical course on general chemistry. 336 p., p. 33 (2005).
K. Holmberg et al.., "Surfactants and polymers in aqueous solutions"— M.: Binom, Year: 2007 ; pp. 272-273.
I.I. Krasnyuk, G.V. Mikhailova. "Pharmaceutical technology: Technology of dosage forms: textbook for students of higher educational institutions" 2nd Edition—M.: Publishing Center "Academy" Year: 2006, pp. 297-299.
M.D. Mashkovsky. "Drugs" 14th edition, vol. 1. Moscow, Year: 2002; pp. 8-9.
The International Search Report (ISR) for PCT/EP2017/066803 dated Sep. 13, 2017, pp. 1-7.
Written Opinion of the International Searching Authority for PCT/EP2017/066803 dated Sep. 13, 2017, pp. 1-7.
Wang, W. et al. "Antibody Structure, Instability, and Formulation" Journal of Pharmaceutical Sciences (2007) vol. 96 (1), pp. 1-26.

*Primary Examiner* — Yunsoo Kim
(74) *Attorney, Agent, or Firm* — McDonnell Boehnen Hulbert & Berghoff LLP

(57) ABSTRACT

High concentration antibody formulations capable of stable long-term storage are disclosed.

13 Claims, 13 Drawing Sheets

Specification includes a Sequence Listing.

CXCR5 ANTIBODY FORMULATIONS

CROSS-REFERENCE TO RELATED APPLICATIONS

This application is a divisional of U.S. patent application Ser. No. 16/315,533, filed Jan. 4, 2019, which is a national stage application under 35 U.S.C. § 371 of International Application No. PCT/EP2017/066803, filed Jul. 5, 2017, which claims the benefit of U.S. Provisional Application No. 62/358,404, filed Jul. 5, 2016, and European Patent Application No. 16306090.8, filed Aug. 30, 2016, the disclosures of each of which are explicitly incorporated by reference herein.

FIELD OF THE INVENTION

The invention relates to antibody formulations with extended storage stability in glass containers.

BACKGROUND

CXCR5, also known as Burkitt lymphoma receptor (BLR1), CD185, MDR15, and MGC117347, is a G protein-coupled receptor that is a member of the CXC chemokine receptor family. CXCR5 affects B cell migration and tissue localization, as is demonstrated by CXCR5 knockout mice that lack peripheral lymph nodes, have fewer Peyer's patches, and have decreased B cell levels. CXCL13, also known as BLC, is a ligand for CXCR5. CXCL13 is a B cell chemoattractant. Anti-CXCR5 binding agents are therapeutically relevant, and they have been formulated into drug products that may be administered to subjects, particularly human subjects, for the treatment of inflammatory diseases.

Pharmaceutical formulations containing an anti-CXCR5 binding agent suitable for intravenous or subcutaneous administration must be highly concentrated (at about 20 mg/mL to about 100-150 mg/mL, and even up to 250 mg/mL or more). However, many problems with such pharmaceutical formulations can occur at high concentrations, including increased viscosity, a pH shift, and a solution color change. In addition, at high binding agent concentrations, the chance for formation of visible and sub-visible particles, binding agent aggregates, and/or binding agent half-molecules is increased. Still further, at high binding agent concentrations, there is an increased chance of interaction between the pharmaceutical formulation and its storage container. Therefore, there remains a need for improved pharmaceutical formulations that avoid these limitations.

SUMMARY OF THE INVENTION

Provided herein are anti-CXCR5 antibody pharmaceutical formulations with increased storage stability in glass storage containers.

In a first aspect, the invention provides an antibody formulation suitable for subcutaneous administration to a patient. The formulation includes about 50 to about 250 mg/mL of an anti-CXCR5 antibody; a citrate buffer; greater than about 0.01% (w/v) surfactant; greater than about 50 mM amino acid; and greater than about 1% sucrose. The pH of the formulation is about pH 6.

In one embodiment of the first aspect, the anti-CXCR5 antibody or a fragment thereof includes: (a) a light chain variable domain comprising the amino acid sequence of SEQ ID NO: 11, and a heavy chain variable domain comprising the amino acid sequence of SEQ ID NO: 12; (b) the amino acid sequences of RSSKSLLHSSGKTYLY (SEQ ID NO: 58), RMSNLAS (SEQ ID NO: 59), MQHLEYPYT (SEQ ID NO: 60), GFSLIDYGVN (SEQ ID NO: 61), VIWGDGTTY (SEQ ID NO: 62), and IVY (SEQ ID NO: 63); (c) a light chain variable domain comprising the amino acid sequence of SEQ ID NO: 13, SEQ ID NO: 14, or SEQ ID NO: 15, and a heavy chain variable domain comprising the amino acid sequence of SEQ ID NO: 16; (d) the amino acid sequences of RSSKSLLHSSGKTYLY (SEQ ID NO: 58), RLSNLAS (SEQ ID NO: 64), MQHLEYPYT (SEQ ID NO: 60), GFSLIDYGVN (SEQ ID NO: 61), VIWGDGTTY (SEQ ID NO: 62), and IVY (SEQ ID NO: 63); (e) the amino acid sequences of RSSKSLLHSSGKTYLY (SEQ ID NO: 58), RLSSNLAS (SEQ ID NO: 65), MQHLEYPYT (SEQ ID NO: 60), GFSLIDYGVN (SEQ ID NO: 61), VIWGDGTTY (SEQ ID NO: 62), and IVY (SEQ ID NO: 63); (f) a variable light chain (VL) comprising the amino acid sequence of SEQ ID NO: 17, SEQ ID NO: 19, or SEQ ID NO: 21, and a variable heavy chain (VH) comprising the amino acid sequence of SEQ ID NO: 23; (g) a variable light chain comprising the amino acid sequence of SEQ ID NO: 30, SEQ ID NO: 31, or SEQ ID NO: 32, and a variable heavy chain comprising the amino acid sequence of SEQ ID NO: 33 or SEQ ID NO: 34; (h) the amino acid sequences of RSSKSLLHSSGKTYLY (SEQ ID NO: 58), RMSNLA (SEQ ID NO: 66), MQHLEYPYT (SEQ ID NO: 60), GFSLIDYGVN (SEQ ID NO: 61), VIWGDGTTY (SEQ ID N: 62), and IVY (SEQ ID NO: 63); (i) the amino acid sequences of RSSKSLLHSSGKTYLY (SEQ ID NO: 58), RLSNLA (SEQ ID NO: 67), MQHLEYPYT (SEQ ID NO: 60), GFSLIDYGVN (SEQ ID NO: 61), VIWGDGTTY (SEQ ID NO: 62), and IVY (SEQ ID NO: 63); (j) the amino acid sequences of RSSKSLLHSSGKTYLY (SEQ ID NO: 58), RLSSLA (SEQ ID NO: 68), MQHLEYPYT (SEQ ID NO: 60), GFSLIDYGVN (SEQ ID NO: 61), VIWGDGTTY (SEQ ID NO: 62), and IVY (SEQ ID NO: 63); (k) a variable light chain comprising the amino acid sequence of SEQ ID NO: 35, and a variable heavy chain comprising the amino acid sequence of SEQ ID NO: 37; (l) a variable light chain comprising the amino acid sequence of SEQ ID NO: 39, SEQ ID NO: 41, or SEQ ID NO: 43, and a variable heavy chain comprising the amino acid sequence of SEQ ID NO: 45 or SEQ ID NO: 47; (m) a variable light chain comprising the amino acid sequence of SEQ ID NO: 55, and a variable heavy chain comprising the amino acid sequence of SEQ ID NO: 56 or SEQ ID NO: 57; or (n) the amino acid sequences of RSSKSLLHSSGKTYLYW (SEQ ID NO: 69), RMSNLA (SEQ ID NO: 66), MQHLEYPYT (SEQ ID NO: 60), GFSLIDYGVN (SEQ ID NO: 61), VIWGDGTTY (SEQ ID NO: 62), and IVY (SEQ ID NO: 63).

In another embodiment of the first aspect, the amino acid is arginine or methionine.

In one embodiment of the first aspect, the surfactant is a polysorbate.

In a second aspect, the invention provides an antibody formulation suitable for subcutaneous administration to a patient. The formulation includes about 100 to about 175 mg/mL of an antibody; about 10 mM citrate buffer; about 0.1% (w/v) surfactant; about 200 mM arginine; and about 4.5 to 9% sucrose. The pH of the formulation is about pH 6.

In one embodiment of the second aspect, the antibody is a fully human anti-CXCR5 antibody.

In another embodiment of the second aspect, the antibody includes a heavy chain having the amino acid sequence of SEQ ID NO: 33 and a light chain having the amino acid sequence of SEQ ID NO: 32.

In a further embodiment of the second aspect, the antibody comprises a single chain Fv.

In another embodiment of the second aspect, the antibody is an isolated antibody or fragment thereof that specifically binds to the extracellular domain of human CXCR5.

In one embodiment of the second aspect, the isolated antibody or fragment thereof comprises the amino acid sequences of RSSKSLLHSSGKTYLY (SEQ ID NO: 58), RLSSLA (SEQ ID NO: 68), MQHLEYPYT (SEQ ID NO: 60), GFSLIDYGVN (SEQ ID NO: 61), VIWGDGTTY (SEQ ID NO: 62), and IVY (SEQ ID NO: 63).

In one embodiment of the second aspect, the surfactant is a polysorbate.

In another embodiment of the second aspect, the polysorbate is polysorbate 20 or polysorbate 80.

In a third aspect, the invention provides an antibody formulation that includes about 175 mg/mL of a humanized IgG4 anti-CXCR5 antibody; about 10 mM citrate buffer; about 1.0 mg/mL polysorbate 80; about 200 mM arginine HCl; and about 45 mg/mL sucrose. The pH of the formulation is about pH 6.

In one embodiment of the third aspect, the humanized IgG4 anti-CXCR5 antibody includes a heavy chain having the amino acid sequence of SEQ ID NO: 33 and a light chain having the amino acid sequence of SEQ ID NO: 32.

In a fourth aspect, the invention provides a container including the antibody formulation according to any of the preceding aspects or embodiments.

In one embodiment of the fourth aspect, the container is a prefilled syringe, a vial, or an autoinjector.

In another embodiment of the fourth aspect, the container includes the antibody formulation according to any of the preceding aspects or embodiments in a lyophilized form.

In a fifth aspect, the invention provides a kit including the container of the fourth aspect and any embodiments thereof, and a label or instructions for the administration and use of the antibody formulation.

In one embodiment of the fifth aspect, administration is by injection.

In a sixth aspect, the invention provides an antibody formulation according to any of the preceding aspects or embodiments for use in a method of diagnosis or treatment of the human or animal body.

In a seventh aspect, the invention provides a method for treating rheumatoid arthritis including administering to a subject in need thereof the antibody formulation according to any of the preceding aspects or embodiments.

In an eighth aspect, the invention provides a lyophilized form of the antibody formulation according to any of the preceding aspects or embodiments.

DETAILED DESCRIPTION

Figures 1, 2, 3:
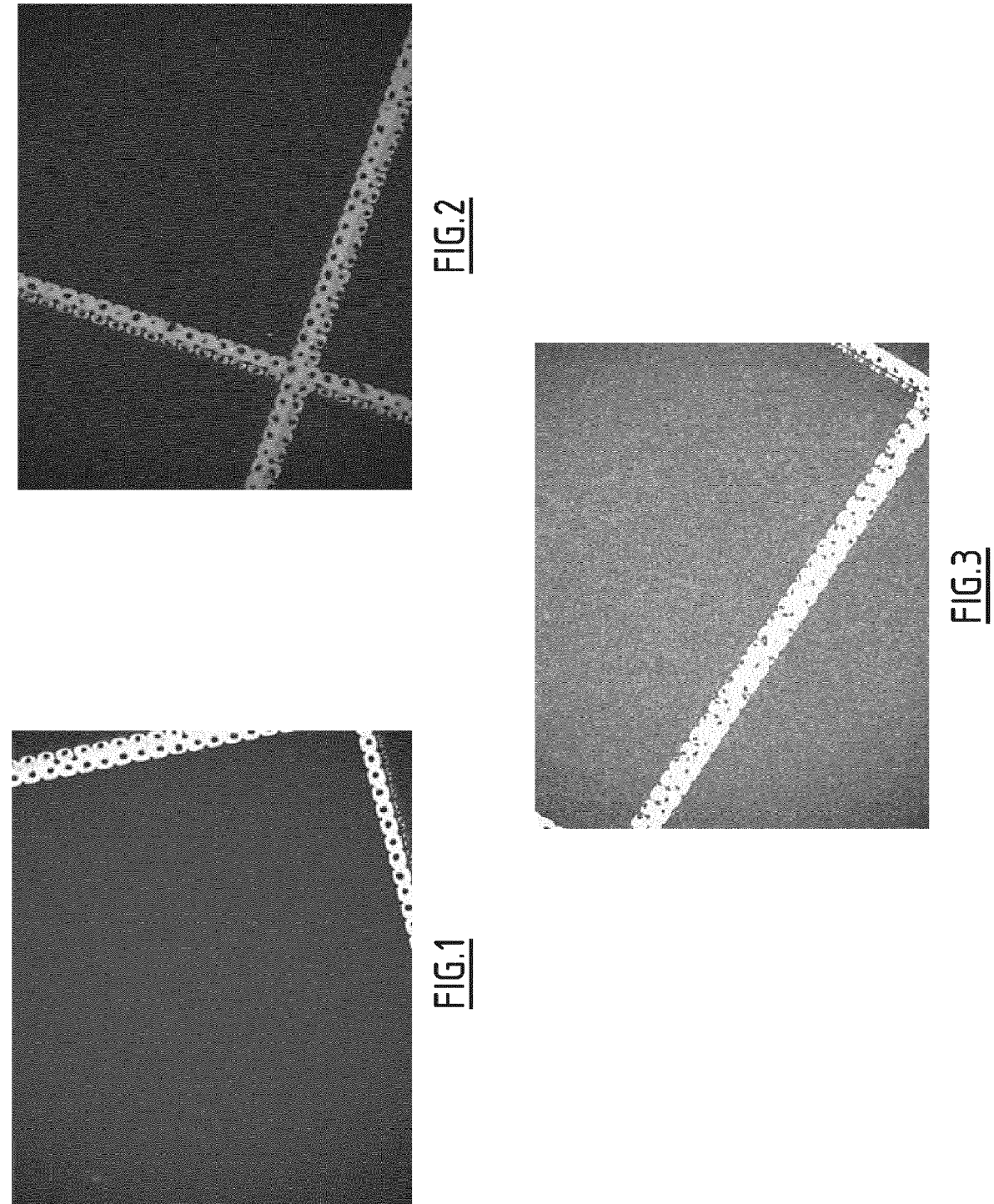
FIG. 1 is a photomicrograph of a cellulose filter after filtration of a first anti-CXCR5 antibody formulation placebo. Magnification is 50×.
FIG. 2 is a photomicrograph of a cellulose filter after filtration of second anti-CXCR5 antibody formulation placebo. Magnification is 50×.
FIG. 3 is a photomicrograph of a cellulose filter after filtration of third anti-CXCR5 antibody formulation placebo. Magnification is 50×.

Unless defined otherwise, all technical and scientific terms used herein have the same meaning as is commonly understood by one of ordinary skill in the art.

It is noted here that as used in this specification and the appended claims, the singular forms "a," "an," and "the" also include plural reference, unless the context clearly dictates otherwise.

The term "about" or "approximately" means within 10%, such as within 5% (or 1% or less) of a given value or range.

The terms "administer" or "administration" refers to the act of injecting or otherwise physically delivering a substance as it exists outside the body (e.g., a formulation of the invention) into a patient, such as by mucosal, intradermal, intravenous, subcutaneous, intramuscular delivery and/or any other method of physical delivery described herein or known in the art. When a disease, or a symptom thereof, is being treated, administration of the substance typically occurs after the onset of the disease or symptoms thereof. When a disease or a symptom thereof, is being prevented, administration of the substance typically occurs before the onset of the disease or symptoms thereof.

In the context of a polypeptide, the term "analog" refers to a polypeptide that possesses a similar or identical function as a CXCR5 polypeptide, a fragment of a CXCR5 polypeptide, a CXCR5 epitope, or an anti-CXCR5 antibody, but does not necessarily comprise a similar or identical amino acid sequence of a CXCR5 polypeptide, a fragment of a CXCR5 polypeptide, a CXCR5 epitope, or an anti-CXCR5 antibody, or possesses a similar or identical structure of a CXCR5 polypeptide, a fragment of a CXCR5 polypeptide, a CXCR5 epitope, or an anti-CXCR5 antibody.

A polypeptide that has a similar amino acid sequence refers to a polypeptide that satisfies at least one of the following: (a) a polypeptide having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of a CXCR5 polypeptide, a fragment of a CXCR5 polypeptide, a CXCR5 epitope, or an anti-CXCR5 antibody described herein; (b) a polypeptide encoded by a nucleotide sequence that hybridizes under stringent conditions to a nucleotide sequence encoding a CXCR5 polypeptide, a fragment of a CXCR5 polypeptide, a CXCR5 epitope, or an anti-CXCR5 antibody (or VH or VL region thereof) described herein of at least 5 amino acid residues, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, or at least 150 amino acid residues (see, e.g., Sambrook et al. (2001) Molecular Cloning: A Laboratory Manual, Cold Spring Harbor Laboratory Press, Cold Spring Harbor, N.Y.; Maniatis et al. (1982) Molecular Cloning: A Laboratory Manual, Cold Spring Harbor Press, Cold Spring Harbor, N.Y.); and (c) a polypeptide encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% identical to the nucleotide sequence encoding a CXCR5 polypeptide, a fragment of a CXCR5 polypeptide, a CXCR5 epitope, or an anti-CXCR5 antibody (or VH or VL region thereof) described herein. A polypeptide with similar structure to a CXCR5 polypeptide, a fragment of a CXCR5 polypeptide, a CXCR5 epitope, or an anti-CXCR5 antibody refers to a polypeptide that has a similar secondary, tertiary or quaternary structure of a CXCR5 polypeptide, a fragment of a CXCR5 polypeptide, a CXCR5 epitope, or a CXCR5 antibody. The structure of a polypeptide can be determined by methods known to those skilled in the art, including but not limited to, X-ray crystallography, nuclear magnetic resonance, and crystallographic electron microscopy.

An "antagonist" or "inhibitor" refers to a molecule capable of inhibiting one or more biological activities of a target molecule. Antagonists can interfere with the binding of a receptor to a ligand and vice versa, by incapacitating or killing cells activated by a ligand, and/or by interfering with receptor or ligand activation (e.g., tyrosine kinase activation) or signal transduction after ligand binding to a receptor. The antagonist can completely block receptor-ligand interactions or can substantially reduce such interactions. All such points of intervention by an antagonist shall be considered equivalent for purposes of the instant invention.

For example, an "antagonist" or "inhibitor" of CXCR5 refers to a molecule capable of inhibiting one or more biological activities, such as signaling, by CXCR5. Thus, included within the scope of the invention are antagonists (e.g., neutralizing antibodies) that bind to CXCR5, CXCL13 or other ligands of CXCR5, or a complex of CXCR5 and a ligand thereof, such as CXCL13; amino acid sequence variants or derivatives of CXCR5 or CXCL13 which antagonize the interaction between CXCR5 and a ligand, such as CXCL13; soluble CXCR5, optionally fused to a heterologous molecule such as an immunoglobulin region (e.g., an immunoadhesin); a complex comprising CXCR5 in association with another receptor or biological molecule; synthetic or native sequence peptides which bind to CXCR5; and so on.

The terms "antibody," "immunoglobulin," or "Ig" may be used interchangeably herein. The term antibody includes, but is not limited to, synthetic antibodies, monoclonal antibodies, recombinantly produced antibodies, multispecific antibodies (including bi-specific antibodies), human antibodies, humanized antibodies, chimeric antibodies, intrabodies, single-chain Fvs (scFv) (e.g., including monospecific, bispecific, etc.), camelized antibodies, Fab fragments, F(ab') fragments, disulfide-linked Fvs (sdFv), anti-idiotypic (anti-Id) antibodies, and epitope-binding fragments of any of the above. In particular, antibodies include immunoglobulin molecules and immunologically active portions of immunoglobulin molecules, i.e., antigen binding domains or molecules that contain an antigen-binding site that specifically binds to a CXCR5 antigen (e.g., one or more complementarity determining regions (CDRs) of an anti-CXCR5 antibody). The anti-CXCR5 antibodies can be of any type (e.g., IgG, IgE, IgM, IgD, IgA, and IgY), any class (e.g., IgG1, IgG2, IgG3, IgG4, IgA1, and IgA2), or any subclass (e.g., IgG2a and IgG2b) of immunoglobulin molecule. In some embodiments, the anti-CXCR5 antibodies are humanized, such as humanized monoclonal anti-CXCR5 antibodies. In certain embodiments, the anti-CXCR5 antibodies are IgG antibodies, and in particular, humanized IgG4 antibodies.

As used herein, the term "anti-CXCR5 antibody" means an antibody or polypeptide derived therefrom (a derivative) that binds specifically to human CXCR5 as defined herein, including, but not limited to, molecules that inhibit or substantially reduce the binding of CXCR5 to its ligands and/or inhibit CXCR5 activity. For example, a contemplated anti-CXCR5 antibody includes an isolated antibody or fragment thereof that specifically binds to the extracellular domain of human CXCR5, such as those disclosed in U.S. Pat. No. 8,647,622, incorporated herein by reference for all purposes. In particular, contemplated anti-CXCR5 antibodies of the present disclosure have a variable light chain including the amino acid sequence of SEQ ID NO: 32 and a variable heavy chain including the amino acid sequence of SEQ ID NO: 33 of U.S. Pat. No. 8,647,622. In another embodiment, an isolated antibody or fragment thereof that specifically binds to the extracellular domain of human CXCR5 includes the amino acid sequences of RSSKSLLHSSGKTYLY (SEQ ID NO: 58), RLSSLA (SEQ ID NO: 68), MQHLEYPYT (SEQ ID NO: 60), GFSLIDYGVN (SEQ ID NO: 61), VIWGDGTTY (SEQ ID NO: 62), and IVY (SEQ ID NO: 63) of U.S. Pat. No. 8,647,622.

The term "B cell activity" means higher than normal B cell levels, which can be local, or evidence of a biological manifestation or function of a B cell, such as antibody expression, Bruton's tyrosine kinase presence or activity, expression or presence of CD19, expression or presence of B cell activating factor, and so on.

The term "binding agent" means any molecule, such as an antibody, a siRNA, a nucleic acid, an aptamer, a protein, or a small molecule organic compound, that binds or specifically binds to CXCR5, or a variant or a fragment thereof.

The term "by-product" includes undesired products, which detract or diminish the proportion of therapeutic/prophylactic binding agent, such as an antibody, in a given formulation. For example, typical by-products include aggregates of the antibody, fragments of the antibody, e.g. produced by degradation of the antibody by deamidation or hydrolysis, or mixtures thereof. Typically, aggregates are complexes that have a molecular weight greater than the monomer antibody. Antibody degradation products may include, for example, fragments of the antibody, for example, brought about by deamidation or hydrolysis. Typically, degradation products are complexes that have a molecular weight less than the monomer antibody. In the case of an IgG antibody, such degradation products are less than about 150 kD.

The terms "composition" and "formulation" are intended to encompass a product containing the specified ingredients (e.g., an anti-CXCR5 antibody) in, optionally, the specified amounts, as well as any product that results, directly or indirectly, from the combination of the specified ingredients in, optionally, the specified amounts.

The terms "constant region" and "constant domain" refer to a carboxy terminal portion of the light and heavy chain that is not directly involved in binding of the antibody to antigen but exhibits various effector functions, such as interaction with the Fc receptor. The terms refer to the portion of an immunoglobulin molecule having a more conserved amino acid sequence relative to the other portion of the immunoglobulin, the variable domain, which contains the antigen-binding site. The constant domain contains the CH1, CH2, and CH3 domains of the heavy chain and the CHL domain of the light chain.

The term "CXCR5" relates to the naturally occurring, known molecule found on lymphocytes, particularly B cells, and particularly naïve B cells; to such a molecule isolated from such cells; to such a molecule manufactured recombinantly using known materials and means, and using a nucleic acid encoding a CXCR5; as well as to portions of CXCR5, such as the extracellular (EC) domain, that retain the characteristics and properties relevant to the practice of the instant invention, such as CXCL13 binding. A soluble CXCR5 molecule can consist essentially of the EC domain of CXCR5, which includes, generally, about the first sixty amino acids of the molecule, that is, the amino terminal portion of CXCR5.

CXCR5 is a non-promiscuous receptor. CXCL13 is a ligand of CXCR5 and is expressed constitutively on stromal cells, such as follicular dendritic cells, and in lymphoid tissues. CXCL13 specifically attracts B cells and a small subset of T cells called B helper follicular T cells, TFH. This may not be unexpected given the many interactions between T cell and B cell populations in the immune system. Moreover, activated T cells induce or upregulate CXCR5 expression. Infiltration of lymphocytes into tertiary, ectopic germinal centers (GCs) has been found to correlate well with increased disease severity and tolerance breakdown in certain disorders that present with such atypical lymph node-like structures. Using in vivo murine models, such as CXCR5−/− and CXCL13−/− mice, the absence of either the receptor or the ligand results in an altered GC fine architecture due to altered T and B cell localization, and possibly interaction. These mice are also protected against developing severe collagen-induced arthritis (CIA). As CXCR5 is selectively expressed on mature B cells, which are linked to the pathogenesis of RA, blocking this receptor will modulate the arthritogenic response in affected individuals. Rheumatoid arthritis treatment with biologics (i.e., anti-TNF-α and anti-CD20 antibodies, Rituximab) has shown to be clinically effective; in particular, patients on B cell-directed therapy have shown long-lasting improvements in clinical signs and symptoms. Selective targeting of CXCR5, which is only expressed on mature B cells and B helper T cells, will not affect B cell development or immunocompromise the patient. Unlike Rituximab, the instant anti-CXCR5 antibody is a neutralizing antibody that does not mediate cell cytotoxicity.

A "CXCR5 disease" is a malady, disorder, disease, condition, abnormality, and so on, that is characterized by or caused by overexpression or increased levels of CXCL13 or other CXCR5 ligand, increased levels of B cells, increased levels of B cell activity, increased levels of CXCR5, or improper metabolism and activity of CXCR5.

The term "epitope" refers to a localized region on the surface of an antigen, such as a CXCR5 polypeptide, or CXCR5 polypeptide fragment, that is capable of being bound to one or more antigen binding regions of a binding agent, such as an antibody, and that has antigenic or immunogenic activity in an animal, such as a mammal, for example, a human, that is capable of eliciting an immune response. An epitope having immunogenic activity is a portion of a polypeptide that elicits an antibody response in an animal. An epitope having antigenic activity is a portion of a polypeptide to which an antibody specifically binds, as determined by any method well known in the art, for example, such as an immunoassay. Antigenic epitopes need not necessarily be immunogenic. Epitopes usually consist of chemically active surface groupings of molecules, such as amino acids or sugar side chains, and have specific three-dimensional structural characteristics, as well as specific charge characteristics. A region of a polypeptide contributing to an epitope may be contiguous amino acids of the polypeptide or the epitope may come together from two or more non-contiguous regions of the polypeptide. The epitope may or may not be a three-dimensional surface feature of the antigen. Anti-CXCR5 antibodies may specifically bind to an epitope of the monomeric (denatured) form of CXCR5, an epitope of the trimeric (native) form of CXCR5, or both the monomeric (denatured) form and the trimeric (native) form of CXCR5.

The term "excipients" refers to inert substances that are commonly used as a diluent, vehicle, preservative, binder, stabilizing agent, etc. for drugs and includes, but is not limited to, proteins (e.g., serum albumin, etc.), amino acids (e.g., aspartic acid, glutamic acid, lysine, arginine, glycine, histidine, etc.), fatty acids and phospholipids (e.g., alkyl sulfonates, caprylate, etc.), surfactants (e.g., SDS, polysorbate, nonionic surfactant, etc.), saccharides (e.g., sucrose, maltose, trehalose, etc.), and polyols (e.g., mannitol, sorbitol, etc.). See, also, Remington's Pharmaceutical Sciences (1990) Mack Publishing Co., Easton, Pa., which is hereby incorporated by reference in its entirety for all purposes.

In the context of a peptide or polypeptide, the term "fragment" refers to a peptide or polypeptide that comprises less than the full-length amino acid sequence. Such a fragment may arise, for example, from a truncation at the amino terminus, a truncation at the carboxy terminus, and/or an internal deletion of a residue(s) from the amino acid sequence. Fragments can result, for example, from alternative RNA splicing or from in vivo protease activity. In certain embodiments, hCXCR5 fragments include polypeptides comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least contiguous 100 amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of a CXCR5 polypeptide or an antibody that specifically binds to a CXCR5 polypeptide. In a specific embodiment, a fragment of a CXCR5 polypeptide or an antibody that specifically binds to a CXCR5 antigen retains at least 1, at least 2, or at least 3 functions of the polypeptide or antibody.

The terms "fully human antibody" or "human antibody" are used interchangeably herein and refer to an antibody that comprises a human variable region and, possibly a human constant region. In specific embodiments, the terms refer to an antibody that comprises a variable region and constant region of human origin. In a specific embodiment, the antibodies are fully human antibodies. The term "fully human antibody" includes antibodies having variable and constant regions corresponding to human germline immunoglobulin sequences as described by Kabat et al. (See Kabat et al. (1991) Sequences of Proteins of Immunological Interest, Fifth Edition, U.S. Department of Health and Human Services, NIH Publication No. 91-3242). Methods of producing fully human antibodies are known in the art.

The phrase "recombinant human antibody" includes human antibodies that are prepared, expressed, created, or isolated by recombinant means, such as antibodies expressed using a recombinant expression vector transfected into a host cell, antibodies isolated from a recombinant, combinatorial human antibody library, antibodies isolated from an animal (e.g., a mouse or cow) that is transgenic and/or transchromosomal for human immunoglobulin genes (see, e.g., Taylor, L. D. et al. (1992) Nucl. Acids Res. 20:6287-6295) or antibodies prepared, expressed, created, or isolated by any other means that involves splicing of human immunoglobulin gene sequences to other DNA sequences. Such recombinant human antibodies can have variable and constant regions derived from human germline immunoglobulin sequences (See Kabat et al., 1991). In certain embodiments, however, such recombinant human antibodies are subjected to in vitro mutagenesis (or, when an animal transgenic for human Ig sequences is used, in vivo somatic mutagenesis), and thus, the amino acid sequences of the VH and VL regions of the recombinant antibodies are sequences that while derived from and related to human germline VH and VL sequences, may not naturally exist within the human antibody germline repertoire in vivo.

An "IgG4 binding agent" or a "binding agent comprising at least a portion of an IgG4 Fc region" both refer to binding agents described herein that include at least a fragment of IgG4 Fc. In certain embodiments, the fragment comprises 10, 20, 30, 40, 50, 100, 110, 120, 130, 140, 150, 160, 170, 180, 190, 200, 210 or 220 amino acids of the IgG4 Fc region. In other embodiments, the fragment includes 10-50, 50-100, 100-150, or 150-200 amino acids of the IgG4 Fc region. In other embodiments, the portion of the IgG4 Fc region can have a certain homology to the IgG4 Fc region. For example, the IgG4 binding agent can include a portion of a protein with greater than 50, 60, 70, 80, 90, 93, 95, 96, 97, 98, 99, or 100% homology to the IgG4 Fc region. Exemplary Fc regions of IgG4 are described throughout the specification.

The term "heavy chain", when used in reference to an antibody, refers to five distinct types, called alpha ($\alpha$), delta ($\Delta$), epsilon ($\varepsilon$), gamma ($\gamma$), and mu ($\mu$), based on the amino acid sequence of the heavy chain constant domain. These distinct types of heavy chains are well known in the art and give rise to five classes of antibodies, IgA, IgD, IgE, IgG, and IgM, respectively, including four subclasses of IgG, namely IgG1, IgG1, IgG3, and IgG4. In some embodiments, the heavy chain is a human heavy chain.

"Humanized" forms of non-human (e.g., murine) antibodies are chimeric immunoglobulins, immunoglobulin chains or fragments thereof (such as, Fv, Fab, Fab', F(ab')2 or other target-binding subsequences of antibodies) that contain sequences derived from non-human immunoglobulin, as compared to a human antibody. In general, the humanized antibody will comprise substantially all of one, and typically two, variable domains, in which all or substantially all of the CDR regions correspond to those of a non-human immunoglobulin and all or substantially all of the FR regions are those of a human immunoglobulin template sequence. The humanized antibody may also comprise at least a portion of an immunoglobulin constant region (Fc), typically that of the human immunoglobulin template chosen. In general, the goal is to have an antibody molecule that is minimally immunogenic in a human. Thus, it is possible that one or more amino acids in one or more CDRs also can be changed to one that is less immunogenic to a human host, without substantially minimizing the specific binding function of the one or more CDRs to CXCR5 or to CXCL13. Alternatively, the FR can be non-human but those amino acids most immunogenic are replaced with those less immunogenic. Nevertheless, CDR grafting is not the only way to obtain a humanized antibody. For example, modifying just the CDR regions may be insufficient as it is not uncommon for framework residues to have a role in determining the three-dimensional structure of the CDR loops and the overall affinity of the antibody for its ligand. Hence, any means can be practiced so that the non-human parent antibody molecule is modified to be one that is less immunogenic to a human, and global sequence identity with a human antibody is not always a necessity. So, humanization also can be achieved, for example, by the mere substitution of just a few residues, particularly those which are exposed on the antibody molecule and not buried within the molecule, and hence, not readily accessible to the host immune system. Such a method is taught herein with respect to substituting "mobile" or "flexible" residues on the antibody molecule, the goal being to reduce or dampen the immunogenicity of the resultant molecule without comprising the specificity of the antibody for its epitope or determinant. See, for example, Studnicka et al., Prot Eng 7(6)805-814, 1994; Lazar et al., Mol Immunol. 2007 March; 44(8):1986-98 (2007); Sims et al., J Immunol 151:2296 (1993); Chothia et al., J Mol Biol 196:901 (1987); Carter et al., Proc Natl Acad Sci USA 89:4285 (1992); Presta et al., J Immunol 151:2623 (1993), WO 2006/042333, and U.S. Pat. No. 5,869,619.

An "isolated" or "purified" binding agent, such as an antibody, is substantially free of cellular material or other contaminating proteins from the cell or tissue source from which the binding agent is derived, or substantially free of chemical precursors or other chemicals when chemically synthesized. For example, the language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, or 5% (by dry weight) of heterologous protein (also referred to herein as a "contaminating protein"). When the antibody is recombinantly produced, it is also desirable to be substantially free of culture medium, i.e., culture medium represents less than about 20%, 10%, or 5% of the volume of the protein preparation. When the antibody is produced by chemical synthesis, in some embodiments, it is substantially free of chemical precursors or other chemicals, i.e., it is separated from chemical precursors or other chemicals that are involved in the synthesis of the protein. Accordingly, such preparations of the antibody have less than about 30%, 20%, 10%, or 5% (by dry weight) of chemical precursors or compounds other than the antibody of interest. In some embodiments, anti-CXCR5 antibodies are isolated or purified.

The term "human CXCR5," "hCXCR5" or "hCXCR5 polypeptide" and similar terms refer to the polypeptides ("polypeptides," "peptides" and "proteins" are used interchangeably herein) disclosed in U.S. Pat. No. 8,647,622, and synthesized or isolated from a suitable cell source, and related polypeptides, including SNP variants thereof. Related polypeptides include allelic variants (e.g., SNP variants); splice variants; fragments; derivatives; substitution, deletion, and insertion variants; fusion polypeptides; and interspecies homologs, in some embodiments, which retain CXCR5 activity and/or are sufficient to generate an anti-CXCR5 immune response. Also encompassed are soluble forms of CXCR5 that are sufficient to generate an anti-CXCR5 immunological response. As those skilled in the art will appreciate, an anti-CXCR5 binding agent, such as an antibody, can bind to a CXCR5 polypeptide, polypeptide fragment, antigen, and/or epitope, as an epitope is part of the larger antigen, which is part of the larger polypeptide fragment, which, in turn, is part of the larger polypeptide.

The term "Kabat numbering" and like terms, are recognized in the art and refer to a system of numbering amino acid residues that are more variable (i.e., hypervariable) than other amino acid residues in the heavy and light chain variable regions of an antibody, or an antigen binding portion thereof. (See Kabat et al. (1971) Ann. NY Acad. Sci. 190:382-391 and Kabat et al. (1991)).

The term "light chain" when used in reference to an antibody refers to two distinct types, called kappa (κ) of lambda (λ) based on the amino acid sequence of the constant domains. Light chain amino acid sequences are well known in the art. In some embodiments, the light chain is a human light chain.

The terms "manage," "managing," and "management" refer to the beneficial effects that a subject derives from a therapy (e.g., a prophylactic or therapeutic agent), which does not result in a cure of the infection. In certain embodiments, a subject is administered one or more therapies (e.g., prophylactic or therapeutic agents, such as a formulation of the invention) to "manage" a CXCR5-mediated disease (e.g., rheumatoid arthritis) or one or more symptoms thereof to prevent the progression or worsening of the disease.

The term "monoclonal antibody" refers to an antibody obtained from a population of homogenous or substantially homogeneous antibodies, and each monoclonal antibody will typically recognize a single epitope on the antigen. In some embodiments, a "monoclonal antibody" is an antibody produced by a single hybridoma or other cell. The term "monoclonal" is not limited to any particular method for making the antibody. For example, monoclonal antibodies may be made by the hybridoma method as described in Kohler et al.; Nature, 256:495 (1975) or may be isolated from phage libraries. Other methods for the preparation of clonal cell lines and of monoclonal antibodies expressed thereby are well known in the art (see, for example, Chapter 11 in: Short Protocols in Molecular Biology, (2002) 5th Ed.; Ausubel et al., eds., John Wiley and Sons, New York).

The term "pharmaceutically acceptable" means being approved by a regulatory agency of the Federal or a state government, or listed in the U.S. Pharmacopeia, European Pharmacopeia, or other generally recognized Pharmacopeia for use in animals, and more particularly, in humans.

By "pharmaceutically acceptable excipient" is meant any inert substance that is combined with an active molecule, such as a monoclonal antibody, for preparing an agreeable or convenient dosage form. The "pharmaceutically acceptable excipient" is an excipient that is non-toxic to recipients at the dosages and concentrations employed and is compatible with other ingredients of the formulation including the monoclonal antibody.

The terms "prevent," "preventing," and "prevention" refer to the total or partial inhibition of the development, recurrence, onset or spread of a CXCR5-mediated disease and/or symptom related thereto, resulting from the administration of a therapy or combination of therapies provided herein (e.g., a combination of prophylactic or therapeutic agents, such as a formulation of the invention).

The term "prophylactic agent" refers to any agent that can totally or partially inhibit the development, recurrence, onset, or spread of a CXCR5-mediated disease and/or symptom related thereto in a subject. In certain embodiments, the term "prophylactic agent" refers to a formulation of the invention. In certain other embodiments, the term "prophylactic agent" refers to an agent other than a formulation of the invention. In some embodiments, a prophylactic agent is an agent that is known to be useful to, or has been, or is currently being used to prevent a CXCR5-mediated disease and/or a symptom related thereto, or impede the onset, development, progression and/or severity of or CXCR5-mediated disease and/or a symptom related thereto. In specific embodiments, the prophylactic agent is a fully human antibody, such as a fully human monoclonal antibody, or a humanized anti-CXCR5 antibody, such as a humanized anti-CXCR5 monoclonal antibody.

The term "CXCR5 antigen" refers to that portion of a CXCR5 polypeptide to which a binding agent, such as an antibody, specifically binds. A CXCR5 antigen also refers to an analog or derivative of a CXCR5 polypeptide or fragment thereof to which a binding agent, such as an antibody, specifically binds. A region of a CXCR5 polypeptide contributing to an epitope may be contiguous amino acids of the polypeptide, or the epitope may come together from two or more non-contiguous regions of the polypeptide. The epitope may or may not be a three-dimensional surface feature of the antigen. A localized region on the surface of a CXCR5 antigen that is capable of eliciting an immune response is a CXCR5 epitope. The epitope may or may not be a three-dimensional surface feature of the antigen.

The terms "CXCR5-mediated disease" and "CXCR5-mediated disorder" are used interchangeably and refer to any disease that is completely or partially caused by or is the result of CXCR5. In certain embodiments, CXCR5 is aberrantly (e.g., highly) expressed on the surface of a cell. In some embodiments, CXCR5 may be aberrantly upregulated on a particular cell type. In other embodiments, normal, aberrant, or excessive cell signaling is caused by binding of CXCR5 to a CXCR5 ligand. In certain embodiments, the CXCR5 ligand is CXCL13. In certain embodiments, the CXCR5-mediated disease is rheumatoid arthritis (RA).

The term "saccharide" refers to a class of molecules that are derivatives of polyhydric alcohols. Saccharides are commonly referred to as carbohydrates and may contain different amounts of sugar (saccharide) units, e.g., monosaccharides, disaccharides, and polysaccharides.

The terms "specifically binds" or "specifically binding" mean specifically binding to an antigen or a fragment thereof and not specifically binding to other antigens. For example, an antibody that specifically binds to an antigen may bind to other peptides or polypeptides with lower affinity, as determined by, e.g., radioimmunoassays (RIA), enzyme-linked immunosorbent assays (ELISA), BIACORE®, or other assays known in the art. Antibodies or variants or fragments thereof that specifically bind to an antigen may be cross-reactive with related antigens. In some embodiments, antibodies or variants or fragments thereof that specifically bind to an antigen do not cross-react with other antigens. An antibody or a variant or a fragment thereof that specifically binds to a CXCR5 antigen can be identified, for example, by immunoassays, BIACORE®, or other techniques known to those of skill in the art. Typically, a specific or selective reaction will be at least twice background signal or noise, and more typically more than 10 times background. See e.g., Paul, ed., 1989, Fundamental Immunology Second Edition, Raven Press, New York at pages 332-336, for a discussion regarding antibody specificity.

A "stable" or "stabilized" formulation is one in which the binding agent, such as an antibody, therein essentially retains its physical stability, identity, integrity, and/or chemical stability, identity, integrity, and/or biological activity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10:29-90 (1993), for example. Stability can be measured at a selected temperature and other storage conditions for a selected time period. The stability may be determined by at least one of the methods selected from the group consisting of visual inspection, SDS-PAGE, IEF, HPSEC, RFFIT, and kappa/lambda ELISA. For example, an antibody "retains its physical stability" in a pharmaceutical formulation, if it shows no signs of aggregation, precipitation, and/or denaturation upon visual examination of color and/or clarity, or as measured by UV light scattering, SDS-PAGE, or by (high-pressure) size exclusion chromatography (HPSEC). In some embodiments, when using the formulations of the invention, 5% or less, typically 4% or less, typically 3% or less, more typically 2% or less, and particularly 1% or less of the antibodies forms aggregates, as measured by HPSEC or any other suitable method for measuring aggregation formation. For example, an antibody is considered stable in a particular formulation if the antibody monomer has a purity of about 90%, typically about 95%, in particular about 98% after a certain predetermined period of time under certain storage conditions in a particular formulation. Chemical stability can be assessed by detecting and quantifying chemically altered forms of the protein. Chemical alteration may involve size modification (e.g., clipping), which can be evaluated using (HP)SEC, SDS-PAGE, and/or matrix-assisted laser desorption ionization/time-of-flight mass spectrometry (MALDI/TOF MS), for example. Other types of chemical alteration include charge alteration (e.g., occurring as a result of deamidation), which can be evaluated by ion-exchange chromatography, for example. An antibody "retains its biological activity" in a pharmaceutical formulation at a given time, if the biological activity of the antibody at a given time is at least about 90% (within the errors of the assay) of the biological activity exhibited at the time the pharmaceutical formulation was prepared, as determined in an antigen binding assay or virus neutralizing assay, for example.

In one particular embodiment, an antibody formulation can be "stable against Stardust particle formation," which refers to an antibody formulation that does not form Stardust particles when stored in a glass container under accelerated conditions for a period of 6 months.

The terms "subject" and "patient" can be used interchangeably. As used herein, a subject is typically a mammal, such as a non-primate (e.g., cows, pigs, horses, cats, dogs, rats, etc.) or a primate (e.g., monkey and human), and in some embodiments a human. In one embodiment, the subject is a mammal, such as a human, having a CXCR5-mediated disease. In another embodiment, the subject is a mammal, such as a human, at risk of developing a CXCR5-mediated disease.

The term "therapeutically effective amount" refers to the amount of a therapy (e.g., a formulation of the invention) that is sufficient to reduce and/or ameliorate the severity and/or duration of a given disease and/or a symptom related thereto. This term also encompasses an amount necessary for the reduction or amelioration of the advancement or progression of a given disease, reduction or amelioration of the recurrence, development or onset of a given disease, and/or to improve or enhance the prophylactic or therapeutic effect(s) of another therapy (e.g., a therapy other than a formulation of the invention). In some embodiments, the therapeutically effective amount of an antibody of the invention is from about 0.1 mg/kg (mg of antibody per kg weight of the subject) to about 100 mg/kg. In certain embodiments, a therapeutically effective amount of an antibody provided therein is about 0.1 mg/kg, about 0.5 mg/kg, about 1 mg/kg, 3 mg/kg, 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, or about 100 mg/kg (or a range therein). In some embodiments, "therapeutically effective amount," as used herein, also refers to the amount of an antibody of the invention to achieve a specified result (e.g., inhibition of a CXCR5 biological activity of a cell, such as binding to CXCL13).

The term "therapeutic agent" refers to any agent that can be used in the treatment, management or amelioration of a CXCR5-mediated disease and/or a symptom related thereto. In certain embodiments, the term "therapeutic agent" refers to a formulation of the invention. In certain other embodiments, the term "therapeutic agent" refers to an agent other than a formulation of the invention. In some embodiments, a therapeutic agent is an agent that is known to be useful for, or has been, or is currently being used for the treatment, management or amelioration of a CXCR5-mediated disease or one or more symptoms related thereto.

The term "therapy" refers to any protocol, method, and/or agent that can be used in the prevention, management, treatment, and/or amelioration of a disease (e.g., IBD or GVHD) or CXCR5-mediated disease (e.g., rheumatoid arthritis). In certain embodiments, the terms "therapies" and "therapy" refer to a biological therapy, supportive therapy, and/or other therapies useful in the prevention, management, treatment, and/or amelioration of a or CXCR5-mediated disease known to one of skill in the art, such as medical personnel.

The terms "treat," "treatment," and "treating" refer to the reduction or amelioration of the progression, severity, and/or duration of a CXCR5-mediated disease (e.g., rheumatoid arthritis) resulting from the administration of one or more therapies (including, but not limited to, the administration of one or more prophylactic or therapeutic agents, such as a formulation of the invention). In specific embodiments for CXCR5, such terms refer to the reduction or inhibition of the binding of CXCR5 to CXCL13, and/or the inhibition or reduction of one or more symptoms associated with a CXCR5-mediated disease, such as rheumatoid arthritis.

The terms "variable region" or "variable domain" refer to a portion of the light and heavy chains, typically about the amino-terminal 120 to 130 amino acids in the heavy chain and about 100 to 110 amino acids in the light chain, which differ extensively in sequence among antibodies and are used in the binding and specificity of each particular antibody for its particular antigen. The variability in sequence is concentrated in those regions called complementarity determining regions (CDRs), while the more highly conserved regions in the variable domain are called framework regions (FR). The CDRs of the light and heavy chains are primarily responsible for the interaction of the antibody with antigen. Numbering of amino acid positions is according to the EU Index, as in Kabat et al. (1991) Sequences of proteins of immunological interest. (U.S. Department of Health and Human Services, Washington, D.C.) 5th ed. ("Kabat et al."). In some embodiments, the variable region is a human variable region.

As used herein, the terms "Stardust" and "Stardust particle" can be used interchangeably to refer to particles occurring in glass containers in association with the presence of an antibody formulation within the container.
B. Formulations Formulations of the present disclosure can be found in the form of liquids and lyophilized powders that comprise an anti-CXCR5 binding agent. Further, such formulations may include buffering agents, surfactants, tonicity agents, amino acids, and other excipients.

Binding Agents

In some embodiments of the invention, the anti-CXCR5 antibody is a humanized or a fully human antibody. Examples of humanized and fully human antibody isotypes include IgA, IgD, IgE, IgG, and IgM. In some embodiments, the anti-CXCR5 antibody is an IgG antibody. There are four forms of IgG. In some embodiments, the anti-CXCR5 antibody is an IgG4 antibody. In some embodiments of the invention, the anti-CXCR5 antibody is a humanized IgG4 antibody.

Certain embodiments of formulations of the invention also include variants of anti-CXCR5 binding agents, such as antibodies. Variants of anti-CXCR5 antibodies may have similar physicochemical properties based on their high similarity, and therefore are also included within the scope of the invention. Variants are defined as antibodies with an amino acid sequence that is at least 95%, at least 97%, for instance at least 98% or 99% homologous to an anti-CXCR5 antibody, and capable of competing for binding to a CXCR5 polypeptide, a CXCR5 polypeptide fragment, or a CXCR5 epitope. In some embodiments, the variants will ameliorate, neutralize, or otherwise inhibit CXCR5 biological activity (e.g., the binding of CXCL13 to CXCR5). Determining competition for binding to the target can be done by routine methods known to the skilled person in the art. In some embodiments, the variants are human antibodies, and, in some embodiments, are IgG4 molecules. In some embodiments, a variant is at least 95%, 96%, 97%, 98%, or 99% identical in amino acid sequence with a contemplated antibody disclosed herein. The term "variant" refers to an antibody that comprises an amino acid sequence that is altered by one or more amino acids compared to the amino acid sequences of the anti-CXCR5 antibody. The variant may have conservative sequence modifications, including amino acid substitutions, modifications, additions, and/or deletions.

Examples of modifications include, but are not limited to, glycosylation, acetylation, pegylation, phosphorylation, amidation, derivatization by known protecting/blocking groups, proteolytic cleavage, and linkage to a cellular ligand or other protein. Amino acid modifications can be introduced by standard techniques known in the art, such as site-directed mutagenesis, molecular cloning, oligonucleotide-directed mutagenesis, and random PCR-mediated mutagenesis in the nucleic acid encoding the antibodies. Conservative amino acid substitutions include the ones in which the amino acid residue is replaced with an amino acid residue having similar structural or chemical properties. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine, tryptophan), nonpolar side chains (e.g., glycine, alanine, valine, leucine, isoleucine, proline, phenylalanine, methionine), beta-branched side chains (e.g., threonine, valine, isoleucine), and aromatic side chains (e.g., tyrosine, phenylalanine, tryptophan). It will be clear to the skilled artisan that classifications of amino acid residue families other than the one used above can also be employed. Furthermore, a variant may have non-conservative amino acid substitutions, e.g., replacement of an amino acid with an amino acid residue having different structural or chemical properties. Similar minor variations may also include amino acid deletions or insertions, or both. Guidance in determining which amino acid residues may be substituted, modified, inserted, or deleted without abolishing immunological activity may be found using computer programs well known in the art. Computer algorithms, such as, inter alia, Gap or Bestfit, which are known to a person skilled in the art, can be used to align optimally amino acid sequences to be compared and to define similar or identical amino acid residues. Variants may have the same or different, either higher or lower, binding affinities compared to an anti-CXCR5 antibody, but are still capable of specifically binding to CXCR5, and may have the same, higher or lower, biological activity as the anti-CXCR5 antibody.

Embodiments of the invention also include antigen-binding fragments of the anti-CXCR5 binding agents, such as antibodies. The term "antigen-binding domain," "antigen-binding region," "antigen-binding fragment," and similar terms refer to that portion of an antibody which comprises the amino acid residues that interact with an antigen and confer on the binding agent its specificity and affinity for the antigen (e.g., the complementary determining regions (CDR)). The antigen-binding region can be derived from any animal species, such as rodents (e.g., rabbit, rat or hamster) and humans. In some embodiments, the antigen-binding region will be of human origin. Non-limiting examples of antigen-binding fragments include: Fab fragments, F(ab')2 fragments, Fd fragments, Fv fragments, single chain Fv (scFv) molecules, dAb fragments, and minimal recognition units consisting of the amino acid residues that mimic the hypervariable region of the antibody.

In some embodiments of the invention, the anti-CXCR5 binding agents (or a variant thereof or an antigen-binding fragment thereof) will ameliorate, neutralize, or otherwise inhibit CXCR5 biological activity in vivo (e.g., the binding of CXCL13 to CXCR5).

In some embodiments of the invention, the anti-CXCR5 binding agents (or a variant thereof or an antigen-binding fragment thereof) are antagonist-binding agents that ameliorate, neutralize, or otherwise inhibit CXCR5 biological activity in vivo (e.g., the binding of CXCL13 to CXCR5).

In some embodiments, the anti-CXCR5 binding agent (or a variant thereof or an antigen-binding fragment thereof) is present in the formulations in an amount from about 50 to about 500 mg/mL, about 25 to about 400 mg/mL, about 50 to about 250 mg/mL, about 5 mg/mL to about 280 mg/mL, about 5 mg/mL to about 200 mg/mL, about 5 mg/mL to about 125 mg/mL, about 5 mg/mL to about 75 mg/mL, about 5 mg/mL to about 50 mg/mL, and about 5 mg/mL to about 25 mg/mL. For example, the anti-CXCR5 binding agent may be present in the formulation in an amount of about 5 mg/mL, about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 55 mg/mL, about 60 mg/mL, about 65 mg/mL, about 70 mg/mL, about 75 mg/mL, about 80 mg/mL, about 85 mg/mL, about 90 mg/mL, about 95 mg/mL, about 100 mg/mL, about 105 mg/mL, about 110 mg/mL, about 115 mg/mL, about 120 mg/mL, about 125 mg/mL, about 130 mg/mL, about 135 mg/mL, about 140 mg/mL, about 145 mg/mL, about 150 mg/mL, about 155 mg/mL, about 160 mg/mL, about 165 mg/mL, about 170 mg/mL, about 175 mg/mL, about 180 mg/mL, about 185 mg/mL, about 190 mg/mL, about 195 mg/mL, about 200 mg/mL, about 205 mg/mL, about 210 mg/mL, about 215 mg/mL, about 220 mg/mL, about 225 mg/mL, about 230 mg/mL, about 235 mg/mL, about 240 mg/mL, about 245 mg/mL, about 250 mg/mL, about 255 mg/mL, about 260 mg/mL, about 265 mg/mL, about 270 mg/mL, about 275 mg/mL, or about 280 mg/mL.

In alternative embodiments, the anti-CXCR5 binding agent may be present in the formulation in an amount from about 5 to about 25 mg/mL, from about 26 to about 50 mg/mL, from about 51 to about 75 mg/mL, from about 76 to about 100 mg/mL, from about 101 to about 125 mg/mL, from about 126 to about 150 mg/mL, from about 151 to about 175 mg/mL, from about 176 to about 200 mg/mL, from about 201 mg/mL to about 225 mg/mL, from about 226 mg/mL to about 250 mg/mL, from about 251 to about 280 mg/mL, from about 5 to about 25 mg/mL, from about 40 to about 60 mg/mL, from about 75 to about 85 mg/mL, or from about 90 to about 110 mg/mL.

In a first particular embodiment, a contemplated antibody is an isolated antibody or fragment thereof that specifically binds to the extracellular domain of human CXCR5. The antibody, or fragment thereof, can include: (a) a light chain variable domain comprising the amino acid sequence of SEQ ID NO: 11, and a heavy chain variable domain comprising the amino acid sequence of SEQ ID NO: 12; (b) the amino acid sequences of RSSKSLLHSSGKTYLY (SEQ ID NO: 58), RMSNLAS (SEQ ID NO: 59), MQHLEYPYT (SEQ ID NO: 60), GFSLIDYGVN (SEQ ID NO: 61), VIWGDGTTY (SEQ ID NO: 62), and IVY (SEQ ID NO: 63); (c) a light chain variable domain comprising the amino acid sequence of SEQ ID NO: 13, SEQ ID NO: 14, or SEQ ID NO: 15, and a heavy chain variable domain comprising the amino acid sequence of SEQ ID NO: 16; (d) the amino acid sequences of RSSKSLLHSSGKTYLY (SEQ ID NO: 58), RLSNLAS (SEQ ID NO: 64), MQHLEYPYT (SEQ ID NO: 60), GFSLIDYGVN (SEQ ID NO: 61), VIWGDGTTY (SEQ ID NO: 62), and IVY (SEQ ID NO: 63); (e) the amino acid sequences of RSSKSLLHSSGKTYLY (SEQ ID NO: 58), RLSSNLAS (SEQ ID NO: 65), MQHLEYPYT (SEQ ID NO: 60), GFSLIDYGVN (SEQ ID NO: 61), VIWGDGTTY (SEQ ID NO: 62), and IVY (SEQ ID NO: 63); (f) a variable light chain (VL) comprising the amino acid sequence of SEQ ID NO: 17, SEQ ID NO: 19, or SEQ ID NO: 21, and a variable heavy chain (VH) comprising the amino acid sequence of SEQ ID NO: 23; (g) a variable light chain comprising the amino acid sequence of SEQ ID NO: 30, SEQ ID NO: 31, or SEQ ID NO: 32, and a variable heavy chain comprising the amino acid sequence of SEQ ID NO: 33 or SEQ ID NO: 34; (h) the amino acid sequences of RSSKSLLHSSGKTYLY (SEQ ID NO: 58), RMSNLA (SEQ ID NO: 66), MQHLEYPYT (SEQ ID NO: 60), GFSLIDYGVN (SEQ ID NO: 61), VIWGDGTTY (SEQ ID N: 62), and IVY (SEQ ID NO: 63); (i) the amino acid sequences of RSSKSLLHSSGKTYLY (SEQ ID NO: 58), RLSNLA (SEQ ID NO: 67), MQHLEYPYT (SEQ ID NO: 60), GFSLIDYGVN (SEQ ID NO: 61), VIWGDGTTY (SEQ ID NO: 62), and IVY (SEQ ID NO: 63); (j) the amino acid sequences of RSSKSLLHSSGKTYLY (SEQ ID NO: 58), RLSSLA (SEQ ID NO: 68), MQHLEYPYT (SEQ ID NO: 60), GFSLIDYGVN (SEQ ID NO: 61), VIWGDGTTY (SEQ ID NO: 62), and IVY (SEQ ID NO: 63); (k) a variable light chain comprising the amino acid sequence of SEQ ID NO: 35, and a variable heavy chain comprising the amino acid sequence of SEQ ID NO: 37; (l) a variable light chain comprising the amino acid sequence of SEQ ID NO: 39, SEQ ID NO: 41, or SEQ ID NO: 43, and a variable heavy chain comprising the amino acid sequence of SEQ ID NO: 45 or SEQ ID NO: 47; (m) a variable light chain comprising the amino acid sequence of SEQ ID NO: 55, and a variable heavy chain comprising the amino acid sequence of SEQ ID NO: 56 or SEQ ID NO: 57; or (n) the amino acid sequences of RSSKSLLHSSGKTYLYW (SEQ ID NO: 69), RMSNLA (SEQ ID NO: 66), MQHLEYPYT (SEQ ID NO: 60), GFSLIDYGVN (SEQ ID NO: 61), VIWGDGTTY (SEQ ID NO: 62), and IVY (SEQ ID NO: 63).

In a second particular embodiment, a contemplated antibody is an isolated antibody or fragment thereof that specifically binds to the extracellular domain of human CXCR5. The antibody or fragment thereof comprises a variable light chain comprising the amino acid sequence of SEQ ID NO: 32, and a variable heavy chain comprising the amino acid sequence of SEQ ID NO: 33.

In a third particular embodiment, a contemplated antibody is an isolated antibody or fragment thereof that specifically binds to the extracellular domain of human CXCR5. The antibody or fragment thereof comprises the amino acid sequences of RSSKSLLHSSGKTYLY (SEQ ID NO: 58), RLSSLA (SEQ ID NO: 68), MQHLEYPYT (SEQ ID NO: 60), GFSLIDYGVN (SEQ ID NO: 61), VIWGDGTTY (SEQ ID NO: 62), and IVY (SEQ ID NO: 63).

In any of the first, second, or third particular embodiments above, the antibody or fragment thereof can further include one or more constant regions. The one or more constant regions domains can consist of $C_{H1}$, $C_{H2}$, $C_{H3}$, and/or $C_L$. The one or more constant regions can be from an IgG antibody, which can be, for example, an IgG4 antibody.

In any of the first, second, or third particular embodiments above, the antibody or fragment thereof can be a single chain Fv.

In one embodiment, a pharmaceutical composition is contemplated comprising a therapeutically effective amount of the antibody or fragment thereof of any one the first, second, or third particular embodiments above and a pharmaceutically acceptable carrier.

Buffering Agents

The formulations of the invention can include a citrate buffer as a buffering agent. Other buffers may also be used. A buffering agent maintains a physiologically suitable pH. In addition, a buffering agent enhances isotonicity and chemical stability of the formulation. In some embodiments, the citrate buffer is present in the formulations at a concentration from about 0.5 mM to about 50 mM, e.g., about 5 mM to about 15 mM. For example, the citrate buffer can be present in the formulation at a concentration about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25 mM, about 26 mM, about 27 mM, about 28 mM, about 29 mM, about 30 mM, about 31 mM, about 32 mM, about 33 mM, about 34 mM, about 35 mM, about 36 mM, about 37 mM, about 38 mM, about 39 mM, about 40 mM, about 41 mM, about 42 mM, about 43 mM, about 44 mM, about 45 mM, about 46 mM, about 47 mM, about 48 mM, about 49 mM, or about 50 mM. In some embodiments, the citrate buffer is present in the formulation at a concentration from about 7 mM to about 13 mM, such as from about 9 mM to about 11 mM. In some embodiments, the citrate buffer is present at a concentration of about 10 mM.

In certain embodiments, the formulations of the invention have a pH at or below pH 6. In some embodiments, the pH of the formulations ranges from about 5.0 to about 6.0. For example, the pH of the formulations may be about 5.0, about 5.1, about 5.2, about 5.3, about 5.4, about 5.5, about 5.6, about 5.7, about 5.8, about 5.9, and about 6.0. In some embodiments, the pH of the formulations may range from about 5.5 to about 6.0. In some embodiments, the pH is either about 5.5 or about 6.0. The pH of the formulation may be measured by any means known to those of skill in the art. A means for measuring pH is using a pH meter with a micro-electrode. The pH of the formulation may be adjusted using any means known in the art. Exemplary chemicals for altering the pH of the formulations are hydrochloric acid (HCl) and sodium hydroxide (NaOH).

In certain embodiments, the formulations of the invention have a pH at or below the isoelectric point (pI) of the binding agent, such as an antibody. The isoelectric point is the pH at which a particular molecule or surface carries no net electrical charge. The pI of an anti-CXCR5 binding agent may be determined by any means known to those of skill in the art. In some embodiments, the pI of an anti-CXCR5 antibody is determined by denaturated isoelectric focusing. The pI a fully human IgG4 antibody contemplated herein can range from about 6.9 to about 9.1.

For example, a contemplated formulation includes an anti-CXCR5 binding agent and a citrate buffer, wherein the pH of the formulation is at or below both about pH 6 and the isoelectric point (pI) of the binding agent. The formulations of the invention provide significant improvements over conventional IgG4 binding agent formulations (e.g., phosphate buffered saline (PBS) formulations), which form unwanted byproducts upon increasing the concentration of the binding agent in the formulation. In particular, the formulations of the invention have a reduced amount of aggregates, half-molecules, degradation products, low molecular weight proteins (LMWPs), high molecular weight proteins (HMWPs), and rearrangements of acid, basic, and neutral isoforms of the binding agent in the formulations.

Surfactants

The formulations of the invention can, optionally, further comprise a surfactant, which is also known as a stabilizing agent. Surfactants/stabilizing agents are chemical compounds that interact and stabilize biological molecules and/or general pharmaceutical excipients in a formulation. In certain embodiments, surfactants may be used in conjunction with lower temperature storage. Surfactants generally protect the binding agent from air/solution interface induced stresses and solution/surface induced stresses, which may otherwise result in protein aggregation. Surfactants may include, but are not limited to, polysorbates, glycerin, dicarboxylic acids, oxalic acid, succinic acid, fumaric acids, phthalic acids, and combinations thereof. Those skilled in the art are aware that other surfactants, e.g. non-ionic or ionic detergents, can be used as long as they are pharmaceutically acceptable, i.e., suitable for administration to subjects. The surfactant is, in some embodiments, a polysorbate. Examples of polysorbates include polysorbate 20, polysorbate 40, polysorbate 60, polysorbate 65, and polysorbate 80.

In exemplary embodiments, the surfactant is present in the formulations in an amount from about 0.001% to about 0.1% (w/v). For example, the surfactant may be present in the formulations in an amount of about 0.001% (w/v), about 0.002% (w/v), about 0.003% (w/v), about 0.004% (w/v), about 0.005% (w/v), about 0.006% (w/v), about 0.007% (w/v), about 0.008% (w/v), about 0.009% (w/v), about 0.01% (w/v), about 0.02% (w/v), about 0.03% (w/v), about 0.04% (w/v), about 0.05% (w/v), about 0.06% (w/v), about 0.07% (w/v), about 0.08% (w/v), about 0.09% (w/v), and about 0.1% (w/v). In particular embodiments, the surfactant is present in the formulations from about 0.003% to about 0.05% (w/v), about 0.004% to about 0.025% (w/v), or about 0.005% to about 0.02% (w/v), e.g. about 0.005% (w/v). For example, polysorbate 20 may be present in an amount from about 0.001% to about 0.1% (w/v), about 0.002% to about 0.01% (w/v), about 0.003% to about 0.008% (w/v), and about 0.004% to about 0.006% (w/v), e.g., about 0.005% (w/v). In alternative embodiments, polysorbate 20 is present in an amount from about 0.001% to about 0.1% (w/v), about 0.005% to about 0.05% (w/v), and about 0.0075% to about 0.025% (w/v), e.g., about 0.01% (w/v). In further alternative embodiments, polysorbate 20 is present in an amount from about 0.001% to about 0.1% (w/v), about 0.005% to about 0.05% (w/v), and about 0.01% to about 0.03% (w/v), e.g., about 0.02% (w/v).

Tonicity Agents

The formulations of the invention may, optionally, further comprise a tonicity agent. Typically, tonicity agents are used to adjust or maintain the osmolality of the formulations in order to bring it closer to the osmotic pressure of body fluids, such as blood or plasma. Tonicity agents may also maintain the binding agent levels in a formulation. In part, the tonicity agent contributes to preserving the level, ratio, or proportion of the therapeutically active binding agent present in the formulation. As used herein, the term "tonicity" refers to the behavior of biologic components in a fluid environment or solution. Isotonic solutions possess the same osmotic pressure as blood plasma, and can be intravenously infused into a subject without changing the osmotic pressure of the subject's blood plasma. Indeed, in certain embodiments of the invention, the tonicity agent is present in an amount sufficient to render the formulation suitable for intravenous infusion. Often, the tonicity agent serves as a bulking agent or a stabilizing agent as well. As such, the tonicity agent may allow the binding agent to overcome various stresses, such as freezing and shear. Tonicity agents may include, but are not limited to, saccharides, sugars, glycerol, sorbitol, mannitol, sodium chloride, potassium chloride, magnesium chloride, and other inorganic salts. Those skilled in the art are aware that other tonicity agents can be used as long as they are pharmaceutically acceptable, i.e., suitable for administration to subjects.

In certain embodiments, the tonicity agent is present in the formulations in an amount from about 0.1% to 10% (w/v). For example, the tonicity agent may be present in the formulation in an amount of about 0.1% (w/v), about 0.2% (w/v), about 0.3% (w/v), about 0.4% (w/v), about 0.5% (w/v), about 0.6% (w/v), about 0.7% (w/v), about 0.8% (w/v), about 0.9% (w/v), about 1% (w/v), about 2% (w/v), about 3% (w/v), about 4% (w/v), about 4.5% (w/v), about 5% (w/v), about 5.5% (w/v), about 6% (w/v), about 7% (w/v), about 8% (w/v), about 9% (w/v), and about 10% (w/v). Alternatively, the tonicity agent may be present in the formulation in an amount from about 2% to about 8% (w/v), from about 3% to about 7% (w/v), and from about 4% to about 6% (w/v). In further alternative embodiments, the tonicity agent may be present in the formulation in an amount from about 0.1% to about 1%, from about 0.1% to about 0.5%, from about 0.1 to about 0.3%, and about 0.2%.

In certain exemplary embodiments, the tonicity agent is a saccharide. Examples of saccharides include glucose, sucrose (which is also known as saccharose), maltose, trehalose, dextrose, xylitol, fructose and mannitol. For example, mannitol may be present in an amount of about 1% to about 10% (w/v), about 2% to about 8% (w/v), or about 3% to about 5% (w/v), e.g., about 4% (w/v). Alternatively, sucrose (which is also known as saccharose) may be present in an amount of about 1% to about 10% (w/v), about 3% to about 8% (w/v), or about 4% to about 6% (w/v), e.g., about 4.5, 5, 5.5, or 6% (w/v).

In certain other exemplary embodiments, the tonicity agent is sodium chloride. For example, sodium chloride may be present in an amount of about 0.1% (w/v), about 0.2% (w/v), about 0.3% (w/v), about 0.4% (w/v), about 0.5% (w/v), about 0.6% (w/v), about 0.7% (w/v), about 0.8%

(w/v), about 0.9% (w/v), and about 1% (w/v). Alternatively, sodium chloride may be present in the formulation in an amount from about 0.1% to about 1%, from about 0.1% to about 0.5%, from about 0.1 to about 0.3%, and about 0.2%.

In further exemplary embodiments, the formulations may comprise one or more tonicity agents. For example, the formulations may comprise one or more of the above tonicity agents in the above concentrations. In certain specific embodiments, the formulations may comprise sucrose and sodium chloride, wherein each of the sucrose and sodium chloride concentrations is between about 0.1% to about 10% (w/v). In some embodiments, the sucrose concentration is about 6% and the sodium chloride concentration is about 0.2%. Alternatively, the sucrose concentration is about 4.5% and the sodium chloride concentration is about 0.2%.

In certain embodiments of the invention, the osmolality of the formulations range from about 200 mOsm/kg to about 350 mOsm/kg, about 270 mOsm/kg to about 330 mOsm/kg, about 280 mOsm/kg to about 320 mOsm/kg, or about 290 mOsm/kg to about 310 mOsm/kg, e.g., about 300 mOsm/kg. In other words, the formulations of the invention are, in some embodiments, substantially isotonic, i.e., having substantially the same osmotic pressure as human blood. Osmolality can be measured by any means known to those of skill in the art, such as using vapor pressure or ice-freezing type osmometers. The osmolality of the formulations of the invention can, for instance, be regulated by the one or more tonicity agents described herein.

Amino Acids

The formulations of the invention may, optionally, further comprise an amino acid. Examples of amino acids include, but are not limited to, glycine, alanine, aspartic acid, lysine, serine, tyrosine, cysteine, glutamine, methionine, arginine, and proline. In exemplary embodiments, the amino acid is present in the formulations in an amount from about 0.1% to 5% (w/v). For example, the amino acid may be present in the formulation in an amount of about 0.1% (w/v), about 0.2% (w/v), about 0.3% (w/v), about 0.4% (w/v), about 0.5% (w/v), about 0.6% (w/v), about 0.7% (w/v), about 0.8% (w/v), about 0.9% (w/v), about 1.0% (w/v), about 1.1% (w/v), about 1.2% (w/v), about 1.3% (w/v), about 1.4% (w/v), about 1.5% (w/v), about 1.6% (w/v), about 1.7% (w/v), about 1.8% (w/v), about 1.9% (w/v), about 2.0% (w/v), about 3% (w/v), about 4% (w/v), and about 5% (w/v). Alternatively, the amino acid is present in the formulation in an amount from about 1.3% to about 1.8% (w/v), or about 1.4% to about 1.6% (w/v), e.g., about 1.5% (w/v). In further alternative embodiments, the amino acid is present in the formulation in an amount from about 0.5% to about 1.5% (w/v), or about 0.8% to about 1.2% (w/v), e.g., about 1.0% (w/v). An exemplary amino acid is proline or arginine. For example, proline may be present in the formulation in an amount from about 1% to about 2%, (w/v) about 1.3% to about 1.8% (w/v), about 1.4% to about 1.6% (w/v), e.g., about 1.5% (w/v). Alternatively, arginine may be present in the formulation in an amount from about 0.5% to about 1.5% (w/v), or about 0.8% to about 1.2% (w/v), e.g., about 1.0% (w/v).

Other Excipients

Furthermore, the formulations of the invention may comprise other excipients including, but not limited to, water for injection, diluents, solubilizing agents, soothing agents, additional buffers, inorganic or organic salts, antioxidants, or the like. In some embodiments, however, the formulations of the invention comprise no other excipients, except those described above. Other pharmaceutically acceptable carriers, excipients, or stabilizers, such as those described in Remington's Pharmaceutical Sciences 16th edition, Osol, A. Ed. (1980) may be included in the formulation provided that they do not adversely affect the desired characteristics of the formulation. In a particular embodiment, the formulation is substantially free of preservatives, although, in alternative embodiments, preservatives may be added as necessary. For example, cryoprotectants or lyoprotectants may be included in lyophilized formulations.

Liquid or Lyophilized Formulations

The formulations of the invention may be liquid formulations or lyophilized formulations. In some embodiments, the liquid formulations are ready for injection or may be diluted prior to injection. Alternatively, the formulations may be lyophilized powders. In some embodiments, the lyophilized powders are ready to be combined with one of a plurality of solvent volumes to arrive at a desired concentration just prior to administration.

Exemplary Formulations

In one embodiment of the invention, the invention provides a stable liquid antibody formulation suitable for subcutaneous administration, the formulation comprising:

a) greater than about 100 mg/mL, e.g., about 100 to about 175 mg/mL, of a fully human anti-CXCR5 antibody comprising a heavy chain comprising the amino acid sequence of SEQ ID NO: 33 and a light chain comprising the amino acid sequence of SEQ ID NO: 32;

b) about 10 mM citrate buffer;

c) about 0.1% (w/v) polysorbate 20 or polysorbate 80; and d) about 200 mM arginine;

e) about 4.5-9% sucrose, wherein the pH of the formulation is about pH 6.

In another embodiment of the invention, the invention provides a stable antibody formulation comprising:

a) about 150 to about 175 mg/mL of a humanized IgG4 anti-CXCR5 antibody comprising a heavy chain comprising the amino acid sequence of SEQ ID NO: 33 and a light chain comprising the amino acid sequence of SEQ ID NO: 32;

b) about 10 mM citrate buffer;

c) about 0.1% (w/v) polysorbate 80; and d) about 200 mM arginine;

e) about 4.5% sucrose, wherein the pH of the formulation is about pH 6.0.

In a particular embodiment of the invention, the invention provides a stable antibody formulation comprising:

a) about 175 mg/mL of a humanized IgG4 anti-CXCR5 antibody comprising a heavy chain comprising the amino acid sequence of SEQ ID NO: 33 and a light chain comprising the amino acid sequence of SEQ ID NO: 32;

b) about 10 mM citrate buffer;

c) about 0.1% polysorbate 80; and d) about 200 mM arginine;

e) about 4.5% sucrose, wherein the pH of the formulation is about pH 6.0.

Stability

Contemplated formulations are stable at 5° C. for at least about 1, 2, 3, 4, 5, 6, 7, 8, 9, 10, 11 or 12 months or more, and typically at least about 12, 18, or 24 months, or more. In exemplary embodiments, they are stable at 5° C. for at least about 6 months or more. In other exemplary embodiments, they are stable at 5° C. for at least about 9 months. In further exemplary embodiments, they are stable at 5° C. for at least about 1 year or more, and typically more than about 2 years or more than about 4 years.

Modes of Administration

In certain embodiments of the invention, the formulations are suitable for administration parenterally, intravenously, intramuscularly, intradermally, subcutaneously, or a combination thereof. The formulations of the invention are suitable for delivery by a variety of techniques.

Dosages and Dosage Forms

Effective doses of the formulations of the invention vary depending upon many different factors, including means of administration, target site, physiological state of the subject, whether the subject is human or an animal, other medications administered, and whether treatment is prophylactic or therapeutic. Usually, the subject is a human, but non-human mammals including transgenic mammals can also be treated. Treatment dosages may need to be titrated to optimize safety and efficacy.

The formulations of the invention may be administered on multiple occasions. Intervals between single dosages can be daily, weekly, biweekly, monthly or yearly. Intervals can also be irregular. In some methods, the dosage is adjusted to achieve a certain plasma binding agent, such as an antibody concentration. Dosage and frequency will vary depending on the half-life of the anti-CXCR5 binding agent, such as an antibody, in the subject. In general, human antibodies show the longest half-life, followed by humanized antibodies, chimeric antibodies, and nonhuman antibodies.

In further embodiments, the invention provides a pharmaceutical unit dosage form comprising a therapeutically effective amount of a formulation of the invention for the treatment of one or more diseases in a subject through administration of the dosage form to the subject. In some embodiments, the subject is a human. The human may be an adult or may be an infant. The term "pharmaceutical unit dosage form" refers to a physically discrete unit suitable as unitary dosages for the subjects to be treated, each unit containing a predetermined quantity of active compound calculated to produce the desired therapeutic/prophylactic effect in association with the required citrate buffer and pH.

The unit dosage form may be a container comprising the formulation. Suitable containers include, but are not limited to, sealed ampoules, vials, bottles, syringes, and test tubes. The containers may be formed from a variety of materials, such as glass or plastic, and may have a sterile access port (for example, the container may be a vial having a stopper that can be pierced by a hypodermic injection needle). In some embodiments, the container is a vial. Generally, the container should maintain the sterility and stability of the formulation.

In specific embodiments, the formulations are packaged in 4 mL vials (2R ISO vials) that are made of clear, colorless type I glass, and closed with a stopper (fluoropolymer-coated bromobutyl) sealed with flip-of caps with flange (polypropylene). The vials are, in some embodiments, filled with 1.7 mL of the formulations so that the vial has an overfill volume of about 0.2 mL per vial, and an extractable volume of 1.5 mL. For example, this means that the dosage strength of antibody (e.g., 175 mg/mL) will be contained within 1.5 mL of solution.

In one specific embodiment, the formulations are secondarily packaged in a container, such as a cardboard box, that protects the vials from light.

Kits

Certain embodiments of the invention include a kit comprising a formulation of the invention. The kit may further comprise one or more containers comprising pharmaceutically acceptable excipients, and include other materials desirable from a commercial and user standpoint, including filters, needles and syringes. Associated with the kits can be instructions customarily included in commercial packages of therapeutic, prophylactic or diagnostic products, that contain information about, for example, the indications, usage, dosage, manufacture, administration, contra-indications, and/or warnings concerning the use of such therapeutic, prophylactic or diagnostic products. The kit can also be associated with a label that can be any kind of data carrier (e.g., a leaflet, sticker, chip, print or bar code) comprising information. In certain embodiments, the instructions etc. as listed above can be comprised in or on the label. The kit can further comprise a device for administration of the formulation, and particularly a device that contains the formulation, i.e., a pre-filled device such as, but not limited to, a pre-filled syringe or a pre-filled autoinjector. The kit can also comprise a container comprising the formulation, i.e., a pre-filled container, such as a pre-filled vial, cartouche, sachet, or ampoule.

Combination of Different Embodiments

In the context of the present invention, any of the herein described embodiments can be combined with one or more of the other herein described embodiments unless explicitly stated to the contrary. Particularly, any of the herein described binding agents and antibodies and the herein described formulations thereof can be used in combination with any of the kits, pre-filled devices or pre-filled containers, or can be used in the methods of treatment or medical uses as described herein in connection with the respective antibody (e.g., the stable formulations comprising the anti-CXCR5 antibodies can be combined with any of the herein described kits, containers or devices). Any of the herein described binding agents specifically binding an antigen (e.g., a binding agent specifically binding CXCR5) can also be used in any of the methods of treatment that are described herein in connection with the respective antibodies (i.e., anti-CXCR5) and vice versa.

Examples

The following Examples illustrate specific embodiments of the invention. They are set forth for explanatory purposes only and are not to be taken as limiting the invention.

Example No. 1: Analysis of Stardust Particle Formation

A) Introduction

The Drug Product (DP), designated as SAR113244 by Sanofi, is a humanized IgG monoclonal antibody (mAb) that selectively binds human CXCR5 and is disclosed in U.S. Pat. No. 8,647,622. It was developed for parenteral subcutaneous administration as a solution for injection at a concentration of 100 mg/mL. DP solution for injection was packaged in 2 mL clear and colorless vials (glass type I) closed with stoppers (fluoropolymer-coated bromobutyl rubber) and flip-off caps (polypropylene) with flange (aluminum).

Formulation development for the SAR113244 mAb concluded in a formulation for a phase I clinical study that contained arginine at 10 mg/mL, NaCl at 2 mg/mL, polysorbate 20 at 0.01% and citrate buffer at 10 mM and had a pH of 6 (referred to hereafter as "DP solution"). This formulation was stable in terms of chemical stability and in terms of sub-visible particles. However, after approximately one year, formation of visible particles occurred when the formulation was stored in a glass primary packaging material, e.g. vials or prefilled syringes. Formation of visible particles did not occur when the primary packaging material was plastic (bag or flask).

It was during a compatibility study planned for Phase 1 clinical study that visible particles were found in the DP solution stored in 2 R ISO glass vials (Schott, Elmsford, NY). The particles were very small, shiny, and suspended, and therefore termed "Stardust particles." The discovery of the Stardust particles caused the study to be stopped, and the DP solution batches were put on quarantine. An immediate action plan was put in place and an online filter option was investigated and applied for the clinical study. This was summarized in an amendment which was approved from the health authorities with no comments, and the study could restart. However, for further clinical studies it was desirable to develop a formulation without Stardust particles. Here, we describe a method to prepare a SAR113244-containing highly concentrated formulation that is free of Stardust particles.

Stardust particles were not present in DP solutions stored in a bag or stored in a Nalgene® bottle. Stardust particles were also not present in DP solutions stored in glass vials directly after manufacturing process. Stardust particles in the glass vials are believed to have occurred approximately after one year of storage. Other products (for example, protein therapeutics) filled in the same kind of vials, using the same stoppers, using the same filling line, using the same equipment were checked for particles and never developed any Stardust particles.

Measurements of subvisible particles using Microflow® imaging or light obscuration in the DP solution were always in the acceptance range regardless of the presence of Stardust particles. No differences in subvisible particles of samples directly after manufacturing and samples with long storage time 1 year were detected during the stability studies. To get rid of the Stardust particles a new, Stardust-free formulation was then developed for phase II clinical trials. Ultimately, the formulation demonstrated stability in glass containers for 6 months under accelerated conditions (40° C.) and for 12 months at 2-8° C.

B) Methods

Visual Inspection of DP solution: Visual inspection of DP solution was performed by trained staff directly after finalizing the batch of DP. Vials were tested by inverting the vials once or twice and subsequent observation of the vials for 5 to 15 seconds (Laboratory 1: Liquid Inspection Viewer Apollo II; Laboratory 2: Black Box) or observation of rotating vials with no inversion (Laboratory 3: Seidenader vial inspection machine with a magnifier). Light source was 2000-3750 Lux.

Glass Delamination in DP solution containers: Glass delamination was analyzed for four different batches (3 clinical batches, one tech batch). For this purpose, 10 mL of DP solution per batch were tested to determine the amount of glass elements, namely Si, B, Ca, and Al that leached into the solution. Four sets of containers were used for this study: SCHOTT Type I plus ($SiO_2$-coated vials), SCHOTT standard Fiolax, SCHOTT DC (delamination controlled), and BD prefillable syringes. The different solutions were stored at 60° C. and analyzed at three different time points (after 1, 4, and 12 weeks). Visual inspection was performed by eye and magnifying video camera with respect to the presence of "flake-like" and/or "non-flake-like" particles. Ten containers were tested at each time point. Furthermore, optical inspection of 5 empty containers per control sample set was performed using stereo-microscopy with extended depth of focus to determine qualitatively if there were any indications for glass corrosion or reaction zones present on the interior surfaces of the containers. Additionally, 10 emptied containers per sample set and pull point were analyzed by stereomicroscopy with extended depth of focus to determine if there are any indications for glass corrosion or reactive zones present on the interior surface. On the interior surface of the two "worst" containers per set for each pull point, SEM cross-sectional analysis was performed. In total, 10 mL of placebo solution (containing 10 mM citrate buffer, 2 g/L NaCl, 10 g/L arginine-HCl, 45 g/L sucrose (4.5%), and 0.01% polysorbate 20) pooled from the containers for each sample set at each pull point were analyzed to quantitatively determine the amount of glass elements leached into the solution.

Mechanical stability studies: To determine whether mechanical stress contributed to the formation of Stardust particles in the DP solution, mechanical stress studies were performed. During manufacturing, the DP solution was added to the mixing vessel and excipients were added. A volume of 10 mL of 8 different formulations (see Table No. 1 below—each composition being based on citrate buffer) were stirred at 200 rpm for either 30 min or 2 h. After mixing the excipients, the solution was checked for the occurrence of visible particles. The solution was then filtered and filled in 2R glass vials. Visual Inspection followed and the solutions were stored at 40° C. for 4 weeks and inspected each week.

TABLE NO. 1

Overview of Tested Formulations.

| Sample | Composition |
|---|---|
| A | Citrate buffer pH 6 100 mg/mL, no DP |
| B | 100 mg/mL DP with 0.01% PS 20 |
| C | 100 mg/mL DP with 0.05% PS 20 |
| D | 100 mg/mL DP with 0.1% PS 20 |
| E | 100 mg/mL DP with 0.01% PS 80 |
| F | 100 mg/mL DP with 0.05% PS 80 |
| G | 100 mg/mL DP with 0.1% PS 80 |
| H | 100 mg/mL DP with no PS |

DP - drug product (SAR113244).

RapID Studies (Filtration, Raman, and FT-IR): During this study, 5 DP solution samples were analyzed. A visual inspection of the DP solutions in closed containers was performed first. The solutions of each sample were filtrated on separate gold-coated polycarbonate filter membranes (pore size 0.8 μm) with an active area having a 4 mm diameter. The emptied vials were rinsed with 2×2 mL of particle-free water, and the stopper was rinsed with 1×2 mL of particle-free water. To ensure that all particles were transferred to the filter, the funnel within the filtration equipment was rinsed with 8 mL of particle-free water. Photographs of the observed particles were taken via video microscope. Some of the largest particles (>50 μm) were further analyzed applying different spectroscopic methods. The Raman spectroscopic investigations were performed manually by image analysis using the Single Particle Explorer (SPE) manufactured by rap.ID particle Systems GmbH. This device works with a laser wavelength of 532 nm. For FT-IR and/or ATR spectroscopy, the FT-IR spectrometer LUMOS (serial no. 190) manufactured by Bruker was used. One of the analyzed particles was further investigated via Scanning Electron Microscope SEM-EDX (TM 3000) manufactured by Bruker.

Filtration—microscopy: Particles were isolated from 5 vials of each batch applying a cellulose nitrate filter with a pore size of 0.45 μm. The obtained particles were analyzed by optical microscopy. The particles were further characterized via IR spectroscopy using the IR microscope Hyperion 2000 at 15× magnification.

Measurement of Subvisible Particles:

1. Optical particle counter: An optical particle counter (HIAC, Hach) was used to measure the amount of subvisible particles in the protein formulation. As required by pharmacopoeia (USP, Ph. Eur.), particles larger than 10 μm and 25 μm were investigated. Detection of particles is done by photodetectors that detect optical disturbances of the illumination caused by the particles in the view volume.

2. Flow-imaging microscopy: Flow-imaging microscopy (Micro-flow imaging (MFI), Protein simple) was used to measure the amount of subvisible particles in the protein formulation. As required by pharmacopoeia (USP, Ph. Eur.), particles larger than 10 μm and 25 μm were investigated. Particles were detected by a digital camera.

3. SEC: The relative amount of soluble aggregates in the nanometer size range was measured using size exclusion chromatography (SEC). In addition, the purity or relative amount of monomer was reported.

4. DLS: The presence of aggregates and particles in the nanometer size range were measured using dynamic light scattering (DLS) (Zetasizer Nano-ZS, Malvern). Hydrodynamic diameter and polydispersity were measured.

Figures 4, 5:
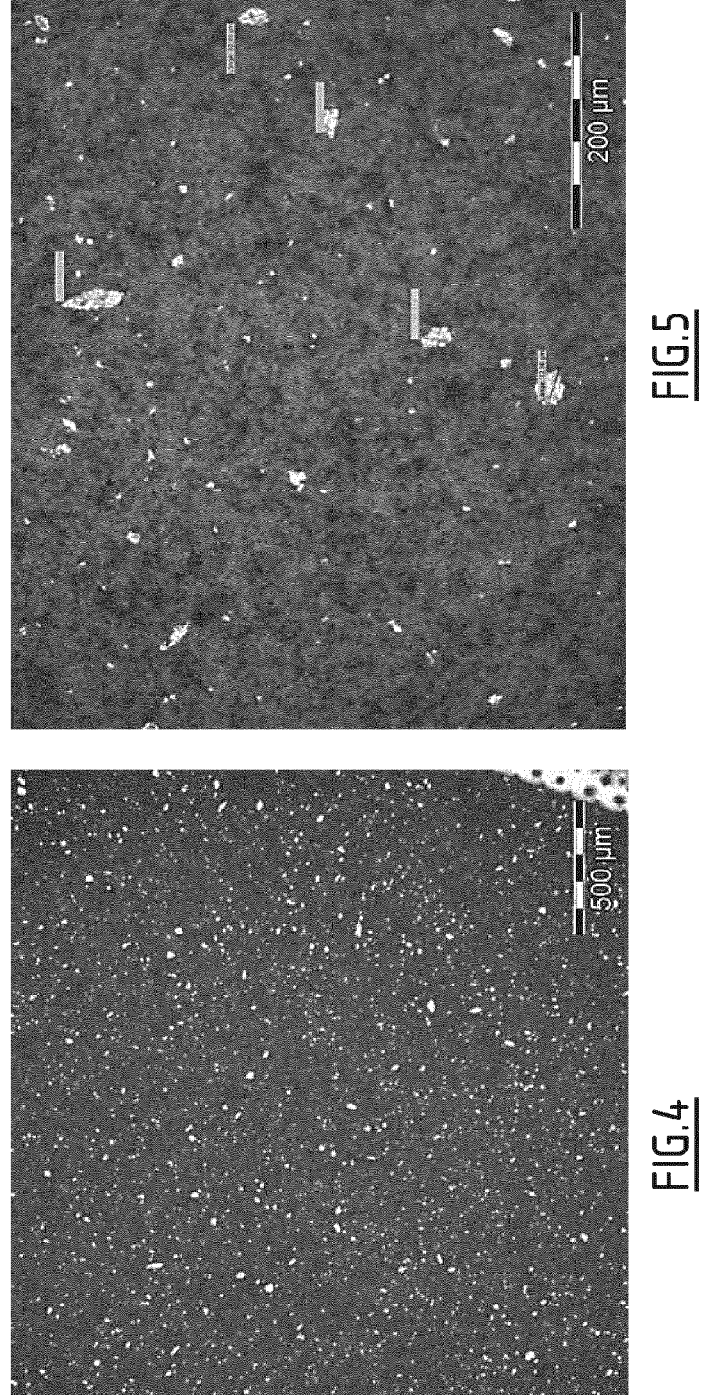
FIG. 4 is a photomicrograph of a cellulose filter after filtration of a first anti-CXCR5 antibody drug product (DP; SAR113244) stored in Nalgene bottle. Magnification is 50×.
FIG. 5 is a photomicrograph of the cellulose filter of FIG. 4 at 200× magnification.
Figures 6, 7, 8:
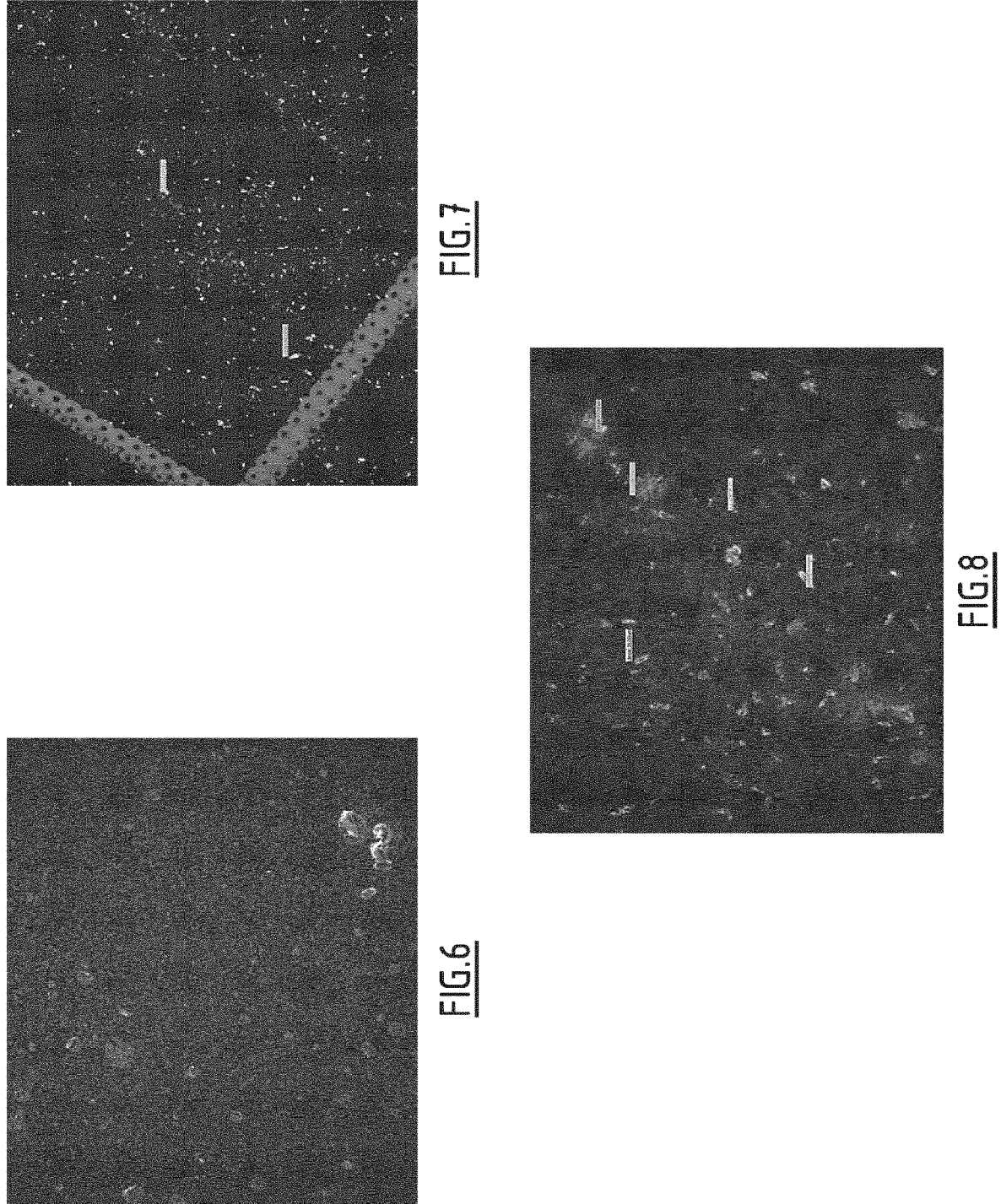
FIG. 6 is a photomicrograph of a cellulose filter after filtration of a second anti-CXCR5 antibody DP. Magnification is 50×.
FIG. 7 is a photomicrograph of a cellulose filter after filtration of a first control anti-CXCR5 antibody DP. Magnification is 50×. The first control anti-CXCR5 antibody DP is a "Stardust free" control formulation (SAR252067) that demonstrated particle formation similar to the first anti-CXCR5 antibody DP, but not Stardust particles. Such occurrences demonstrate the difficulty in Stardust particle analysis.
FIG. 8 is a photomicrograph of the cellulose filter of FIG. 7 at 200× magnification.
Figures 9, 10:
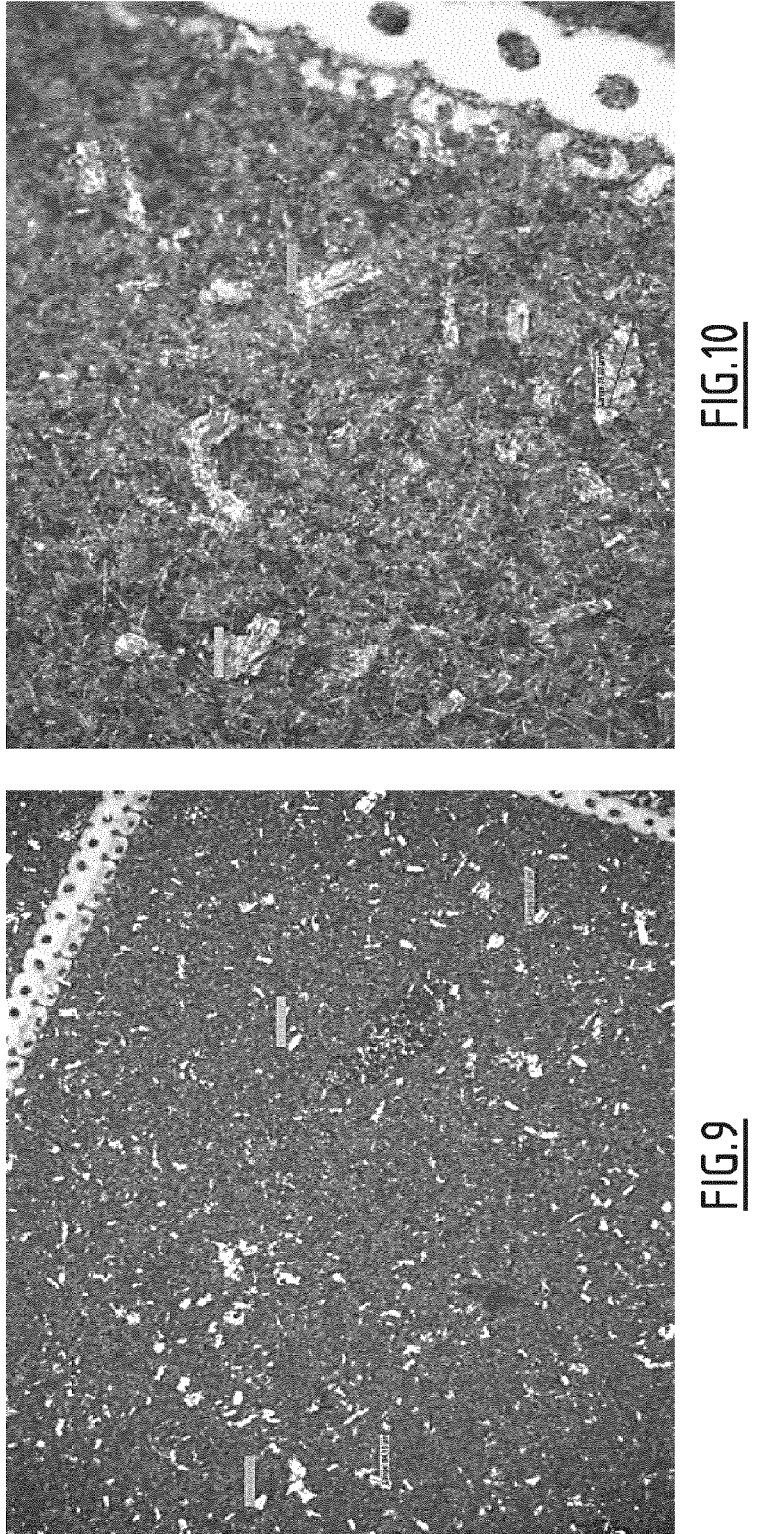
FIG. 9 is a photomicrograph of a cellulose filter after filtration of a SAR341403 DP. Magnification is 50×.
FIG. 10 is a photomicrograph of the cellulose filter of FIG. 9 at 200× magnification.
Figures 11, 12:
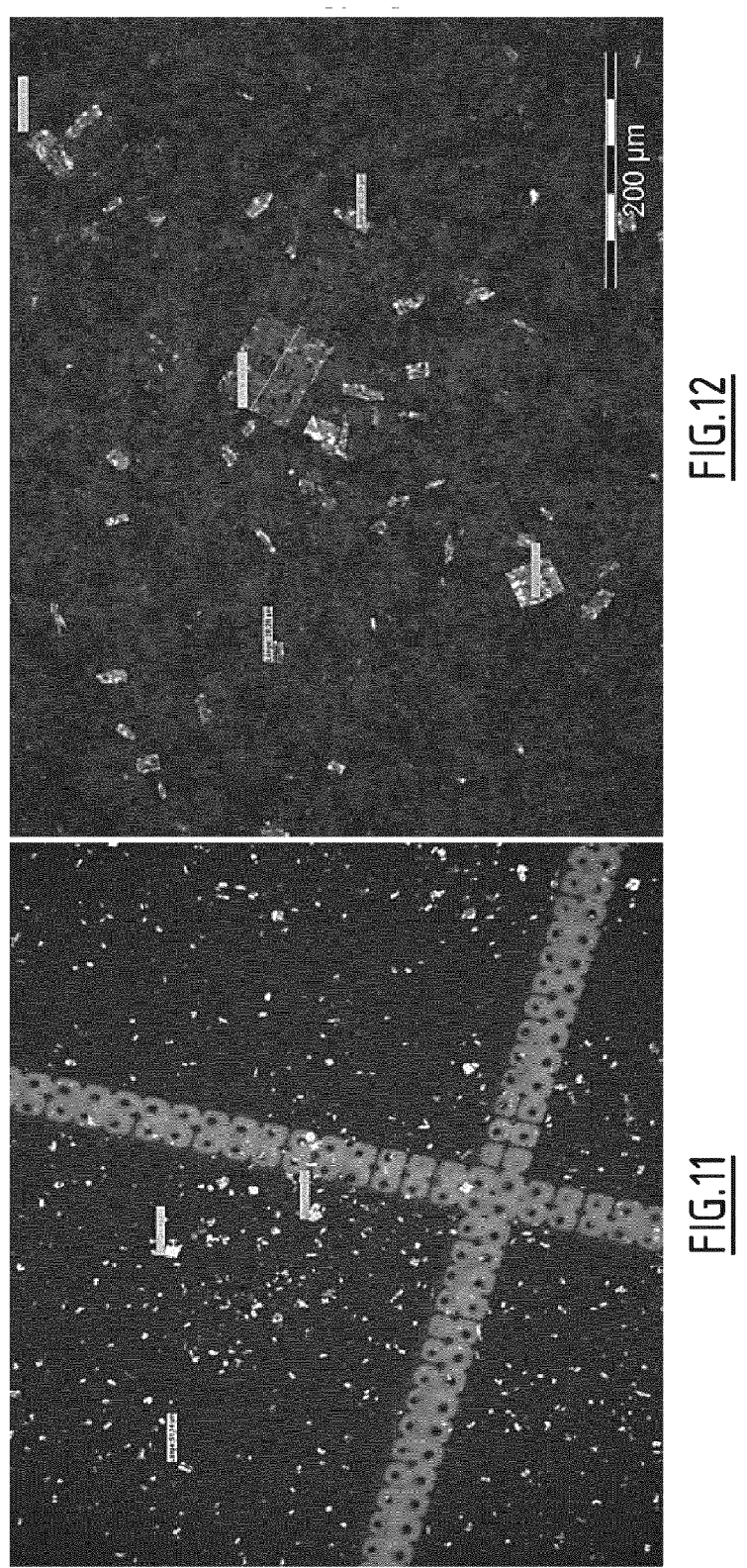
FIG. 11 is a photomicrograph of a cellulose filter after filtration of a second control anti-CXCR5 antibody DP (SAR341403). Magnification is 50×. The second control anti-CXCR5 antibody DP is another "Stardust free" control formulation that demonstrated particle formation similar to the first anti-CXCR5 antibody DP, and further demonstrates the difficulty in Stardust particle analysis.
FIG. 12 is a photomicrograph of the cellulose filter of FIG. 11 at 200× magnification.

C) Results and Discussion:

Filtering Experiments:

To understand the Stardust particle phenomenon, we tried to isolate the particles from the SAR113244 drug product (DP solution). Isolation of particles in a suspension can be achieved by filtration or by trying to take out the particles with a pipette or spatula. However, the characterization of the Stardust particles was very challenging as they could not be isolated. Filtration on a cellulose filter did not isolate Stardust particles (see Table No. 2 and FIGS. 1-3). While filtering three placebo solutions did not lead to any particles on the filter, DP solution from a Nalgene bottle showed a significant amount of glittering particles (FIGS. 4 and 5). Although the absolute number of particles on the filter seemed lower than for the "Stardust"-affected samples, aspect and size did not differ substantially from the particles isolated before. Therefore, the validity of the method of vacuum filtration to isolate "Stardust" particles must be questioned, because DP solution from the Nalgene bottle did not show any Stardust particles. The Drug Substance of SAR113244 also showed particles on the filter (FIG. 6), even though the Drug Substance is Stardust particle-free: Drug Substance was stored in a plastic bag only in citrate buffer (old drug substance from phase 1 process) and did not show particles when visual inspection was performed, but after filtration, particles could be seen on the filter.

Samples from different protein-based therapeutics (SAR252067 and SAR341403) again showed the presence of particles on the filter (FIGS. 7-12), although the solutions had been clear (Stardust particle-free). These findings show that vacuum filtration of highly concentrated antibody solutions bears the risk that solution constituents precipitate on the filter and make the identification of possible subvisible or visible particles present in the solution impossible.

TABLE NO. 2

| | Presence of particles on filter paper. | |
|---|---|---|
| Sample | Presence of Stardust particles in protein formulation | Presence of particles on cellulose filter after filtration |
| SAR113244 | Yes | Yes |
| SAR252067 | No | Yes |
| SAR341403 | No | Yes |
| Placebo solution I | No | No |
| Placebo solution II | No | No |
| Placebo solution III | No | No |

Figure 13:
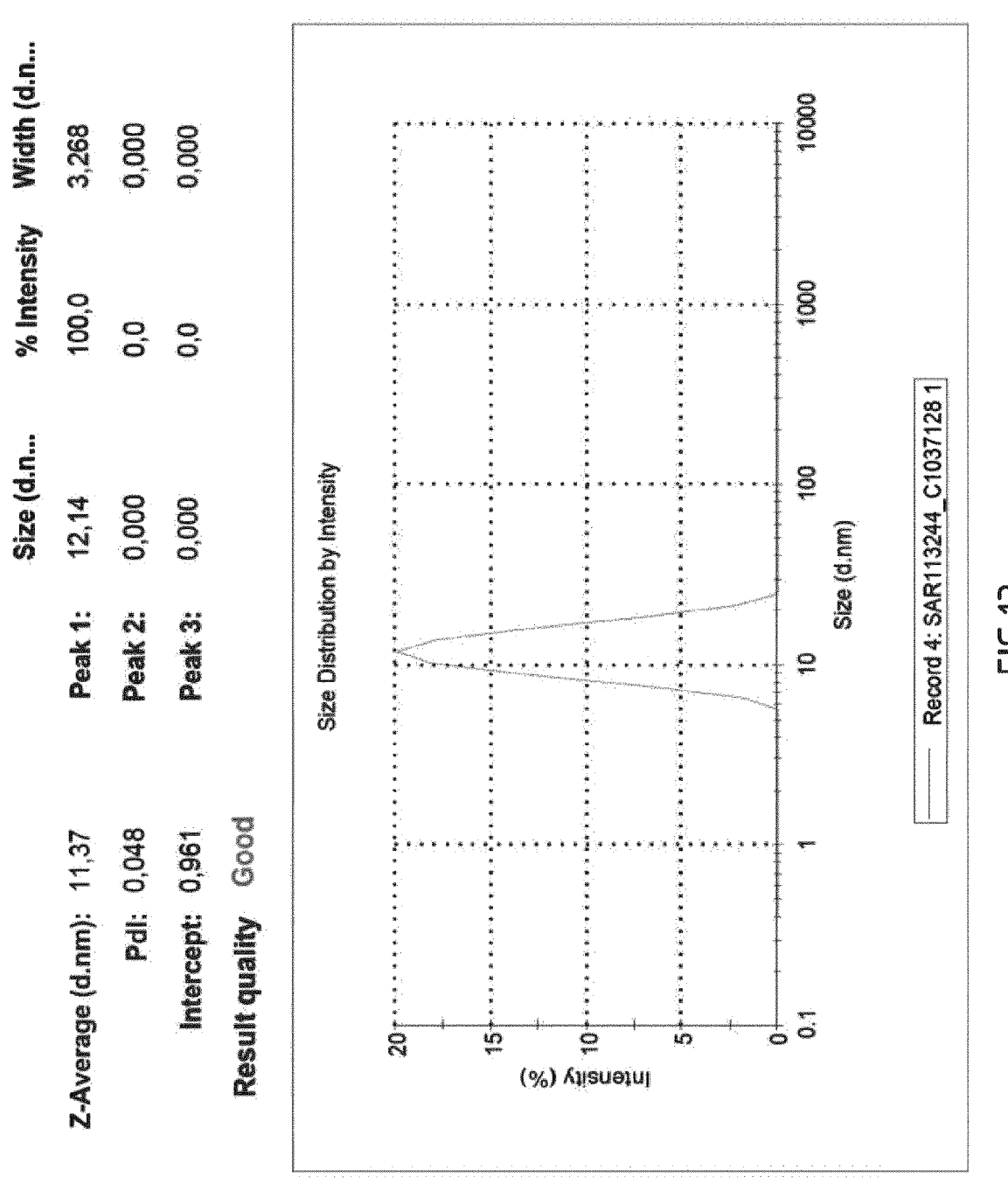
FIG. 13 is a DLS measurement size distribution chart for DP SAR113244 solution stored in a plastic bottle (Stardust-free solution).
Figure 14:
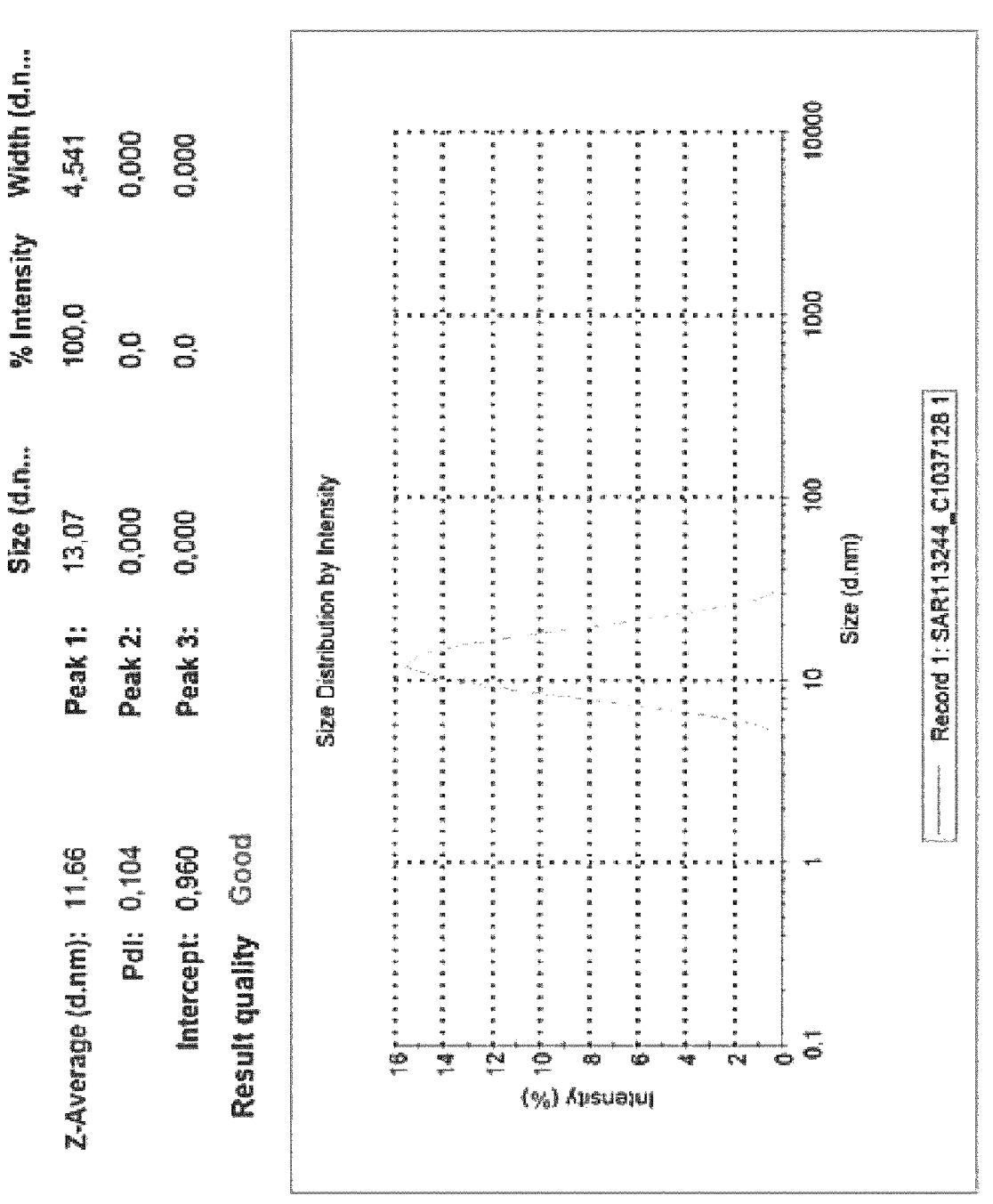
FIG. 14 is a DLS measurement size distribution chart for DP solution stored in glass vials (Stardust-containing solution).

Measurement by DLS:

The measurement of protein aggregates measured by Dynamic Light Scattering did show that the DP solution stored plastic bottles with no Stardust particles (FIG. 13) has a lower polydispersity index than the Stardust-containing DP solution stored in glass vials (FIG. 14). This could be an indication that conformational changes in the SAR113244 molecule might be the underlying cause for Stardust particle formation. This result, in addition to the visual inspection, indicates that the glass container has a role in the Stardust formation.

Delamination Study:

One possible cause for Stardust particle formation was that delamination occurred from the glass vials. Therefore, a delamination study was performed. The delamination study was carried out with a placebo solution containing 10 mM citrate buffer, 2 g/L NaCl, 10 g/L arginine-HCl, 45 g/L (4.5%) sucrose and 0.01% polysorbate 20. The placebo solutions were stored in different kind of glass vials outlined in Table No. 3.

TABLE NO. 3

| | Primary Packaging Used for Delamination Study. |
|---|---|
| Sample | Primary packaging material |
| 128A | 2R ISO Vials (FC) |
| 128B | 2R ISO Vials Type I plus (TIP) |
| 128C | 2R ISO Vials Delamination controlled (DC) |
| 128D | Prefilled syringe (BD Biotech, Hypak SCF, "BD Syringe) |

No delamination was found under accelerated conditions (60° C.) (see Table Nos. 4A and 4B) after 1, 4, or 12 weeks.

TABLE NO. 4A

| Summary for control samples (not sterilized) | | | |
|---|---|---|---|
| Sample | 01 (TIP) | 02 (FC) | 03 (DC) |
| Delamination confirmed[a] | no | no | no |
| Early indicators for delamination[b] | no | no | no |
| Glass attack[c] | no | no | no |
| Others[d] | yes | yes | yes |

| Summary for control samples (sterilized) | | | |
|---|---|---|---|
| | 05 (TIP) | 06 (FC) | 07 (DC) | 08 (BD syringe) |
| Delamination confirmed[a] | no | no | no | no |
| Early indicators for delamination[b] | no | no | no | no |

TABLE NO. 4A-continued

| Summary for control samples (not sterilized) | | | |
|---|---|---|---|
| Glass attack[c] | no | yes | yes | no |
| Others[d] | yes | yes | yes | yes |

| Summary for t0 (initial) | | | |
|---|---|---|---|
| | 10 (128A) | 11 (128B) | 12 (128C) | 13 (128D) |
| Delamination confirmed[a] | no | no | no | no |
| Early indicators for delamination[b] | no | no | no | no |
| Glass attack[c] | no | no | no | no |
| Others[d] | yes | yes | yes | yes |

| Summary for t1 (1 week, 60° C.) | | | |
|---|---|---|---|
| | 20 (128A) | 21 (128B) | 22 (128C) | 23 (128D) |
| Delamination confirmed[a] | no | no | no | no |
| Early indicators for delamination[b] | no | no | no | no |
| Glass attack[c] | no | no | no | no |
| Others[d] | yes | yes | yes | yes |

TABLE NO. 4B

| Summary of glass corrosion (glass attack) and delamination. | | | |
|---|---|---|---|
| Summary for t2 (4 weeks, 60° C.) | | | |
| Sample | 30 (128A) | 31 (128B) | 32 (128C) | 33 (128D) |
| Delamination confirmed[a] | no | no | no | no |
| Early indicators for delamination[b] | no | no | no | yes |
| Glass attack[c] | yes | yes | yes | yes |
| Others[d] | yes | yes | yes | yes |
| Summary for t3 (12 weeks, 60° C.) | | | |
| | 40 (128A) | 41 (128B) | 42 (128C) | 43 (128D) |
| Delamination confirmed[a] | no | no | no | no |
| Early indicators for delamination[b] | no | no | no | yes |
| Glass attack[c] | yes | yes | yes | yes |
| Others[d] | yes | yes | yes | yes |

[a]delamination confirmed: sharp edges or delaminated areas (SEM);
[b]early indicators: reaction zone at the interior surface (SEM), coloration observed by visual inspection not less than "weak" (SM), Si/B concentration ratio below or equal to 5 and Si concentration (ICP) above 10 mg/mL (1 mL up to 2 mL filling volume);
[d]others: shallow pits, shallow bumps, small holes, deposits (SEM), weak-to-medium scattering observed by visual inspection (SM), local reaction zone (lateral dimension below 20 µM)(SEM).

However, an increased concentration of glass components (Al, Si, B, Ca) was detected in the solution over long storage (12 weeks, 60° C.)(see Table No. 5).

TABLE NO. 5

| Concentrations of Dissolved Glass Elements (ICP-analyses) Under Accelerated Conditions. | | | | |
|---|---|---|---|---|
| Element | Unit | Method | Limit of Quantitation (LOQ) | Placebo bulk solution |
| B | mg/L | ICP-OES | 0.5 | <0.5 |
| Al | mg/L | ICP-MS | 0.01 | <0.01 |
| Ca | mg/L | ICP-MS | 0.05 | 0.087 |
| Si | mg/L | ICP-OES | 0.5 | <0.5 |

| t0: Initial samples | | | | | | |
|---|---|---|---|---|---|---|
| Element | Unit | Method | Sample 10 128A | Sample 11 128B | Sample 12 128C | Sample 13 128D |
| B | mg/L | ICP-OES | <0.5 | <0.5 | <0.5 | <0.5 |
| Al | mg/L | ICP-MS | 0.047 | <0.01 | 0.057 | <0.01 |
| Ca | mg/L | ICP-MS | 0.19 | 0.11 | 0.23 | 0.10 |
| Si | mg/L | ICP-OES | 0.70 | 0.61 | 0.60 | 0.71 |

| t1: 1 week at 60° C. | | | | | | |
|---|---|---|---|---|---|---|
| Element | Unit | Method | Sample 20 128A | Sample 21 128B | Sample 22 128C | Sample 23 128D |
| B | mg/L | ICP-OES | <0.5 | <0.5 | 0.52 | <0.5 |
| Al | mg/L | ICP-MS | 0.52 | <0.01 | 0.55 | 0.018 |
| Ca | mg/L | ICP-MS | 0.29 | 0.10 | 0.32 | 0.13 |
| Si | mg'L | ICP-OES | 3.4 | 6.8 | 3.7 | 0.69 |

| t2: 4 weeks at 60° C. | | | | | | |
|---|---|---|---|---|---|---|
| Element | Unit | Method | Sample 30 128A | Sample 31 128B | Sample 32 128C | Sample 33 128D |
| B | mg/L | ICP-OES | 1.36 | <0.5 | 1.28 | 0.75 |
| Al | mg/L | ICP-MS | 1.8 | 0.21 | 1.9 | 0 99 |
| Ca | mg/L | ICP-MS | 0.48 | 0.17 | 0.50 | 0.20 |
| Si | mg/L | ICP-OES | 12.5 | 19.6 | 12.6 | 11.0 |

Based on these observations, it is very likely that the glass components (Al, Si, B, Ca) initiate the particle formation, as this is the only difference that was observed when comparing the mAb formulation in vials compared to the formulation in a Nalgene® bottle. Placebo studies showed no delamination, but a leaching of some components, which can also be assumed for DP-solutions with protein. Moreover, this study established that Stardust particles do not occur in the absence of protein.

Figure 15:
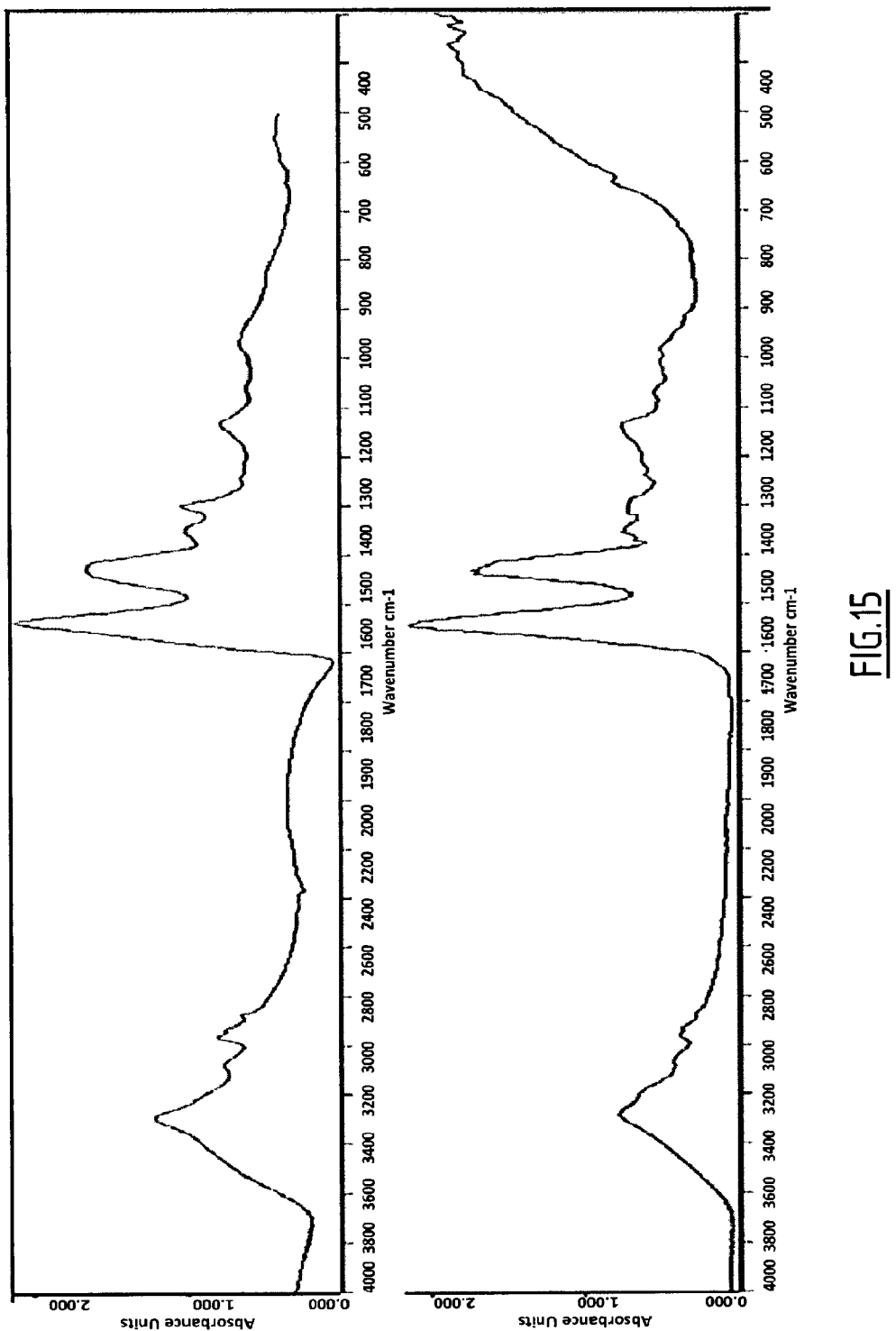
FIG. 15 shows a FT-IR spectrum of a particle (top trace) from sample; bottom trace indicates spectrum for a protein as comparison; a broad band at 3300 $cm^{-1}$ and two amide bands at 1650 $cm^{-1}$, 1520 $cm^{-1}$, respectively, are typical for proteins.
Figure 16:
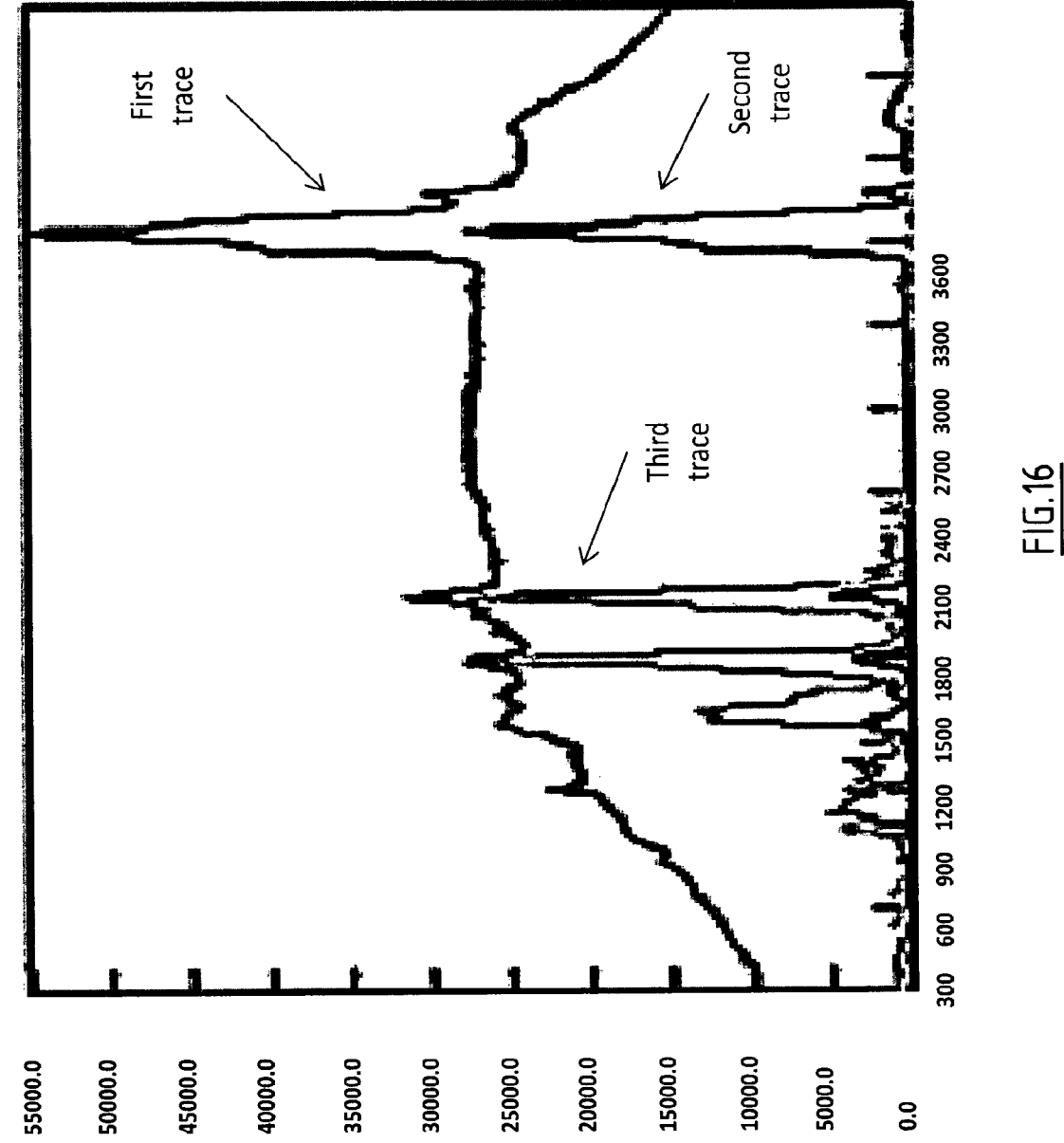
FIG. 16 is a Raman spectrum of a particle that was identified as protein; first trace indicates spectrum of particle from sample; second trace indicates spectrum of particle from sample with subtracted background; third trace indicates comparison of best match from database (protein).
Figure 17:
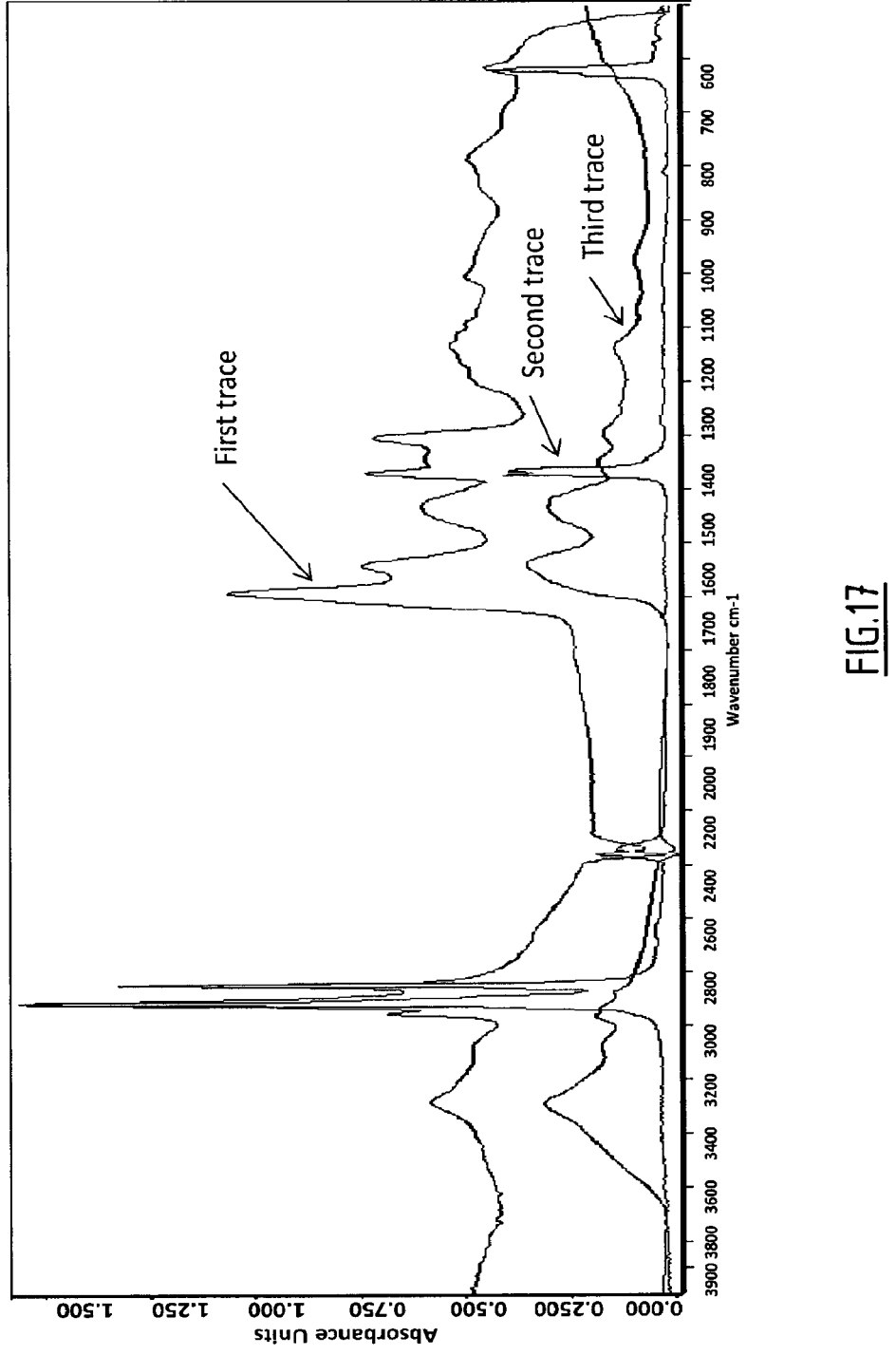
FIG. 17 is a FT-IR spectrum of a particle that was identified as protein. The first trace indicates FT-IR spectrum of particle from sample; the second trace indicates best match with database (polyethylene); the third trace indicates spectrum for a protein as comparison; a broad band at 3300 $cm^{-1}$ and two amide bands at 1650 $cm^{-1}$, 1520 $cm^{-1}$, respectively, are typical for proteins.
Figure 18:
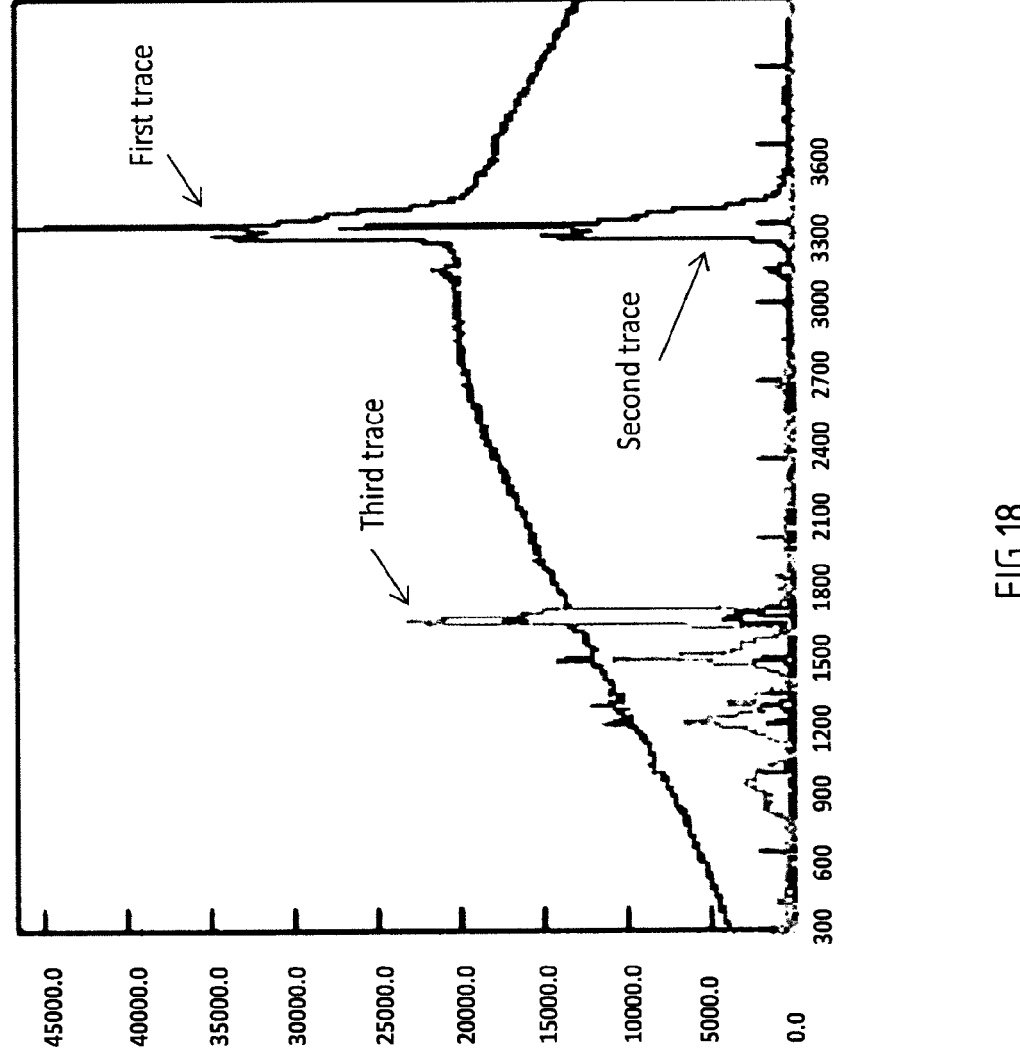
FIG. 18 is a Raman spectrum of a particle that was identified as protein. The first trace indicates spectrum of particle from sample; second trace indicates spectrum of particle from sample with subtracted background; third trace indicates comparison of best match from database that was identified as polyethylene.

RapID—study: The goal of this study was to determine what the Stardust particles consist of. Previous filtration studies were unsuccessful as it was not possible to isolate the particles on filters. RapID offers a solution with gold filters. Here, the DP solution was filtered on a gold filter and then analyzed using FT-IR (FIG. 15) and Raman spectroscopy (FIG. 16). The results showed that in 3 of 5 vials, protein particles were detected. In the other vials, polyethylene has been detected (FIGS. 17 and 18). The samples that contained polyethylene most likely also contained protein as typical absorption peaks for protein above 3000 cm$^{-1}$ were also seen in FT-IR analysis (FIG. 17). It must be stated that the samples were very old (4 years–shelf life=3 years). Therefore, additional studies need to be performed with samples where Stardust particles have just been detected. However, it is believed that protein aggregation, at least in part, underlies Stardust particle formation. Therefore, new antibody formulations designed to avoid protein aggregation are believed to able to avoid Stardust particle formation.

Further, while Stardust particles were discovered and described in the context of a specific anti-CXCR5 antibody, it is believed that other antibodies could exhibit similar storage problems and could thus potentially benefit from the proposed antibody formulations presented herein.

Example No. 2: Development of Stardust Particle-Free Formulations

A) Introduction:

To avoid Stardust particle formation, a new formulation had to be developed. During this process, chemical stability and absence of sub-visible particles were equally important.

B) Methods and Results:

To get a robust formulation that is not prone to aggregate over a prolonged period of time mechanical stress studies were performed on various experimental samples. The samples were stressed using a magnetic stirrer, and after filtration and storage under accelerated conditions, the samples were tested regarding Stardust particle formation (visual inspection). With the mechanical stress study, it could be shown that increased concentrations of Polysorbate 20 or Polysorbate 80 decreases the amount of particles in the antibody formulation. Based on these results a stability study was performed, in which highly concentrated SAR113244 formulations up to 175 mg/mL were tested in glass vials and prefilled syringes. No Stardust particles were observed for any SAR113244 concentration when the Polysorbate 20 or Polysorbate 80 concentration was at 0.1%. Even at accelerated conditions (6 month, 40° C.) visual particles were not present. Therefore, highly concentrated formulations containing 100-175 mg/mL were put on stability and no Stardust particles formed. Chemical stability was achieved when the formulation contained about 100-175 mg/mL SAR113244, about 200 mM arginine, about 4.5-9% sucrose, about 0.1% polysorbate 20 or about 0.1% polysorbate 80 and about 10 mM citrate buffer.

Mechanical stress study: Experimental formulations were made by first adding the drug product (SAR113244) to the mixing vessel and excipients were subsequently added (see Table No. 1 above). After mixing the excipients, the solutions were filtered and added to a glass vial. Finally, the final formulations were visually inspected.

Figure 19:
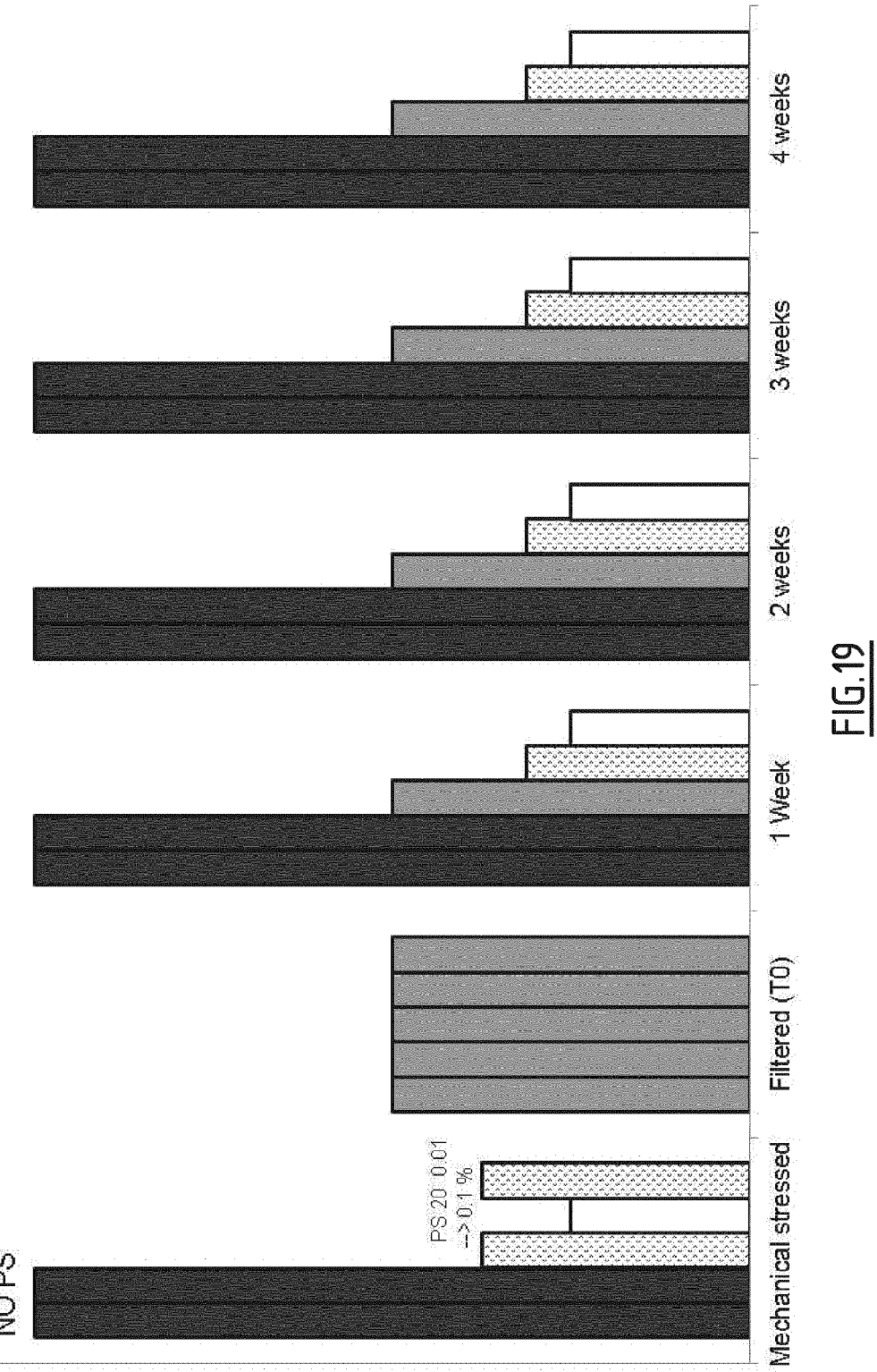
FIG. 19 illustrates the results of particle formation during mechanical stress study; dark grey=visible particles, light grey=1-2 particles, pointed white=mostly clear solution, white=particle free solution; bars indicate from left to right: Formulations A, H, B, C, and D (see Table No. 1).
Figure 20:
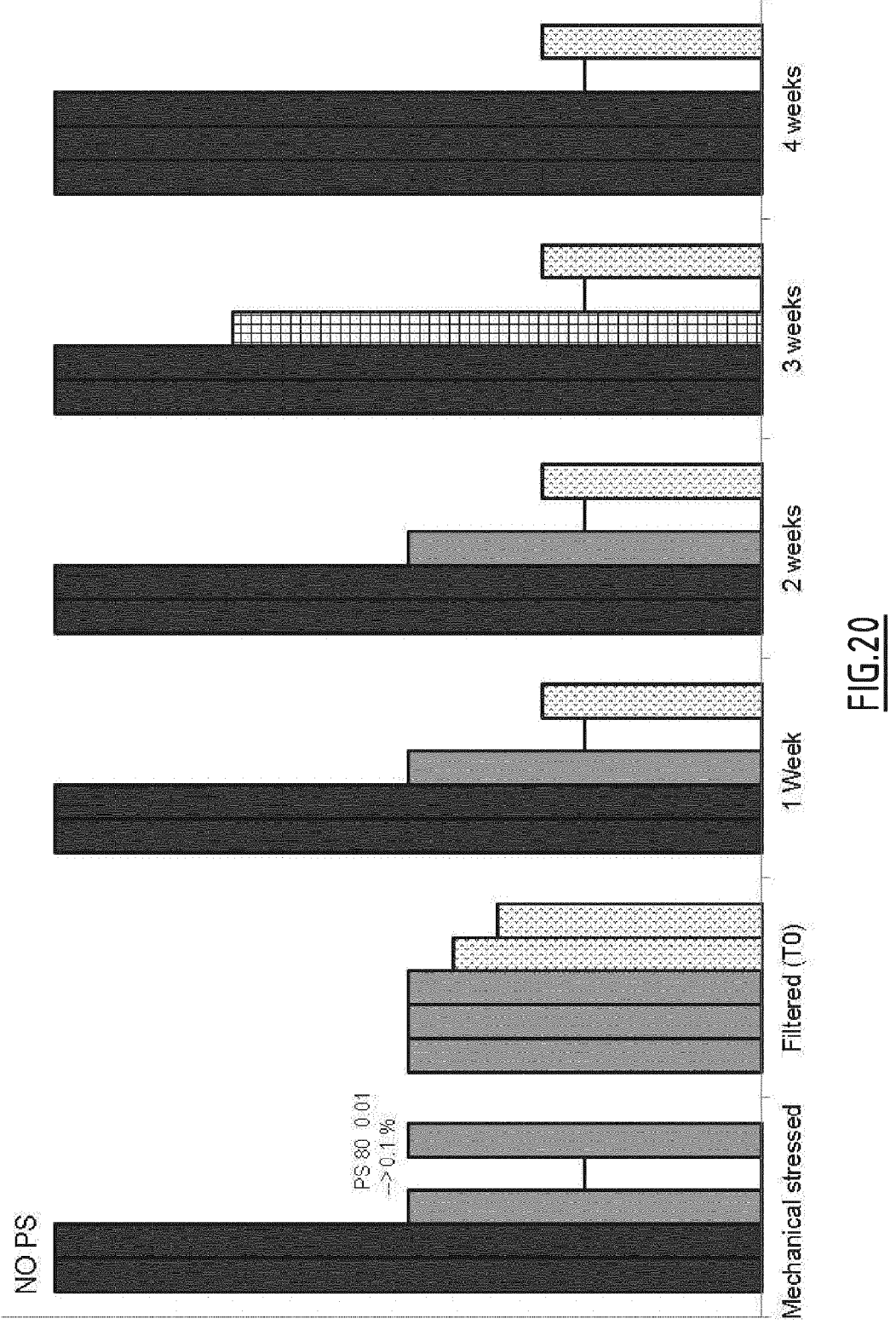
FIG. 20 illustrates the results of particle formation during mechanical stress study; dark grey=visible particles, checkered=Stardust or Stardust like particles, light grey=1-2 particles, pointed white=mostly clear solution, white=particle free solution; bars indicate from left to right: Formulations A, H, E, F, and G (see Table No. 1).

The vials were subjected to a mechanical stress study as described above. The results are shown in FIGS. 19 and 20. With the mechanical stress study, it was shown that particles form even after filtration during storage. However, this process of visible particle formation can be reduced and even stopped by increasing the polysorbate concentration. Based on these results, it was postulated that a Stardust particle-free formulation can be achieved by increasing the polysorbate concentration. Moreover, Stardust particle-free formulations can be achieved using either Polysorbate 20 or Polysorbate 80.

Stability Study: The inclusion of surfactants in protein-containing pharmaceutical formulations is widely known, and common surfactants are Polysorbate 20 and Polysorbate 80. The use of amino acids, such as arginine and methionine, as stabilizers is also known. However, the inventors have observed that for the SAR113244 antibody, particle formation occurs after storage (12 months) only when the primary packaging material consists of glass. To identify stable formulations of SAR113244, pharmaceutically relevant formulations of the antibody were made with concentrations of polysorbate higher than 0.01% and concentrations of an amino acid higher than 50 mM (see Table No. 6 below). These formulations were stored in glass vials or glass syringes and subjected to stability studies under accelerated conditions (at 40° C.) and particle formation was measured (see Table No. 7).

The results of the stability study showed that a high amount of arginine (200 mM) results in a stable, Stardust particle-free formulation for 6 months even if the polysorbate content was at 0.01%. It was desired to achieve even higher concentrations of mAb and to achieve a formulation that is stable for a prolonged period of time. The earlier results showed that a high concentration of arginine in a formulation (Table No. 5) and a high amount of polysorbate (FIGS. 19 and 20) were beneficial. These observations were taken into account, and a new stability study was performed using high amount of arginine and polysorbate.

TABLE NO. 6

| Composition of formulation tested for 6 months. | |
|---|---|
| Sample | Composition |
| SAR113244_14_124A | 150 mg/ml SAR113244, 45 g/L Sucrose, 200 mM Arginine HCl, 2 mg/ml NaCl, 0.1 mg/ml PS20, 10 mM Citrate buffer pH 6.0 |
| SAR113244_14_124B | 150 mg/ml SAR113244, 45 g/L Sucrose, 200 mM Arginine HCl, 0.1 mg/ml PS20, 10 mM Citrate buffer pH 6.0 |
| SAR113244_14_124C | 150 mg/ml SAR113244, 60 g/L Sucrose, 200 mM Arginine HCl, 0.1 mg/ml PS20, 10 mM Citrate buffer pH 6.0 |
| SAR113244_14_124D | 150 mg/ml SAR113244, 90 g/L Sucrose, 200 mM Arginine HCl, 0.1 mg/ml PS20, 10 mM Citrate buffer pH 6.0 |

The samples of Table No. 6 were stored at different temperatures (5° C., 25° C., 40° C. and −20° C.) in 2R ISO vials for 2 weeks (T0.5), 1 month (T1), 3 months (T3), and 6 months (T6) to determine their stability using methods as described in Example No. 1. A control set of samples was also measured at day zero (T0). The results are shown in Table No. 7.

TABLE NO. 7

| Results of stability under accelerated conditions for formulations 124A-D | | | | | |
|---|---|---|---|---|---|
| Sample | SEC [% Monomer] | MFI [particles ≥10 μm] | MFI [particles ≥25 μm] | DLS [nm] | HIAC [particles ≥10 μm] | HIAC [particles ≥25 μm] |
| SAR113244_14_124A T0 | 97.6 | 88 | 0 | 12.21 | 28 | 0 |
| SAR113244_14_124B T0 | 97.6 | 92 | 0 | 12.39 | 5 | 2 |
| SAR113244_14_124C T0 | 97.5 | 153 | 42 | 12.87 | 23 | 5 |
| SAR113244_14_124D T0 | 97.6 | 4 | 0 | 13.99 | 85 | 2 |
| SAR113244_14_124A T0.5 40° C. | 97.5 | | | 12.49 | | |
| SAR113244_14_124B T0.5 40° C. | 97.5 | | | 12.44 | | |
| SAR113244_14_124C T0.5 40° C. | 97.4 | | | 12.92 | | |
| SAR113244_14_124D T0.5 40° C. | 97.5 | | | 13.9 | | |
| SAR113244_14_124A T1 −20° C. | 97.6 | | | 12.18 | 2 | 0 |
| SAR113244_14_124A T1 5° C. | 97.7 | | | 12.24 | 5 | 0 |
| SAR113244_14_124A T1 25° C. | 97.8 | | | 12.12 | 7 | 0 |
| SAR113244_14_124A T1 40° C. | 96.8 | | | 12.41 | 57 | 0 |
| SAR113244_14_124B T1 −20° C. | 97.6 | | | 12.42 | 5 | 0 |
| SAR113244_14_124B T1 5° C. | 97.7 | | | 12.34 | 0 | 0 |
| SAR113244_14_124B T1 25° C. | 97.8 | | | 12.23 | 38 | 0 |
| SAR113244_14_124B T1 40° C. | 96.8 | | | 12.52 | 35 | 2 |

TABLE NO. 7-continued

| | | | | | | |
|---|---|---|---|---|---|---|
| Sample | SEC [% Monomer] | MFI [particles ≥10 μm] | MFI [particles ≥25 μm] | DLS [nm] | HIAC [particles ≥10 μm] | HIAC [particles ≥25 μm] |
| SAR113244_14_124C T1 −20° C. | 97.5 | | | 12.64 | 5 | 0 |
| SAR113244_14_124C T1 5° C. | 97.7 | | | 12.81 | 2 | 0 |
| SAR113244_14_124C T1 25° C. | 97.8 | | | 12.56 | 7 | 0 |
| SAR113244_14_124C T1 40° C. | 96.8 | | | 12.81 | 7 | 0 |
| SAR113244_14_124D T1 −20° C. | 97.6 | | | 13.94 | 10 | 0 |
| SAR113244_14_124D T1 5° C. | 97.6 | | | 13.88 | 10 | 0 |
| SAR113244_14_124D T1 25° C. | 97.8 | | | 13.58 | 2 | 0 |
| SAR113244_14_124D T1 40° C. | 96.9 | | | 13.93 | 12 | 2 |
| SAR113244_14_124A T3 −20° C. | 97.6 | 338 | 54 | 12.25 | 13 | 2 |
| SAR113244_14_124A T3 5° C. | 97.8 | 54 | 3 | 12.12 | 12 | 1 |
| SAR113244_14_124A T3 25° C. | 97.7 | 80 | 14 | 12.33 | 17 | 1 |
| SAR113244_14_124A T3 40° C. | 93.8 | 63 | 0 | 13.28 | 13 | 1 |
| SAR113244_14_124B T3 −20° C. | 97.6 | 101 | 6 | 12.2 | 6 | 1 |
| SAR113244_14_124B T3 5° C. | 97.7 | 17 | 6 | 12.18 | 9 | 1 |
| SAR113244_14_124B T3 25° C. | 97.7 | 195 | 23 | 12.11 | 6 | 1 |
| SAR113244_14_124B T3 40° C. | 94.0 | 109 | 0 | 13.02 | 15 | 0 |
| SAR113244_14_124C T3 −20° C. | 97.6 | 224 | 3 | 12.87 | 5 | 0 |
| SAR113244_14_124C T3 5° C. | 97.7 | 635 | 84 | 12.67 | 10 | 2 |
| SAR113244_14_124C T3 25° C. | 97.7 | 75 | 0 | 12.62 | 7 | 0 |
| SAR113244_14_124C T3 40° C. | 93.9 | 995 | 138 | 13.59 | 6 | 1 |
| SAR113244_14_124D T3 −20° C. | 97.5 | 172 | 14 | 13.98 | 11 | 1 |
| SAR113244_14_124D T3 5° C. | 97.8 | 20 | 3 | 14.45 | 15 | 0 |
| SAR113244_14_124D T3 25° C. | 97.7 | 118 | 6 | 13.45 | 3 | 0 |
| SAR113244_14_124D T3 40° C. | 94.3 | 204 | 29 | 13.7 | 5 | 0 |
| SAR113244_14_124A T6 −80° C. | 97.6 | | | | | |
| SAR113244_14_124A T6 −20° C. | 97.6 | | | | | |
| SAR113244_14_124A T6 5° C. | 97.7 | | | | | |
| SAR113244_14_124A T6 25° C. | 97.5 | | | | | |
| SAR113244_14_124A T6 40° C. | 88.5 | | | | | |
| SAR113244_14_124B T6 −80° C. | 97.5 | | | | | |
| SAR113244_14_124B T6 −20° C. | 97.5 | | | | | |
| SAR113244_14_124B T6 5° C. | 97.7 | | | | | |
| SAR113244_14_124B T6 25° C. | 97.4 | | | | | |
| SAR113244_14_124B T6 40° C. | 88.3 | | | | | |
| SAR113244_14_124C T6 −80° C. | 97.6 | | | | | |
| SAR113244_14_124C T6 −20° C. | 97.6 | | | | | |
| SAR113244_14_124C T6 5° C. | 97.7 | | | | | |
| SAR113244_14_124C T6 25° C. | 97.4 | | | | | |
| SAR113244_14_124C T6 40° C. | 88.4 | | | | | |
| SAR113244_14_124D T6 −80° C. | 97.5 | | | | | |
| SAR113244_14_124D T6 −20° C. | 97.5 | | | | | |
| SAR113244_14_124D T6 5° C. | 97.7 | | | | | |
| SAR113244_14_124D T6 25° C. | 97.5 | | | | | |
| SAR113244_14_124D T6 40° C. | 88.5 | | | | | |

In a subsequent test, new formulations based on Formulation 124D with even higher mAb concentrations were made and tested for stability, as described above. Further, increased polysorbate concentrations were also tested due to the results associated with Table No. 5. The new formulations are described in Table No. 8 below, where Formulations A and B were stored in 2R ISO vials, and Formulations C and D were stored in prefilled syringes (1 mL Hypak BD).

TABLE NO. 8

Composition of formulation put on stability for 6 month.

| Sample | Composition |
|---|---|
| SAR113244_15_133A | 150 mg/ml SAR113244, 45 g/L Sucrose, 200 mM Arginine HCl, 1.0 mg/ml PS80, 10 mM Citrate buffer pH 6.0 |
| SAR113244_15_133B | 175 mg/ml SAR113244, 45 g/L Sucrose, 200 mM Arginine HCl, 1.0 mg/ml PS80, 10 mM Citrate buffer pH 6.0 |
| SAR113244_15_133C | 150 mg/ml SAR113244, 45 g/L Sucrose, 200 mM Arginine HCl, 1.0 mg/ml PS80, 10 mM Citrate buffer pH 6.0 |
| SAR113244_15_133D | 175 mg/ml SAR113244 45 g/L Sucrose, 200 mM Arginine HCl, 1.0 mg/ml PS80, 10 mM Citrate buffer pH 6.0 |

Stability was tested for the formulations of Table No. 8, and the results are shown in Table No. 9.

TABLE NO. 9

| Stability of formulations 133A-D under accelerated conditions. | | | | |
|---|---|---|---|---|
| Sample | SEC [% Monomer] | HIAC [particles ≥ 10 µm] | HIAC [particles ≥ 25 µm] | DLS [nm] |
| SAR113244_15_133A T0 | 98.8 | 10 | 0 | 13.754 |
| SAR113244_15_133B T0 | 98.7 | 5 | 0 | 14.072 |
| SAR113244_15_133C T0 | 98.7 | 140 | 8 | 13.41 |
| SAR113244_15_133D T0 | 98.7 | 18 | 0 | 14.072 |
| SAR113244_15_133A T1 −20° C. | 98.7 | 33 | 2 | 13.084 |
| SAR113244_15_133A T1 5° C. | 98.7 | 3 | 0 | 13.302 |
| SAR113244_15_133A T1 25° C. | 98.7 | 5 | 0 | 13.156 |
| SAR113244_15_133A T1 40° C. | 97.8 | 8 | 0 | 13.452 |
| SAR113244_15_133B T1 −20° C. | 98.4 | 3 | 0 | 13.758 |
| SAR113244_15_133B T1 5° C. | 98.6 | 3 | 0 | 13.774 |
| SAR113244_15_133B T1 25° C. | 98.8 | 20 | 3 | 13.856 |
| SAR113244_15_133B T1 40° C. | 97.8 | 2 | 0 | 14.074 |
| SAR113244_15_133C T1 −20° C. | 98.7 | 288 | 5 | 13.346 |
| SAR113244_15_133C T1 5° C. | 98.8 | 187 | 2 | 13.388 |
| SAR113244_15_133C T1 25° C. | 98.7 | 60 | 3 | 13.424 |
| SAR113244_15_133C T1 40° C. | 97.9 | 77 | 0 | 13.526 |
| SAR113244_15_133D T1 −20° C. | 98.6 | 82 | 3 | 13.878 |
| SAR113244_15_133D T1 5° C. | 98.8 | 218.3 | 2 | 13.818 |
| SAR113244_15_133D T1 25° C. | 98.8 | 373 | 10 | 13.72 |
| SAR113244_15_133D T1 40° C. | 97.7 | 147 | 17 | 14.142 |
| SAR113244_15_133A 2Mo −20° C. | 98.8 | | | 13.49 |
| SAR113244_15_133A 2Mo 5° C. | 98.8 | | | 13.44 |
| SAR113244_15_133A 2Mo 25° C. | 98.8 | | | 13.458 |
| SAR113244_15_133A 2Mo 40° C. | 96.7 | | | 14.044 |
| SAR113244_15_133B 2Mo −20° C. | 98.8 | | | 7.014 |
| SAR113244_15_133B 2Mo 5° C. | 98.8 | | | 13.998 |
| SAR113244_15_133B 2Mo 25° C. | 98.6 | | | 13.906 |
| SAR113244_15_133B 2Mo 40° C. | 96.3 | | | 14.566 |
| SAR113244_15_133A, T3 3Mo −20° C. | 98.8 | 30 | 2 | 13.55 |
| SAR113244_15_133A, T3 3Mo 5° C. | 98.8 | 17 | 0 | 13.6 |
| SAR113244_15_133A, T3 3Mo 25° C. | 98.7 | 5 | 0 | 13.43 |
| SAR113244_15_133A, T3 3Mo 40° C. | 95.0 | 3 | 2 | 13.92 |
| SAR113244_15_133B, T3 3Mo −20° C. | 98.7 | 3 | 0 | 13.96 |
| SAR113244_15_133B, T3 3Mo 5° C. | 98.8 | 7 | 0 | 13.92 |
| SAR113244_15_133B, T3 3Mo 25° C. | 98.7 | 2 | 2 | 13.73 |
| SAR113244_15_133B, T3 3Mo 40° C. | 94.4 | 10 | 0 | 14.54 |
| SAR113244_15_133C, T3 3Mo −20° C. | 98.8 | 197 | 12 | 13.02 |
| SAR113244_15_133C, T3 3Mo 5° C. | 98.8 | 172 | 2 | 13.36 |
| SAR113244_15_133C, T3 3Mo 25° C. | 98.8 | 100 | 2 | 13.47 |
| SAR113244_15_133C, T3 3Mo 40° C. | 95.0 | 73 | 0 | 14.33 |
| SAR113244_15_133D, T3 3Mo −20° C. | 98.7 | 213 | 7 | 13.97 |
| SAR113244_15_133D, T3 3Mo 5° C. | 98.8 | 105 | 3 | 13.87 |
| SAR113244_15_133D, T3 3Mo 25° C. | 98.7 | 52 | 2 | 13.86 |
| SAR113244_15_133D, T3 3Mo 40° C. | 94.4 | 72 | 3 | 14.63 |
| SAR113244_15_133A, T6 6Mo −80° C. | 98.7 | 30 | 10 | 13.54 |
| SAR113244_15_133A, T6 6Mo −20° C. | 98.8 | 62 | 0 | 13.44 |
| SAR113244_15_133A, T6 6Mo +5° C. | 98.8 | 53 | 2 | 13.16 |
| SAR113244_15_133A, T6 6Mo +25° C. | 98.6 | 20 | 5 | 13.27 |
| SAR113244_15_133A, T6 6Mo +40° C. | 89.5 | 7 | 0 | 15.56 |
| SAR113244_15_133B, T6 6Mo −80° C. | 98.6 | 10 | 0 | 14.02 |
| SAR113244_15_133B, T6 6Mo −20° C. | 98.6 | 22 | 0 | 13.91 |
| SAR113244_15_133B, T6 6Mo +5° C. | 98.6 | 7 | 2 | 13.7 |
| SAR113244_15_133B, T6 6Mo +25° C. | 98.4 | 15 | 0 | 13.71 |
| SAR113244_15_133B, T6 6Mo +40° C. | 88.2 | 22 | 3 | 16.26 |
| SAR113244_15_133C, T6 6Mo −80° C. | 98.7 | 75 | 5 | 13.5 |
| SAR113244_15_133C, T6 6Mo −20° C. | 98.8 | 233 | 25 | 13.4 |
| SAR113244_15_133C, T6 6Mo +5° C. | 98.8 | 113 | 12 | 13.38 |
| SAR113244_15_133C, T6 6Mo +25° C. | 98.5 | 218 | 12 | 13.27 |
| SAR113244_15_133C, T6 6Mo +40° C. | 90.0 | 130 | 17 | 15.49 |
| SAR113244_15_133D, T6 6Mo −80° C. | 98.6 | 147 | 5 | 13.9 |
| SAR113244_15_133D, T6 6Mo −20° C. | 98.6 | 85 | 5 | 13.8 |
| SAR113244_15_133D, T6 6Mo +5° C. | 98.7 | 67 | 5 | 13.7 |
| SAR113244_15_133D, T6 6Mo +25° C. | 98.3 | 87 | 0 | 13.84 |
| SAR113244_15_133D, T6 6Mo +40° C. | 88.5 | 67 | 10 | 16.03 |

Based on the results of the stability study, it is shown that the formulation of high antibody concentration, Stardust particle-free preparations was achieved. Indeed, an antibody concentration of up to 175 mg/mL was stable under accelerated conditions (40° C.) for 6 months (see e.g., Formulation B). The amount of particles detected when using prefilled syringes as a primary packaging material was slightly elevated compared to 2R ISO vials, but still well under acceptance criteria of the authorities. To achieve nearly no subvisible particles under the accelerated conditions tested (40° C. for 6 month) with experimental formulations having such high concentrations of a protein prone to aggregation was absolutely unexpected and represents a huge breakthrough in establishing highly stable high concentration antibody formulations. Indeed, such high antibody concentration formulations may allow use of autoinjectors for administration of the antibody formulations. Moreover, such antibody formulations could lead to even greater shelf-life for antibodies stored in glass containers for extended periods of time at high concentrations.

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention. In alternative embodiments, percentages disclosed herein may otherwise vary in amount by ±10, 20, or 30% from values disclosed herein.

```
                          TABLE OF SEQUENCES

SEQ ID NO:  1    MNYPTLEMDLENLEDLFWELDRLDNYNTSLVENHLC

SEQ ID NO:  2    cttccggaattcsargtnmagctgsagsagtc

SEQ ID NO:  3    cttccggaattcsargtnmagctgsagsagtcwgg

SEQ ID NO:  4    ggaggatccatagacagatgggggtgtcgttttggc

SEQ ID NO:  5    ggagctcgayattgtgmtsacmcarwctmca

SEQ ID NO:  6    tatagagctcaagcttggatggtgggaagatggatacagttggtgc

SEQ ID NO:  7    ccaagctgtgtcctrtcc

SEQ ID NO:  8    cgacaagtcgactagcccttgaccaggcatcc

SEQ ID NO:  9    wtctctrgagtcagtggg

SEQ ID NO: 10    cgactagtcgactggtgggaagatggatacag

SEQ ID NO: 11    DIVMTQAAPSVAVTPRESVSISCRSSKSLLHSSGKTYLYWFLQRPGQSPQL
                 LIYRMSNLASGVPDRFSGSGSGTAFTLRISRVEAEDVGVYYCMQHLEYPYT
                 FGGGTKLEIK

SEQ ID NO: 12    QVQLKESGPGLVAPSQSLSITCTVSGFSLIDYGVNWIRQPPGKGLEWLGVI
                 WGDGTTYYNSALKSRLSIRKDNSQSQVFLKMNSLQTDDTAMYYCARIVYWG
                 QGTLVTVSA

SEQ ID NO: 13    DIVMTQSALSVAVTPGESVSISCRSSKSLLHSSGKTYLYWFLQRPGQSPQL
                 LIYRMSNLASGVPDRFSGSGSGTAFTLKISRVEAEDVGVYYCMQHLEYPYT
                 FGGGTKLEIK

SEQ ID NO: 14    DIVMTQSALSVAVTPGESVSISCRSSKSLLHSSGKTYLYWFLQRPGQSPQL
                 LIYRLSNLASGVPDRFSGSGSGTAFTLKISRVEAEDVGVYYCMQHLEYPYT
                 FGGGTKLEIK

SEQ ID NO: 15    DIVMTQSALSVAVTPGESVSISCRSSKSLLHSSGKTYLYWFLQRPGQSPQL
                 LIYRLSSNLASGVPDRFSGSGSGTAFTLKISRVEAEDVGVYYCMQHLEYPY
                 TFGGGTKLEIK

SEQ ID NO: 16    QVQLQESGPGLVAPSESLSITCTVSGFSLIDYGVNWIRQPPGKGLEWLGVI
                 WGDGTTYYNPSLKSRLSISKDNSKSQVFLKMNSLTAADTAMYYCARIVYWG
                 QGTLVTVSS

SEQ ID NO: 17    MGWSCIILFLVATATGVHSDIVMTQSALSVAVTPGESVSISCRSSKSLLHS
                 SGKTYLYWFLQRPGQSPQLLIYRMSNLASGVPDRFSGSGSGTAFTLKISRV
                 EAEDVGVYYCMQHLEYPYTFGGGTKLEIKRTVAAPSVFIFPPSDEQLKSGT
                 ASVVCLLNNFYPREAKVQWKVDNALQSGNSQESVTEQDSKDSTYSLSSTLT
                 LSKADYEKHKVYACEVTHQGLSSPVTKSFNRGEC

SEQ ID NO: 18    gctagcaccatgggctggagctgcatcatcctgttcctggtggccaccgcc
                 accggcgtgcacagcgacatcgtgatgacccagagcgccctcagcgtggcc
                 gtgacccccggcgagagcgtgagcatcagctgccgcagcagcaagagcctg
                 ctgcacagcagcggcaagacctacctgtactggttcctgcagcgccccggc
                 cagagccccagctgctgatctaccgcatgagcaacctggccagcggcgtg
                 cccgaccgcttcagcggcagcggcagcggcaccgccttcaccctgaagatc
                 agccgcgtggaggccgaggacgtgggcgtgtactactgcatgcagcacctg
                 gagtaccccacaccttcggcggcggcaccaagctggagatcaagcgtacg
```

-continued

| TABLE OF SEQUENCES |
|---|

```
gtggccgctccttccgtgttcatcttccctccctccgacgagcagctgaag
tccggcaccgcctccgtggtgtgtctgctgaacaacttctaccctcgggag
gccaaggtgcagtggaaggtggacaacgccctgcagtccggcaactcccag
gagtccgtcaccgagcaggactccaaggacagcacctactccctgtcctcc
accctgaccctgtccaaggccgactacgagaagcacaaggtgtacgcctgt
gaggtgacccaccagggcctgtccagccctgtgaccaagtccttcaaccgg
ggcgagtgctgaagctt
```

SEQ ID NO: 19   MGWSCIILFLVATATGVHSDIVMTQSALSVAVTPGESVSISCRSSKSLLHS
                SGKTYLYWFLQRPGQSPQLLIYRLSNLASGVPDRFSGSGSGTAFTLKISRV
                EAEDVGVYYCMQHLEYPYTFGGGTKLEIKRTVAAPSVFIFPPSDEQLKSGT
                ASVVCLLNNFYPREAKVQWKVDNALQSGNSQESVTEQDSKDSTYSLSSTLT
                LSKADYEKHKVYACEVTHQGLSSPVTKSFNRGEC

SEQ ID NO: 20   gctagcaccatgggctggagctgcatcatcctgttcctggtggccaccgcc
                accggcgtgcacagcgacatcgtgatgacccagagcgccctcagcgtggcc
                gtgacccccggcgagagcgtgagcatcagctgccgcagcagcaagagcctg
                ctgcacagcagcggcaagacctacctgtactggttcctgcagcgccccggc
                cagagcccccagctgctgatctaccgcctgagcaacctggccagcggcgtg
                cccgaccgcttcagcggcagcggcagcggcaccgccttcaccctgaagatc
                agccgcgtggaggccgaggacgtgggcgtgtactactgcatgcagcacctg
                gagtaccctacaccttcggcggcggcaccaagctggagatcaagcgtacg
                gtggccgctccttccgtgttcatcttccctccctccgacgagcagctgaag
                tccggcaccgcctccgtggtgtgtctgctgaacaacttctaccctcgggag
                gccaaggtgcagtggaaggtggacaacgccctgcagtccggcaactcccag
                gagtccgtcaccgagcaggactccaaggacagcacctactccctgtcctcc
                accctgaccctgtccaaggccgactacgagaagcacaaggtgtacgcctgt
                gaggtgacccaccagggcctgtccagccctgtgaccaagtccttcaaccgg
                ggcgagtgctgaagctt SEQ ID NO: 21   MGWSCIILFLVATATGVHSDIVMTQSALSVAVTPGESVSISCRSSKSLLHS
                SGKTYLYWFLQRPGQSPQLLIYRLSSLASGVPDRFSGSGSGTAFTLKISRV
                EAEDVGVYYCMQHLEYPYTFGGGTKLEIKRTVAAPSVFIFPPSDEQLKSGT
                ASVVCLLNNFYPREAKVQWKVDNALQSGNSQESVTEQDSKDSTYSLSSILT
                LSKADYEKHKVYACEVTHQGLSSPVTKSFNRGEC SEQ ID NO: 22   gctagcaccatgggctggagctgcatcatcctgttcctggtggccaccgcc
                accggcgtgcacagcgacatcgtgatgacccagagcgccctcagcgtggcc
                gtgacccccggcgagagcgtgagcatcagctgccgcagcagcaagagcctg
                ctgcacagcagcggcaagacctacctgtactggttcctgcagcgccccggc
                cagagcccccagctgctgatctaccgcctgagcagctggccagcggcgtg
                cccgaccgcttcagcggcagcggcagcggcaccgccttcaccctgaagatc
                agccgcgtggaggccgaggacgtgggcgtgtactactgcatgcagcacctg
                gagtaccctacaccttcggcggcggcaccaagctggagatcaagcgtacg
                gtggccgctccttccgtgttcatcttccctccctccgacgagcagctgaag
                tccggcaccgcctccgtggtgtgtctgctgaacaacttctaccctcgggag
                gccaaggtgcagtggaaggtggacaacgccctgcagtccggcaactcccag
                gagtccgtcaccgagcaggactccaaggacagcacctactccctgtcctcc
                accctgaccctgtccaaggccgactacgagaagcacaaggtgtacgcctgt
                gaggtgacccaccagggcctgtccagccctgtgaccaagtccttcaaccgg
                ggcgagtgctgaagctt SEQ ID NO: 23   MGWSCIILFLVATATGVHSQVQLQESGPGLVAPSESLSITCTVSGFSLIDY
                GVNWIRQPPGKGLEWLGVIWGDGTTYYNPSLKSRLSISKDNSKSQVFLKMN
                SLTAADTAMYYCARIVYWGQGTLVTVSSASTKGPSVFPLAPCSRSTSESTA
                ALGCLVKDYFPEPVTVSWNSGALTSGVHTFPAVLQSSGLYSLSSVVTVPSS
                SLGTKTYTCNVDHKPSNTKVDKRVESKYGPPCPSCPAPEFLGGPSVFLFPP
                KPKDTLMISRTPEVTCVVVDVSQEDPEVQFNWYVDGVEVHNAKTKPREEQF
                NSTYRVVSVLTVLHQDWLNGKEYKCKVSNKGLPSSIEKTISKAKGQPREPQ
                VYTLPPSQEEMTKNQVSLTCLVKGFYPSDIAVEWESNGQPENNYKTTPPVL
                DSDGSFFLYSRLTVDKSRWQEGNVFSCSVMHEALHNHYTQKSLSLSLG SEQ ID NO: 24   gctagcaccatgggctggagctgcatcatcctgttcctggtggccaccgcc
                accggcgtgcacagccaggtgcagctgcaggagagcggccccggcctggtg
                gcccccagcgagagcctgagcatcacctgcaccgtgagcggcttcagcctg
                atcgactacggcgtgaactggatccgccagccccccggcaagggcctggag
                tggctgggcgtgatctggggcgacggcaccacctactacaaccccagcctg
                aagagccgcctgagcatctccaaggacaacagcaagagccaggtgttcctg
                aagatgaacagcctgaccgccgccgacaccgccatgtactactgcgcccgc
                atcgtgtactggggccagggcaccctggtgaccgtgagcagcgccagcacc
                aagggcccttccgtgttccctctggcccccttgctccccggtccacctccgag
                tccaccgccgctctgggctgcctggtgaaggactacttccctgagcctgtg
                accgtgtcctggaactctggcgccctgacctccggcgtgcacaccttccct
                gccgtgctgcagtcctccggcctgtactccctgtcctccgtggtgaccgtg
                ccttcctcctccctgggcaccaagacctacacctgtaacgtggaccacaag
                ccttccaacaccaaggtggacaagcgggtggagtccaagtacggcccttcct
                tgcccttcctgccctgcccctgagttcctgggcggacctagcgtgttcctg
```

-continued

| TABLE OF SEQUENCES |
| --- |

```
ttccctcctaagcctaaggacaccctgatgatctcccggacccctgaggtg
acctgtgtggtggtggacgtgtcccaggaggaccctgaggtccagttcaac
tggtacgtggacggcgtggaggtgcacaacgccaagaccaagcctcgggag
gagcagttcaattccacctaccgggtggtgtctgtgctgaccgtgctgcac
caggactggctgaacggcaaagaatacaagtgtaaggtctccaacaagggc
ctgcccctcctccatcgagaaaaccatctccaaggccaagggccagcctagg
gagcctcaggtgtacaccctgcctcctagccaggaagagatgaccaagaac
caggtgtccctgacctgtctggtgaagggcttctacccttccgacatcgcc
gtggagtgggagtccaacggccagcctgagaacaactacaagaccacccct
cctgtgctggactccgacggctccttcttcctgtactccaggctgaccgtg
gacaagtcccggtggcaggagggcaacgtcttttcctgctccgtgatgcac
gaggccctgcacaaccactacacccagaagtccctgtccctgtctctgggc
tgaagctt
```

SEQ ID NO: 25    KPGQPPRLLIYDASNRATGIPA

SEQ ID NO: 26    TDDTAMYYCARI

SEQ ID NO: 27    SEDSALYYCARD

SEQ ID NO: 28    DIVMTQAAPSVAVTPRESVSISCRSSKSLLHSSGKTYLYWFLQRPGQSPQL
                 LIYRMSNLASGVPDRFSGSGSGTAFTLRISRVEAEDVGVYYCMQHLEYPYT
                 FGGGTKLEIK

SEQ ID NO: 29    QVQLKESGPGLVAPSQSLSITCTVSGFSLIDYGVNWIRQPPGKGLEWLGVI
                 WGDGTTYYNSALKSRLSIRKDNSQSQVFLKMNSLQTDDTAMYYCARIVYWG
                 QGTLVTVSA

SEQ ID NO: 30    DIVMTQAAPSVAVTPGASVSISCRSSKSLLHSSGKTYLYWFLQRPGQSPQL
                 LIYRMSNLASGVPDRFSGSGSGTAFTLRISRVEAEDVGVYYCMQHLEYPYT
                 FGGGTKLEIK

SEQ ID NO: 31    DIVMTQAAPSVAVTPGASVSISCRSSKSLLHSSGKTYLYWFLQRPGQSPQL
                 LIYRLSNLASGVPDRFSGSGSGTAFTLRISRVEAEDVGVYYCMQHLEYPYT
                 FGGGTKLEIK

SEQ ID NO: 32    DIVMTQAAPSVAVTPGASVSISCRSSKSLLHSSGKTYLYWFLQRPGQSPQL
                 LIYRLSSLASGVPDRFSGSGSGTAFTLRISRVEAEDVGVYYCMQHLEYPYT
                 FGGGTKLEIK

SEQ ID NO: 33    QVQLKESGPGLVAPSESLSITCTVSGFSLIDYGVNWIRQPPGKGLEWLGVI
                 WGDGTTYYNPSLKSRLSISKDNSKSQVFLKVISLITDDTAMYYCARIVYWG
                 QGTLVTVSA

SEQ ID NO: 34    EVQLKESGPGLVAPGGSLSITCTVSGFSLIDYGVNWIRQPPGKGLEWLGVI
                 WGDGTTYYNAPLKGRLSISKDNSKSQVFLQMNSLKTDDTAMYYCARIVYWG
                 QGTLVTVSS

SEQ ID NO: 35    MGWSCIILFLVATATGVHSDIVMTQAAPSVAVTPRESVSISCRSSKSLLHS
                 SGKTYLYWFLQRPGQSPQLLIYRMSNLASGVPDRFSGSGSGTAFTLRISRV
                 EAEDVGVYYCMQHLEYPYTFGGGTKLEIKRTVAAPSVFIFPPSDEQLKSGT
                 ASVVCLLNNFYPREAKVQWKVDNALQSGNSQESVTEQDSKDSTYSLSSTLT
                 LSKADYEKHKVYACEVTHQGLSSPVTKSFNRGEC

SEQ ID NO: 36    gctagcaccatgggctggagctgcatcatcctgttcctggtggccaccgcc
                 accggcgtgcacagcgacatcgtgatgacccaggccgcccccagcgtggcc
                 gtgaccccccgcgagagcgtgagcatcagctgccgcagcagcaagagcctg
                 ctgcacagcagcggcaagacctacctgtactggttcctgcagcgccccggc
                 cagagcccccagctgctgatctaccgcatgagcaacctggccagcggcgtg
                 cccgaccgcttcagcggcagcggcagcggcaccgccttcacctgcgcatc
                 agccgcgtggaggccgaggacgtgggcgtgtactactgcatgcagcacctg
                 gagtacccctacccttcggcggcggcaccaagctggagatcaagcgtacg
                 gtggccgctccttccgtgttcatcttccctccctccgacgagcagctgaag
                 tccggcaccgcctccgtggtgtgtctgctgaacaacttctaccctcgggag
                 gccaaggtgcagtggaaggtggacaacgccctgcagtccggcaactcccag
                 gagtccgtcaccgagcaggactccaaggacagcacctactccctgtcctcc
                 accctgaccctgtccaaggccgactacgagaagcacaaggtgtacgcctgt
                 gaggtgacccaccagggcctgtccagccctgtgaccaagtccttcaaccgg
                 ggcgagtgctgaagctt SEQ ID NO: 37    MGWSCIILFLVATATGVHSQVQLKESGPGLVAPSQSLSITCTVSGFSLIDY
                 GVNWIRQPPGKGLEWLGVIWGDGTTYYNSALKSRLSIRKDNSQSQVFLKMN
                 SLQTDDTAMYYCARIVYWGQGTLVTVSAASTKGPSVFPLAPCSRSTSESTA
                 ALGCLVKDYFPEPVTVSWNSGALTSGVHTFPAVLQSSGLYSLSSVVTVPSS
                 SLGTKTYTCNVDHKPSNTKVDKRVESKYGPPCPSCPAPEFLGGPSVFLFPP
                 KPKDTLMISRTPEVTCVVVDVSQEDPEVQFNWYVDGVEVHNAKTKPREEQF
                 NSTYRVVSVLTVLHQDWLNGKEYKCKVSNKGLPSSIEKTISKAKGQPREPQ
```

-continued

TABLE OF SEQUENCES

```
              VYTLPPSQEEMTKNQVSLTCLVKGFYPSDIAVEWESNGQPENNYKTTPPVL
              DSDGSFFLYSRLTVDKSRWQEGNVFSCSVMHEALHNHYTQKSLSLSLG

SEQ ID NO: 38 gctagcaccatgggctggagctgcatcatcctgttcctggtggccaccgcc
              accggcgtgcacagccaggtgcagctgaaggagagcggccccggcctggtg
              gcccccagccagagcctgagcatcacctgcaccgtgagcggcttcagcctg
              atcgactacggcgtgaactggatccgccagccccccggcaagggcctggag
              tggctgggcgtgatctggggcgacggcaccacctactacaacagcgccctg
              aagagccgcctgagcatccgcaaggacaacagccagagccaggtgttcctg
              aagatgaacagcctgcagaccgacgacaccgccatgtactactgcgcccgc
              atcgtgtactggggccagggcaccctggtgaccgtgagcgccgccagcacc
              aagggcccttccgtgttccctctggcccccttgctcccggtccacctccgag
              tccaccgccgctctgggctgcctggtgaaggactacttccctgagcctgtg
              accgtgtcctggaactctggcgccctgacctccggcgtgcacaccttccct
              gccgtgctgcagtcctccggcctgtactccctgtcctccgtggtgaccgtg
              ccttcctcctccctgggcaccaagacctacacctgtaacgtggaccacaag
              ccttccaacaccaaggtggacaagcgggtggagtccaagtacggcccteect
              tgcccttcctgccctgcccctgagttcctgggcggacctagcgtgttcctg
              ttccctcctaagcctaaggacaccctgatgatctcccggacccctgaggtg
              acctgtgtggtggtggacgtgtcccaggaggaccctgaggtccagttcaac
              tggtacgtggacggcgtggaggtgcacaacgccaagaccaagcctcgggag
              gagcagttcaattccacctaccgggtggtgtctgtgctgaccgtgctgcac
              caggactggctgaacggcaaagaatacaagtgtaaggtctccaacaagggc
              ctgccctcctccatcgagaaaaccatctccaaggccaagggccagcctagg
              gagcctcaggtgtacaccctgcctcctagccaggaagagatgaccaagaac
              caggtgtccctgacctgtctggtgaagggcttctacccttccgacatcgcc
              gtggagtgggagtccaacggccagcctgagaacaactacaagaccacccct
              cctgtgctggactccgacggctccttcttcctgtactccaggctgaccgtg
              gacaagtcccggtggcaggagggcaacgtcttttcctgctccgtgatgcac
              gaggccctgcacaaccactacacccagaagtccctgtccctgtctctgggc
              tgaagctt SEQ ID NO: 39 MGWSCIILFLVATATGVHSDIVMTQAAPSVAVTPGASVSISCRSSKSLLHS
              SGKTYLYWFLQRPGQSPQLLIYRMSNLASGVPDRFSGSGSGTAFTLRISRV
              EAEDVGVYYCMQHLEYPYTFGGGTKLEIKRTVAAPSVFIFPPSDEQLKSGT
              ASVVCLLNNFYPREAKVQWKVDNALQSGNSQESVTEQDSKDSTYSLSSTLT
              LSKADYEKHKVYACEVTHQGLSSPVTKSFNRGEC SEQ ID NO: 40 gctagcaccatgggctggagctgcatcatcctgttcctggtggccaccgcc
              accggcgtgcacagcgacatcgtgatgacccaggccgcccccagcgtggcc
              gtgaccccccggcgccagcgtgagcatcagctgccgcagcagcaagagcctg
              ctgcacagcagcggcaagacctacctgtactggttcctgcagcgccccggc
              cagagccccagctgctgatctaccgcatgagcaacctggccagcggcgtg
              cccgaccgcttcagcggcagcggcagcggcaccgccttcaccctgcgcatc
              agccgcgtggaggccgaggacgtgggcgtgtactactgcatgcagcacctg
              gagtaccccta cacccttcggcggcggcaccaagctggagatcaagcgtacg
              gtggccgctccttccgtgttcatcttccctccctccgacgagcagctgaag
              tccggcaccgcctccgtggtgtgtctgctgaacaacttctaccctcgggag
              gccaaggtgcagtggaaggtggacaacgccctgcagtccggcaactcccag
              gagtccgtcaccgagcaggactccaaggacagcacctactccctgtcctcc
              accctgaccctgtccaaggccgactacgagaagcacaaggtgtacgcctgt
              gaggtgacccaccagggcctgtccagccctgtgaccaagtccttcaaccgg
              ggcgagtgctgaagctt SEQ ID NO: 41 MGWSCIILFLVATATGVHSDIVMTQAAPSVAVTPGASVSISCRSSKSLLHS
              SGKTYLYWFLQRPGQSPQLLIYRLSNLASGVPDRFSGSGSGTAFTLRISRV
              EAEDVGVYYCMQHLEYPYTFGGGTKLEIKRTVAAPSVFIFPPSDEQLKSGT
              ASVVCLLNNFYPREAKVQWKVDNALQSGNSQESVTEQDSKDSTYSLSSTLT
              LSKADYEKHKVYACEVTHQGLSSPVTKSFNRGEC SEQ ID NO: 42 gctagcaccatgggctggagctgcatcatcctgttcctggtggccaccgcc
              accggcgtgcacagcgacatcgtgatgacccaggccgcccccagcgtggcc
              gtgaccccccggcgccagcgtgagcatcagctgccgcagcagcaagagcctg
              ctgcacagcagcggcaagacctacctgtactggttcctgcagcgccccggc
              cagagccccagctgctgatctaccgcctgagcaacctggccagcggcgtg
              cccgaccgcttcagcggcagcggcagcggcaccgccttcaccctgcgcatc
              agccgcgtggaggccgaggacgtgggcgtgtactactgcatgcagcacctg
              gagtacccctacacccttcggcggcggcaccaagctggagatcaagcgtacg
              gtggccgctccttccgtgttcatcttccctccctccgacgagcagctgaag
              tccggcaccgcctccgtggtgtgtctgctgaacaacttctaccctcgggag
              gccaaggtgcagtggaaggtggacaacgccctgcagtccggcaactcccag
              gagtccgtcaccgagcaggactccaaggacagcacctactccctgtcctcc
              accctgaccctgtccaaggccgactacgagaagcacaaggtgtacgcctgt
              gaggtgacccaccagggcctgtccagccctgtgaccaagtccttcaaccgg
              ggcgagtgctgaagctt
```

-continued

| TABLE OF SEQUENCES |
|---|

SEQ ID NO: 43   MGWSCIILFLVATATGVHSDIVMTQAAPSVAVTPGASVSISCRSSKSLLHS
SGKTYLYWFLQRPGQSPQLLIYRLSSLASGVPDRFSGSGSGTAFTLRISRV
EAEDVGVYYCMQHLEYPYTFGGGTKLEIKRTVAAPSVFIFPPSDEQLKSGT
ASVVCLLNNFYPREAKVQWKVDNALQSGNSQESVTEQDSKDSTYSLSSTLT
LSKADYEKHKVYACEVTHQGLSSPVTKSFNRGEC

SEQ ID NO: 44   gctagcaccatgggctggagctgcatcatcctgttcctggtggccaccgcc
accggcgtgcacagcgacatcgtgatgacccaggccgcccccagcgtggcc
gtgacccccggcgcgcagcgtgagcatcagctgccgcagcagcaagagcctg
ctgcacagcagcggcaagacctacctgtactggttcctgcagcgccccggc
cagagcccccagctgctgatctaccgcctgagcagcctggccagcggcgtg
cccgaccgcttcagcggcagcggcagcggcaccgccttcacectgcgcatc
agccgcgtggaggccgaggacgtgggcgtgtactactgcatgcagcacctg
gagtaccctacaaccttcggcggcggcaccaagctggagatcaagcgtacg
gtggccgctccttccgtgttcatcttccctccctccgacgagcagctgaag
tccggcaccgcctccgtggtgtgtctgctgaacaacttctaccctcgggag
gccaaggtgcagtggaaggtggacaacgccctgcagtccggcaactcccag
gagtccgtcaccgagcaggactccaaggacagcacctactccctgtcctcc
accctgaccctgtccaaggccgactacgagaagcacaaggtgtacgcctgt
gaggtgacccaccagggcctgtccagccctgtgaccaagtccttcaaccgg
ggcgagtgctgaagctt SEQ ID NO: 45   MGWSCIILFLVATATGVHSQVQLKESGPGLVAPSESLSITCTVSGFSLIDY
GVNWIRQPPGKGLEWLGVIWGDGTTYYNPSLKSRLSISKDNSKSQVFLKVT
SLTTDDTAMYYCARIVYWGQGTLVTVSAASTKGPSVFPLAPCSRSTSESTA
ALGCLVKDYFPEPVTVSWNSGALTSGVHTFPAVLQSSGLYSLSSVVTVPSS
SLGTKTYTCNVDHKPSNTKVDKRVESKYGPPCPSCPAPEFLGGPSVFLFPP
KPKDTLMISRTPEVTCVVVDVSQEDPEVQFNWYVDGVEVHNAKTKPREEQF
NSTYRVVSVLTVLHQDWLNGKEYKCKVSNKGLPSSIEKTISKAKGQPREPQ
VYTLPPSQEEMTKNQVSLTCLVKGFYPSDIAVEWESNGQPENNYKTTPPVL
DSDGSFFLYSRLTVDKSRWQEGNVFSCSVMHEALHNHYTQKSLSLSLG SEQ ID NO: 46   gctagcaccatgggctggagctgcatcatcctgttcctggtggccaccgcc
accggcgtgcacagccaggtgcagctgaaggagagcggccccggcctggtg
gcccccagcgagagcctgagcatcacctgcaccgtgagcggcttcagcctg
atcgactacggcgtgaactggatccgccagcccccgcaagggcctggag
tggctgggcgtgatctgggcgacggcaccacctactacaaccccagcctg
aagagccgcctgagcatcagcaaggacaacagcaagagccaggtgttcctg
aaggtgaccagcctgaccaccgacgacaccgccatgtactactgcgcccgc
atcgtgtactggggccagggcaccctggtgaccgtgagcgccgccagcacc
aagggcccttccgtgttccctctggcccccttgctcccggtccacctccgag
tccaccgccgctctgggctgcctggtgaaggactacttccctgagcctgtg
accgtgtcctggaactctggcgccctgacctccggcgtgcacaccttccct
gccgtgctgcagtcctccggcctgtactcctgtcctccgtggtgaccgtg
ccttcctcctcctctgggcaccaagacctacacctgtaacgtggaccacaag
ccttccaacaccaaggtggacaagcgggtggagtccaagtacggccctcct
tgcccttcctgccctgcccctgagttcctgggcggacctagcgtgttcctg
ttccctcctaagcctaaggacaccctgatgatctcccggacccctgaggtg
acctgtgtggtggtggacgtgtcccaggaggaccctgaggtccagttcaac
tggtacgtggacggcgtggaggtgcacaacgccaagaccaagcctcgggag
gagcagttcaattccacctaccgggtggtgtctgtgctgaccgtgctgcac
caggactggctgaacggcaaagaatacaagtgtaaggtctccaacaagggc
ctgccctcctccatcgagaaaaccatctccaaggccaagggccagcctagg
gagcctcaggtgtacaccctgcctcctagccaggaagagatgaccaagaac
caggtgtccctgacctgtctggtgaagggcttctaccttccgcacatcgcc
gtggagtgggagtccaacggccagcctgagaacaactacaagaccacccct
cctgtgctggactccgacggctccttcttcctgtactccaggctgaccgtg
gacaagtcccggtggcaggagggcaacgtcttttcctgctccgtgtctgcac
gaggcccctgcacaaccactacacccagaagtccctgtccctgtctctgggc
tgaagctt SEQ ID NO: 47   MGWSCIILFLVATATGVHSEVQLKESGPGLVAPGGSLSITCTVSGFSLIDY
GVNWIRQPPGKGLEWLGVIWGDGTTYYNAPLKGRLSISKDNSKSQVFLQMN
SLKTDDTAMYYCARIVYWGQGTLVTVSSASTKGPSVFPLAPCSRSTSESTA
ALGCLVKDYFPEPVTVSWNSGALTSGVHTFPAVLQSSGLYSLSSVVTVPSS
SLGTKTYTCNVDHKPSNTKVDKRVESKYGPPCPSCPAPEFLGGPSVFLFPP
KPKDTLMISRTPEVTCVVVDVSQEDPEVQFNWYVDGVEVHNAKTKPREEQF
NSTYRVVSVLTVLHQDWLNGKEYKCKVSNKGLPSSIEKTISKAKGQPREPQ
VYTLPPSQEEMTKNQVSLTCLVKGFYPSDIAVEWESNGQPENNYKTTPPVL
DSDGSFFLYSRLTVDKSRWQEGNVFSCSVMHEALHNHYTQKSLSLSLG SEQ ID NO: 48   gctagcaccatgggctggagctgcatcatcctgttcctggtggccaccgcc
accggcgtgcacagcgaggtgcagctgaaggagagcggccccggcctggtg
gcccccggcggcagcctgagcatcacctgcaccgtgagcggcttcagcctg
atcgactacggcgtgaactggatccgccagcccccgcaagggcctggag
tggctgggcgtgatctgggcgacggcaccacctactacaacgcccccctg
aagggcccgcctgagcatcagcaaggacaacagcaagagccaggtgttcctg

TABLE OF SEQUENCES

```
                    cagatgaacagcctgaagaccgacgacaccgccatgtactactgcgcccgc
                    atcgtgtactggggccagggcaccctggtgaccgtgagcagcgccagcacc
                    aagggcccttccgtgttccctctggccccttgctcccggtccacctccgag
                    tccaccgccgctctgggctgcctggtgaaggactacttccctgagcctgtg
                    accgtgtcctggaactctggcgccctgacctccggcgtgcacaccttccct
                    gccgtgctgcagtcctccggcctgtactccctgtcctccgtggtgaccgtg
                    ccttcctcctccctgggcaccaagacctacacctgtaacgtggaccacaag
                    ccttccaacaccaaggtggacaagcgggtggagtccaagtacggccctcct
                    tgcccttcctgccctgccctgagttcctgggcggacctagcgtgttcctg
                    ttccctcctaagcctaaggacaccctgatgatctcccggacccctgaggtg
                    acctgtgtggtggtggacgtgtcccaggaggaccctgaggtccagttcaac
                    tggtacgtggacggcgtggaggtgcacaacgccaagaccaagcctcgggag
                    gagcagttcaattccacctaccgggtggtgtctgtgctgaccgtgctgcac
                    caggactggctgaacggcaaagaatacaagtgtaaggtctccaacaagggc
                    ctgccctcctccatcgagaaaaccatctccaaggccaagggccagcctagg
                    gagcctcaggtgtacaccctgcctcctagccaggaagagatgaccaagaac
                    caggtgtccctgacctgtctggtgaagggcttctaccttccgacatcgcc
                    gtggagtgggagtccaacggccagcctgagaacaactacaagaccacccct
                    cctgtgctggactccgacggctccttcttcctgtactccaggctgaccgtg
                    gacaagtcccggtggcaggagggcaacgtcttttcctgctccgtgatgcac
                    gaggccctgcacaaccactacacccagaagtccctgtccctgtctctgggc
                    tgaagctt
```

SEQ ID NO: 49    ELLGG

SEQ ID NO: 50    MISRT

SEQ ID NO: 51    HHHHHH

SEQ ID NO: 52    PGKAPQLLIYRMSNL

SEQ ID NO: 53    PGKAPKLLIYAASSL

SEQ ID NO: 54    SLIDYGVNWIRQPPG

SEQ ID NO: 55    DIVMTQAAPSVAVTPGQSVSISCRSSKSLLHSSGKTYLYWFLQHPGKAPQL
                     LIYRMSNLASGVPDRFSGSGSGTAFTLTISGVQAEDVGVYYCMQHLEYPYT
                     FGGGTKLEIK

SEQ ID NO: 56    QVQLQESGPGLVAPSQSLSITCTVSGFSLIDYGVNWIRQPPGKGLEWLGVI
                     WGDGTTYYNSALKSRLSISKDTSKSQVFLKMNSLTTDDTAMYYCARIVYWG
                     QGTLVTVSAAK

SEQ ID NO: 57    QVQLQESGPGLVAPSQSLSITCTVSGFSLIDYGVNWIRQPPGKGLEWLGVI
                     WGDGTTYYPSALKSRLSISKDTSKSQVFLKMNSLTTDDTAMYYCARIVYWG
                     QGTLVTVSAAK

SEQ ID NO: 58    RSSKSLLHSSGKTYLY

SEQ ID NO: 59    RMSNLAS

SEQ ID NO: 60    MQHLEYPYT

SEQ ID NO: 61    GFSLIDYGVN

SEQ ID NO: 62    VIWGDGTTY

SEQ ID NO: 63    IVY

SEQ ID NO: 64    RLSNLAS

SEQ ID NO: 65    RLSSNLAS

SEQ ID NO: 66    RMSNLA

SEQ ID NO: 67    RLSNLA

SEQ ID NO: 68    RLSSLA

SEQ ID NO: 69    RSSKSLLHSSGKTYLYW

What is claimed is:

1. A method of treating rheumatoid arthritis in a subject in need thereof, comprising:

administering to a subject in need thereof an antibody formulation comprising a) about 100 to about 175 mg/mL of a CXCR5 antibody or a fragment that binds CXCR5;

b) about 10 mM citrate buffer;

c) about 0.1% (w/v) surfactant;

d) about 200 mM arginine; and e) up to 10% sucrose, wherein the pH of the formulation is about pH 6, wherein the antibody is a fully human anti-CXCR5 antibody, and wherein the antibody comprises a heavy chain comprising the amino acid sequence of SEQ ID NO: 33 and a light chain comprising the amino acid sequence of SEQ ID NO: 32.

2. The method of claim 1, wherein the antibody comprises a single chain Fv.

3. The method of claim 1, wherein the antibody is an isolated antibody or antigen-binding fragment thereof that specifically binds to the extracellular domain of human CXCR5.

4. The method of claim 3, wherein the isolated antibody or antigen-binding fragment thereof comprises the amino acid sequences of RSSKSLLHSSGKTYLY (SEQ ID NO: 58), RLSSLA (SEQ ID NO: 68), MQHLEYPYT (SEQ ID NO: 60), GFSLIDYGVN (SEQ ID NO: 61), VIWGDGTTY (SEQ ID NO: 62), and IVY (SEQ ID NO: 63).

5. The method of claim 1, wherein the surfactant is a polysorbate.

6. The method of claim 5, wherein the polysorbate is polysorbate 20 or polysorbate 80.

7. The method of claim 1 further comprising reducing a sign or symptom of the CXCR5-mediated disease or disorder.

8. The method of claim 1, wherein the formulation is administered mucosally, intravenously, intradermally, subcutaneously, or intramuscularly.

9. A method of treating rheumatoid arthritis in a subject in need thereof, comprising:

administering to a subject in need thereof an antibody formulation comprising a) about 175 mg/mL of a humanized IgG4 anti-CXCR5 antibody or a fragment that binds CXCR5;

b) about 10 mM citrate buffer;

c) about 1.0 mg/mL polysorbate 80;

d) about 200 mM arginine HCl; and e) about 45 mg/mL sucrose, wherein the pH of the formulation is about pH 6, wherein the humanized IgG4 anti-CXCR5 antibody comprises a heavy chain comprising the amino acid sequence of SEQ ID NO: 33 and a light chain comprising the amino acid sequence of SEQ ID NO: 32.

10. The method of claim 9, wherein the antibody comprises a single chain Fv.

11. The method of claim 9, wherein the antibody is an isolated antibody or antigen-binding fragment thereof that specifically binds to the extracellular domain of human CXCR5.

12. The method of claim 11, wherein the isolated antibody or antigen-binding fragment thereof comprises the amino acid sequences of RSSKSLLHSSGKTYLY (SEQ ID NO: 58), RLSSLA (SEQ ID NO: 68), MQHLEYPYT (SEQ ID NO: 60), GFSLIDYGVN (SEQ ID NO: 61), VIWGDGTTY (SEQ ID NO: 62), and IVY (SEQ ID NO: 63).

13. The method of claim 9, wherein the formulation is administered mucosally, intravenously, intradermally, subcutaneously, or intramuscularly.

* * * * *

SEQUENCE LISTING

<160> NUMBER OF SEQ ID NOS: 69

<210> SEQ ID NO 1
<211> LENGTH: 36
<212> TYPE: PRT
<213> ORGANISM: Homo sapiens

<400> SEQUENCE: 1

Met Asn Tyr Pro Thr Leu Glu Met Asp Leu Glu Asn Leu Glu Asp Leu
1               5                   10                  15

Phe Trp Glu Leu Asp Arg Leu Asp Asn Tyr Asn Thr Ser Leu Val Glu
            20                  25                  30

Asn His Leu Cys
        35

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: misc_feature
<222> LOCATION: (18)..(18)
<223> OTHER INFORMATION: n is a, c, g, or t

<400> SEQUENCE: 2
cttccggaat tcsargtnma gctgsagsag tc                                    32

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: misc_feature
<222> LOCATION: (18)..(18)
<223> OTHER INFORMATION: n is a, c, g, or t

<400> SEQUENCE: 3
cttccggaat tcsargtnma gctgsagsag tcwgg                                 35

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggaggatcca tagacagatg ggggtgtcgt tttggc                                36

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggagctcgay attgtgmtsa cmcarwctmc a                                     31

-continued

```
<210> SEQ ID NO 6
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tatagagctc aagcttggat ggtgggaaga tggatacagt tggtgc                   46

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ccaagctgtg tcctrtcc                                                  18

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cgacaagtcg actagccctt gaccaggcat cc                                  32

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
wtctctrgag tcagtggg                                                  18

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cgactagtcg actggtggga agatggatac ag                                  32

<210> SEQ ID NO 11
<211> LENGTH: 112
<212> TYPE: PRT
<213> ORGANISM: Mus sp.

<400> SEQUENCE: 11

Asp Ile Val Met Thr Gln Ala Ala Pro Ser Val Ala Val Thr Pro Arg
1               5                   10                  15

Glu Ser Val Ser Ile Ser Cys Arg Ser Ser Lys Ser Leu Leu His Ser
            20                  25                  30
```

-continued

```
Ser Gly Lys Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Leu Glu Ile Lys
            100                 105                 110
```

```
<210> SEQ ID NO 12
<211> LENGTH: 111
<212> TYPE: PRT
<213> ORGANISM: Mus sp.

<400> SEQUENCE: 12

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ile Asp Tyr
            20                  25                  30

Gly Val Asn Trp Ile Arg Gln Pro Pro Gly Lys Gly Leu Glu Trp Leu
        35                  40                  45

Gly Val Ile Trp Gly Asp Gly Thr Thr Tyr Tyr Asn Ser Ala Leu Lys
    50                  55                  60

Ser Arg Leu Ser Ile Arg Lys Asp Asn Ser Gln Ser Gln Val Phe Leu
65                  70                  75                  80

Lys Met Asn Ser Leu Gln Thr Asp Asp Thr Ala Met Tyr Tyr Cys Ala
                85                  90                  95

Arg Ile Val Tyr Trp Gly Gln Gly Thr Leu Val Thr Val Ser Ala
            100                 105                 110
```

```
<210> SEQ ID NO 13
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Ile Val Met Thr Gln Ser Ala Leu Ser Val Ala Val Thr Pro Gly
1               5                   10                  15

Glu Ser Val Ser Ile Ser Cys Arg Ser Ser Lys Ser Leu Leu His Ser
            20                  25                  30

Ser Gly Lys Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Leu Glu Ile Lys
            100                 105                 110
```

```
<210> SEQ ID NO 14
<211> LENGTH: 112
```

-continued

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ile Val Met Thr Gln Ser Ala Leu Ser Val Ala Val Thr Pro Gly
1               5                   10                  15

Glu Ser Val Ser Ile Ser Cys Arg Ser Ser Lys Ser Leu Leu His Ser
                20                  25                  30

Ser Gly Lys Thr Tyr Leu Tyr Trp Phe Leu Gln Arg Pro Gly Gln Ser
            35                  40                  45

Pro Gln Leu Leu Ile Tyr Arg Leu Ser Asn Leu Ala Ser Gly Val Pro
        50                  55                  60

Asp Arg Phe Ser Gly Ser Gly Ser Gly Thr Ala Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Leu Glu Ile Lys
            100                 105                 110

<210> SEQ ID NO 15
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Asp Ile Val Met Thr Gln Ser Ala Leu Ser Val Ala Val Thr Pro Gly
1               5                   10                  15

Glu Ser Val Ser Ile Ser Cys Arg Ser Ser Lys Ser Leu Leu His Ser
                20                  25                  30

Ser Gly Lys Thr Tyr Leu Tyr Trp Phe Leu Gln Arg Pro Gly Gln Ser
            35                  40                  45

Pro Gln Leu Leu Ile Tyr Arg Leu Ser Ser Asn Leu Ala Ser Gly Val
        50                  55                  60

Pro Asp Arg Phe Ser Gly Ser Gly Ser Gly Thr Ala Phe Thr Leu Lys
65                  70                  75                  80

Ile Ser Arg Val Glu Ala Glu Asp Val Gly Val Tyr Tyr Cys Met Gln
                85                  90                  95

His Leu Glu Tyr Pro Tyr Thr Phe Gly Gly Gly Thr Lys Leu Glu Ile
            100                 105                 110

Lys

<210> SEQ ID NO 16
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Gln Glu Ser Gly Pro Gly Leu Val Ala Pro Ser Glu
1               5                   10                  15

Ser Leu Ser Ile Thr Cys Thr Val Ser Gly Phe Ser Leu Ile Asp Tyr
                20                  25                  30
```

-continued

```
Gly Val Asn Trp Ile Arg Gln Pro Pro Gly Lys Gly Leu Glu Trp Leu
        35                  40                  45

Gly Val Ile Trp Gly Asp Gly Thr Thr Tyr Tyr Asn Pro Ser Leu Lys
        50                  55                  60

Ser Arg Leu Ser Ile Ser Lys Asp Asn Ser Lys Ser Gln Val Phe Leu
65                  70                  75                  80

Lys Met Asn Ser Leu Thr Ala Ala Asp Thr Ala Met Tyr Tyr Cys Ala
                85                  90                  95

Arg Ile Val Tyr Trp Gly Gln Gly Thr Leu Val Thr Val Ser Ser
                100                 105                 110

<210> SEQ ID NO 17
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Gly Trp Ser Cys Ile Ile Leu Phe Leu Val Ala Thr Ala Thr Gly
1                5                   10                  15

Val His Ser Asp Ile Val Met Thr Gln Ser Ala Leu Ser Val Ala Val
                20                  25                  30

Thr Pro Gly Glu Ser Val Ser Ile Ser Cys Arg Ser Ser Lys Ser Leu
        35                  40                  45

Leu His Ser Ser Gly Lys Thr Tyr Leu Tyr Trp Phe Leu Gln Arg Pro
        50                  55                  60

Gly Gln Ser Pro Gln Leu Leu Ile Tyr Arg Met Ser Asn Leu Ala Ser
65                  70                  75                  80

Gly Val Pro Asp Arg Phe Ser Gly Ser Gly Ser Gly Thr Ala Phe Thr
                85                  90                  95

Leu Lys Ile Ser Arg Val Glu Ala Glu Asp Val Gly Val Tyr Tyr Cys
                100                 105                 110

Met Gln His Leu Glu Tyr Pro Tyr Thr Phe Gly Gly Gly Thr Lys Leu
                115                 120                 125

Glu Ile Lys Arg Thr Val Ala Ala Pro Ser Val Phe Ile Phe Pro Pro
        130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
                180                 185                 190

Lys Asp Ser Thr Tyr Ser Leu Ser Ser Thr Leu Thr Leu Ser Lys Ala
                195                 200                 205

Asp Tyr Glu Lys His Lys Val Tyr Ala Cys Glu Val Thr His Gln Gly
        210                 215                 220

Leu Ser Ser Pro Val Thr Lys Ser Phe Asn Arg Gly Glu Cys
225                 230                 235

<210> SEQ ID NO 18
<211> LENGTH: 731
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 18

```
gctagcacca tgggctggag ctgcatcatc ctgttcctgg tggccaccgc caccggcgtg      60
cacagcgaca tcgtgatgac ccagagcgcc ctcagcgtgg ccgtgacccc cggcgagagc     120
gtgagcatca gctgccgcag cagcaagagc ctgctgcaca gcagcggcaa gacctacctg     180
tactggttcc tgcagcgccc cggccagagc ccccagctgc tgatctaccg catgagcaac     240
ctggccagcg gcgtgcccga ccgcttcagc ggcagcggca gcggcaccgc cttcaccctg     300
aagatcagcc gcgtggaggc cgaggacgtg ggcgtgtact actgcatgca gcacctggag     360 taccctaca ccttcggcgg cggcaccaag ctggagatca gcgtacggt ggccgctcct     420 tccgtgttca tcttccctcc ctccgacgag cagctgaagt ccggcaccgc ctccgtggtg     480
tgtctgctga acaacttcta ccctcgggag gccaaggtgc agtggaaggt ggacaacgcc     540
ctgcagtccg gcaactccca ggagtccgtc accgagcagg actccaagga cagcacctac     600
tccctgtcct ccaccctgac cctgtccaag gccgactacg agaagcacaa ggtgtacgcc     660
tgtgaggtga cccaccaggg cctgtccagc cctgtgacca agtccttcaa ccggggcgag     720
tgctgaagct t                                                         731
```

<210> SEQ ID NO 19
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Met Gly Trp Ser Cys Ile Ile Leu Phe Leu Val Ala Thr Ala Thr Gly
1               5                   10                  15

Val His Ser Asp Ile Val Met Thr Gln Ser Ala Leu Ser Val Ala Val
            20                  25                  30

Thr Pro Gly Glu Ser Val Ser Ile Ser Cys Arg Ser Ser Lys Ser Leu
        35                  40                  45

Leu His Ser Ser Gly Lys Thr Tyr Leu Tyr Trp Phe Leu Gln Arg Pro
    50                  55                  60

Gly Gln Ser Pro Gln Leu Leu Ile Tyr Arg Leu Ser Asn Leu Ala Ser
65                  70                  75                  80

Gly Val Pro Asp Arg Phe Ser Gly Ser Gly Ser Gly Thr Ala Phe Thr
                85                  90                  95

Leu Lys Ile Ser Arg Val Glu Ala Glu Asp Val Gly Val Tyr Tyr Cys
            100                 105                 110

Met Gln His Leu Glu Tyr Pro Tyr Thr Phe Gly Gly Gly Thr Lys Leu
            115                 120                 125

Glu Ile Lys Arg Thr Val Ala Ala Pro Ser Val Phe Ile Phe Pro Pro
        130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
            195                 200                 205
```

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 20
<211> LENGTH: 731
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
gctagcacca tgggctggag ctgcatcatc ctgttcctgg tggccaccgc caccggcgtg        60
cacagcgaca tcgtgatgac ccagagcgcc ctcagcgtgg ccgtgacccc cggcgagagc       120
gtgagcatca gctgccgcag cagcaagagc ctgctgcaca gcagcggcaa gacctacctg       180
tactggttcc tgcagcgccc cggccagagc ccccagctgc tgatctaccg cctgagcaac       240
ctggccagcg gcgtgcccga ccgcttcagc ggcagcggca gcggcaccgc cttcaccctg       300
aagatcagcc gcgtggaggc cgaggacgtg ggcgtgtact actgcatgca gcacctggag       360
tacccctaca ccttcggcgg cggcaccaag ctggagatca gcgtacggt ggccgctcct        420 tccgtgttca tcttccctcc ctccgacgag cagctgaagt ccggcaccgc ctccgtggtg       480
tgtctgctga caacttcta ccctcgggag gccaaggtgc agtggaaggt ggacaacgcc        540
ctgcagtccg gcaactccca ggagtccgtc accgagcagg actccaagga cagcacctac       600
tccctgtcct ccaccctgac cctgtccaag gccgactacg agaagcacaa ggtgtacgcc       660
tgtgaggtga cccaccaggg cctgtccagc cctgtgacca gtccttcaa ccggggcgag        720 tgctgaagct t                                                           731

<210> SEQ ID NO 21
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Gly Trp Ser Cys Ile Ile Leu Phe Leu Val Ala Thr Ala Thr Gly
1               5                   10                  15

Val His Ser Asp Ile Val Met Thr Gln Ser Ala Leu Ser Val Ala Val
                20                  25                  30

Thr Pro Gly Glu Ser Val Ser Ile Ser Cys Arg Ser Ser Lys Ser Leu
        35                  40                  45

Leu His Ser Ser Gly Lys Thr Tyr Leu Tyr Trp Phe Leu Gln Arg Pro
    50                  55                  60

Gly Gln Ser Pro Gln Leu Leu Ile Tyr Arg Leu Ser Ser Leu Ala Ser
65                  70                  75                  80

Gly Val Pro Asp Arg Phe Ser Gly Ser Gly Ser Gly Thr Ala Phe Thr
                85                  90                  95

Leu Lys Ile Ser Arg Val Glu Ala Glu Asp Val Gly Val Tyr Tyr Cys
            100                 105                 110

Met Gln His Leu Glu Tyr Pro Tyr Thr Phe Gly Gly Gly Thr Lys Leu
        115                 120                 125

-continued

```
Glu Ile Lys Arg Thr Val Ala Ala Pro Ser Val Phe Ile Phe Pro Pro
    130             135             140

Ser Asp Glu Gln Leu Lys Ser Gly Thr Ala Ser Val Val Cys Leu Leu
145             150             155             160

Asn Asn Phe Tyr Pro Arg Glu Ala Lys Val Gln Trp Lys Val Asp Asn
            165             170             175

Ala Leu Gln Ser Gly Asn Ser Gln Glu Ser Val Thr Glu Gln Asp Ser
            180             185             190

Lys Asp Ser Thr Tyr Ser Leu Ser Ser Thr Leu Thr Leu Ser Lys Ala
        195             200             205

Asp Tyr Glu Lys His Lys Val Tyr Ala Cys Glu Val Thr His Gln Gly
    210             215             220

Leu Ser Ser Pro Val Thr Lys Ser Phe Asn Arg Gly Glu Cys
225             230             235
```

```
<210> SEQ ID NO 22
<211> LENGTH: 731
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
gctagcacca tgggctggag ctgcatcatc ctgttcctgg tggccaccgc caccggcgtg      60
cacagcgaca tcgtgatgac ccagagcgcc ctcagcgtgg ccgtgacccc cggcgagagc     120
gtgagcatca gctgccgcag cagcaagagc ctgctgcaca gcagcggcaa gacctacctg     180
tactggttcc tgcagcgccc cggccagagc ccccagctgc tgatctaccg cctgagcagc     240
ctggccagcg gcgtgcccga ccgcttcagc ggcagcggca gcggcaccgc cttcaccctg     300
aagatcagcc gcgtggaggc cgaggacgtg ggcgtgtact actgcatgca gcacctggag     360
tacccctaca ccttcggcgg cggcaccaag ctggagatca gcgtacggt ggccgctcct      420 tccgtgttca tcttccctcc ctccgacgag cagctgaagt ccggcaccgc ctccgtggtg     480
tgtctgctga caacttcta ccctcgggag gccaaggtgc agtggaaggt ggacaacgcc      540
ctgcagtccg gcaactccca ggagtccgtc accgagcagg actccaagga cagcacctac     600
tccctgtcct ccaccctgac cctgtccaag gccgactacg agaagcacaa ggtgtacgcc     660
tgtgaggtga cccaccaggg cctgtccagc cctgtgacca gtccttcaa ccggggcgag      720 tgctgaagct t                                                          731
```

```
<210> SEQ ID NO 23
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Gly Trp Ser Cys Ile Ile Leu Phe Leu Val Ala Thr Ala Thr Gly
1               5               10              15

Val His Ser Gln Val Gln Leu Gln Glu Ser Gly Pro Gly Leu Val Ala
            20              25              30

Pro Ser Glu Ser Leu Ser Ile Thr Cys Thr Val Ser Gly Phe Ser Leu
        35              40              45

Ile Asp Tyr Gly Val Asn Trp Ile Arg Gln Pro Pro Gly Lys Gly Leu
```

-continued

```
        50              55              60

Glu Trp Leu Gly Val Ile Trp Gly Asp Gly Thr Thr Tyr Tyr Asn Pro
65              70              75              80

Ser Leu Lys Ser Arg Leu Ser Ile Ser Lys Asp Asn Ser Lys Ser Gln
                85              90              95

Val Phe Leu Lys Met Asn Ser Leu Thr Ala Ala Asp Thr Ala Met Tyr
                100             105             110

Tyr Cys Ala Arg Ile Val Tyr Trp Gly Gln Gly Thr Leu Val Thr Val
        115             120             125

Ser Ser Ala Ser Thr Lys Gly Pro Ser Val Phe Pro Leu Ala Pro Cys
        130             135             140

Ser Arg Ser Thr Ser Glu Ser Thr Ala Ala Leu Gly Cys Leu Val Lys
145             150             155             160

Asp Tyr Phe Pro Glu Pro Val Thr Val Ser Trp Asn Ser Gly Ala Leu
                165             170             175

Thr Ser Gly Val His Thr Phe Pro Ala Val Leu Gln Ser Ser Gly Leu
                180             185             190

Tyr Ser Leu Ser Ser Val Val Thr Val Pro Ser Ser Ser Leu Gly Thr
                195             200             205

Lys Thr Tyr Thr Cys Asn Val Asp His Lys Pro Ser Asn Thr Lys Val
        210             215             220

Asp Lys Arg Val Glu Ser Lys Tyr Gly Pro Pro Cys Pro Ser Cys Pro
225             230             235             240

Ala Pro Glu Phe Leu Gly Gly Pro Ser Val Phe Leu Phe Pro Pro Lys
                245             250             255

Pro Lys Asp Thr Leu Met Ile Ser Arg Thr Pro Glu Val Thr Cys Val
                260             265             270

Val Val Asp Val Ser Gln Glu Asp Pro Glu Val Gln Phe Asn Trp Tyr
                275             280             285

Val Asp Gly Val Glu Val His Asn Ala Lys Thr Lys Pro Arg Glu Glu
        290             295             300

Gln Phe Asn Ser Thr Tyr Arg Val Val Ser Val Leu Thr Val Leu His
305             310             315             320

Gln Asp Trp Leu Asn Gly Lys Glu Tyr Lys Cys Lys Val Ser Asn Lys
                325             330             335

Gly Leu Pro Ser Ser Ile Glu Lys Thr Ile Ser Lys Ala Lys Gly Gln
                340             345             350

Pro Arg Glu Pro Gln Val Tyr Thr Leu Pro Pro Ser Gln Glu Glu Met
        355             360             365

Thr Lys Asn Gln Val Ser Leu Thr Cys Leu Val Lys Gly Phe Tyr Pro
        370             375             380

Ser Asp Ile Ala Val Glu Trp Glu Ser Asn Gly Gln Pro Glu Asn Asn
385             390             395             400

Tyr Lys Thr Thr Pro Pro Val Leu Asp Ser Asp Gly Ser Phe Phe Leu
                405             410             415

Tyr Ser Arg Leu Thr Val Asp Lys Ser Arg Trp Gln Glu Gly Asn Val
                420             425             430

Phe Ser Cys Ser Val Met His Glu Ala Leu His Asn His Tyr Thr Gln
        435             440             445

Lys Ser Leu Ser Leu Ser Leu Gly
450             455
```

<210> SEQ ID NO 24

-continued

```
<211> LENGTH: 1385
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
gctagcacca tgggctggag ctgcatcatc ctgttcctgg tggccaccgc caccggcgtg      60
cacagccagg tgcagctgca ggagagcggc cccggcctgg tggcccccag cgagagcctg     120
agcatcacct gcaccgtgag cggcttcagc ctgatcgact acggcgtgaa ctggatccgc     180 cagcccccg gcaagggcct ggagtggctg ggcgtgatct ggggcgacgg caccacctac     240
tacaacccca gcctgaagag ccgcctgagc atctccaagg acaacagcaa gagccaggtg     300
ttcctgaaga tgaacagcct gaccgccgcc gacaccgcca tgtactactg cgcccgcatc     360
gtgtactggg gccagggcac cctggtgacc gtgagcagcg ccagcaccaa gggcccttcc     420
gtgttccctc tggccccttg ctcccggtcc acctccgagt ccaccgccgc tctgggctgc     480
ctggtgaagg actacttccc tgagcctgtg accgtgtcct ggaactctgg cgccctgacc     540
tccggcgtgc acaccttccc tgccgtgctg cagtcctccg gcctgtactc cctgtcctcc     600
gtggtgaccg tgccttcctc ctccctgggc accaagacct acacctgtaa cgtggaccac     660
aagccttcca acaccaaggt ggacaagcgg gtggagtcca agtacggccc tccttgccct     720
tcctgccctg cccctgagtt cctgggcgga cctagcgtgt tcctgttccc tcctaagcct     780
aaggacaccc tgatgatctc ccggacccct gaggtgacct gtgtggtggt ggacgtgtcc     840
caggaggacc ctgaggtcca gttcaactgg tacgtggacg gcgtggaggt gcacaacgcc     900
aagaccaagc ctcgggagga gcagttcaat tccacctacc gggtggtgtc tgtgctgacc     960
gtgctgcacc aggactggct gaacggcaaa gaatacaagt gtaaggtctc caacaagggc    1020 ctgcccctcct ccatcgagaa aaccatctcc aaggccaagg ccagcctag ggagcctcag    1080 gtgtacaccc tgcctcctag ccaggaagag atgaccaaga ccaggtgtc cctgacctgt    1140 ctggtgaagg gcttctaccc ttccgacatc gccgtggagt gggagtccaa cggccagcct    1200
gagaacaact acaagaccac ccctcctgtg ctggactccg acggctcctt cttcctgtac    1260
tccaggctga ccgtggacaa gtcccggtgg caggagggca acgtcttttc ctgctccgtg    1320
atgcacgagg ccctgcacaa ccactacacc cagaagtccc tgtccctgtc tctgggctga    1380
agctt                                                                1385

<210> SEQ ID NO 25
<211> LENGTH: 22
<212> TYPE: PRT
<213> ORGANISM: Homo sapiens

<400> SEQUENCE: 25

Lys Pro Gly Gln Pro Pro Arg Leu Leu Ile Tyr Asp Ala Ser Asn Arg
1               5                   10                  15

Ala Thr Gly Ile Pro Ala
            20

<210> SEQ ID NO 26
<211> LENGTH: 12
<212> TYPE: PRT
<213> ORGANISM: Mus musculus

<400> SEQUENCE: 26
```

```
Thr Asp Asp Thr Ala Met Tyr Tyr Cys Ala Arg Ile
1               5                   10

<210> SEQ ID NO 27
<211> LENGTH: 12
<212> TYPE: PRT
<213> ORGANISM: Homo sapiens

<400> SEQUENCE: 27

Ser Glu Asp Ser Ala Leu Tyr Tyr Cys Ala Arg Asp
1               5                   10

<210> SEQ ID NO 28
<211> LENGTH: 112
<212> TYPE: PRT
<213> ORGANISM: Mus musculus

<400> SEQUENCE: 28

Asp Ile Val Met Thr Gln Ala Ala Pro Ser Val Ala Val Thr Pro Arg
1               5                   10                  15

Glu Ser Val Ser Ile Ser Cys Arg Ser Ser Lys Ser Leu Leu His Ser
            20                  25                  30

Ser Gly Lys Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65              70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Leu Glu Ile Lys
            100                 105                 110

<210> SEQ ID NO 29
<211> LENGTH: 111
<212> TYPE: PRT
<213> ORGANISM: Mus musculus

<400> SEQUENCE: 29

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ile Asp Tyr
            20                  25                  30

Gly Val Asn Trp Ile Arg Gln Pro Pro Gly Lys Gly Leu Glu Trp Leu
        35                  40                  45

Gly Val Ile Trp Gly Asp Gly Thr Thr Tyr Tyr Asn Ser Ala Leu Lys
    50                  55                  60

Ser Arg Leu Ser Ile Arg Lys Asp Asn Ser Gln Ser Gln Val Phe Leu
65              70                  75                  80

Lys Met Asn Ser Leu Gln Thr Asp Asp Thr Ala Met Tyr Tyr Cys Ala
                85                  90                  95

Arg Ile Val Tyr Trp Gly Gln Gly Thr Leu Val Thr Val Ser Ala
            100                 105                 110

<210> SEQ ID NO 30
<211> LENGTH: 112
<212> TYPE: PRT
<213> ORGANISM: Artificial Sequence
<220> FEATURE:
<223> OTHER INFORMATION: Description of Artificial Sequence: Synthetic
```

-continued

```
      polypeptide

<400> SEQUENCE: 30

Asp Ile Val Met Thr Gln Ala Ala Pro Ser Val Ala Val Thr Pro Gly
1               5                   10                  15

Ala Ser Val Ser Ile Ser Cys Arg Ser Ser Lys Ser Leu Leu His Ser
            20                  25                  30

Ser Gly Lys Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Leu Glu Ile Lys
            100                 105                 110

<210> SEQ ID NO 31
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Asp Ile Val Met Thr Gln Ala Ala Pro Ser Val Ala Val Thr Pro Gly
1               5                   10                  15

Ala Ser Val Ser Ile Ser Cys Arg Ser Ser Lys Ser Leu Leu His Ser
            20                  25                  30

Ser Gly Lys Thr Tyr Leu Tyr Trp Phe Leu Gln Arg Pro Gly Gln Ser
        35                  40                  45

Pro Gln Leu Leu Ile Tyr Arg Leu Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Leu Glu Ile Lys
            100                 105                 110

<210> SEQ ID NO 32
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Ile Val Met Thr Gln Ala Ala Pro Ser Val Ala Val Thr Pro Gly
1               5                   10                  15

Ala Ser Val Ser Ile Ser Cys Arg Ser Ser Lys Ser Leu Leu His Ser
            20                  25                  30

Ser Gly Lys Thr Tyr Leu Tyr Trp Phe Leu Gln Arg Pro Gly Gln Ser
        35                  40                  45

Pro Gln Leu Leu Ile Tyr Arg Leu Ser Ser Leu Ala Ser Gly Val Pro
    50                  55                  60
```

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Leu Glu Ile Lys
            100                 105                 110

<210> SEQ ID NO 33
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Val Gln Leu Lys Glu Ser Gly Pro Gly Leu Val Ala Pro Ser Glu
1               5                   10                  15

Ser Leu Ser Ile Thr Cys Thr Val Ser Gly Phe Ser Leu Ile Asp Tyr
                20                  25                  30

Gly Val Asn Trp Ile Arg Gln Pro Pro Gly Lys Gly Leu Glu Trp Leu
            35                  40                  45

Gly Val Ile Trp Gly Asp Gly Thr Thr Tyr Tyr Asn Pro Ser Leu Lys
        50                  55                  60

Ser Arg Leu Ser Ile Ser Lys Asp Asn Ser Lys Ser Gln Val Phe Leu
65                  70                  75                  80

Lys Val Thr Ser Leu Thr Thr Asp Asp Thr Ala Met Tyr Tyr Cys Ala
                85                  90                  95

Arg Ile Val Tyr Trp Gly Gln Gly Thr Leu Val Thr Val Ser Ala
            100                 105                 110

<210> SEQ ID NO 34
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Glu Val Gln Leu Lys Glu Ser Gly Pro Gly Leu Val Ala Pro Gly Gly
1               5                   10                  15

Ser Leu Ser Ile Thr Cys Thr Val Ser Gly Phe Ser Leu Ile Asp Tyr
                20                  25                  30

Gly Val Asn Trp Ile Arg Gln Pro Pro Gly Lys Gly Leu Glu Trp Leu
            35                  40                  45

Gly Val Ile Trp Gly Asp Gly Thr Thr Tyr Tyr Asn Ala Pro Leu Lys
        50                  55                  60

Gly Arg Leu Ser Ile Ser Lys Asp Asn Ser Lys Ser Gln Val Phe Leu
65                  70                  75                  80

Gln Met Asn Ser Leu Lys Thr Asp Asp Thr Ala Met Tyr Tyr Cys Ala
                85                  90                  95

Arg Ile Val Tyr Trp Gly Gln Gly Thr Leu Val Thr Val Ser Ser
            100                 105                 110

<210> SEQ ID NO 35
<211> LENGTH: 238
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 35

Met Gly Trp Ser Cys Ile Ile Leu Phe Leu Val Ala Thr Ala Thr Gly
1               5                   10                  15

Val His Ser Asp Ile Val Met Thr Gln Ala Ala Pro Ser Val Ala Val
            20                  25                  30

Thr Pro Arg Glu Ser Val Ser Ile Ser Cys Arg Ser Ser Lys Ser Leu
        35                  40                  45

Leu His Ser Ser Gly Lys Thr Tyr Leu Tyr Trp Phe Leu Gln Arg Pro
    50                  55                  60

Gly Gln Ser Pro Gln Leu Leu Ile Tyr Arg Met Ser Asn Leu Ala Ser
65                  70                  75                  80

Gly Val Pro Asp Arg Phe Ser Gly Ser Gly Ser Gly Thr Ala Phe Thr
                85                  90                  95

Leu Arg Ile Ser Arg Val Glu Ala Glu Asp Val Gly Val Tyr Tyr Cys
            100                 105                 110

Met Gln His Leu Glu Tyr Pro Tyr Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 36
<211> LENGTH: 731
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 36
gctagcacca tgggctggag ctgcatcatc ctgttcctgg tggccaccgc caccggcgtg      60
cacagcgaca tcgtgatgac ccaggccgcc cccagcgtgg ccgtgacccc cgcgagagc      120 gtgagcatca gctgccgcag cagcaagagc ctgctgcaca gcagcggcaa gacctacctg      180
tactggttcc tgcagcgccc cggccagagc ccccagctgc tgatctaccg catgagcaac      240
ctggccagcg gcgtgcccga ccgcttcagc ggcagcggca gcggcaccgc cttcaccctg      300
cgcatcagcc gcgtggaggc cgaggacgtg ggcgtgtact actgcatgca gcacctggag      360 taccccctaca ccttcggcgg cggcaccaag ctggagatca gcgtacggt ggccgctcct      420 tccgtgttca tcttccctcc ctccgacgag cagctgaagt ccggcaccgc ctccgtggtg      480
tgtctgctga acaacttcta ccctcgggag gccaaggtgc agtggaaggt ggacaacgcc      540

```
ctgcagtccg gcaactccca ggagtccgtc accgagcagg actccaagga cagcacctac        600
tccctgtcct ccaccctgac cctgtccaag gccgactacg agaagcacaa ggtgtacgcc        660
tgtgaggtga cccaccaggg cctgtccagc cctgtgacca agtccttcaa ccggggcgag        720
tgctgaagct t                                                            731
```

```
<210> SEQ ID NO 37
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Met Gly Trp Ser Cys Ile Ile Leu Phe Leu Val Ala Thr Ala Thr Gly
1               5                   10                  15

Val His Ser Gln Val Gln Leu Lys Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Ile Asp Tyr Gly Val Asn Trp Ile Arg Gln Pro Pro Gly Lys Gly Leu
    50                  55                  60

Glu Trp Leu Gly Val Ile Trp Gly Asp Gly Thr Thr Tyr Tyr Asn Ser
65                  70                  75                  80

Ala Leu Lys Ser Arg Leu Ser Ile Arg Lys Asp Asn Ser Gln Ser Gln
                85                  90                  95

Val Phe Leu Lys Met Asn Ser Leu Gln Thr Asp Asp Thr Ala Met Tyr
            100                 105                 110

Tyr Cys Ala Arg Ile Val Tyr Trp Gly Gln Gly Thr Leu Val Thr Val
            115                 120                 125

Ser Ala Ala Ser Thr Lys Gly Pro Ser Val Phe Pro Leu Ala Pro Cys
    130                 135                 140

Ser Arg Ser Thr Ser Glu Ser Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
            195                 200                 205

Lys Thr Tyr Thr Cys Asn Val Asp His Lys Pro Ser Asn Thr Lys Val
    210                 215                 220

Asp Lys Arg Val Glu Ser Lys Tyr Gly Pro Pro Cys Pro Ser Cys Pro
225                 230                 235                 240

Ala Pro Glu Phe Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser Gln Glu Asp Pro Glu Val Gln Phe Asn Trp Tyr
            275                 280                 285

Val Asp Gly Val Glu Val His Asn Ala Lys Thr Lys Pro Arg Glu Glu
    290                 295                 300

Gln Phe Asn Ser Thr Tyr Arg Val Val Ser Val Leu Thr Val Leu His
305                 310                 315                 320
```

-continued

Gln Asp Trp Leu Asn Gly Lys Glu Tyr Lys Cys Lys Val Ser Asn Lys
              325                     330                     335

Gly Leu Pro Ser Ser Ile Glu Lys Thr Ile Ser Lys Ala Lys Gly Gln
              340                     345                     350

Pro Arg Glu Pro Gln Val Tyr Thr Leu Pro Pro Ser Gln Glu Glu Met
              355                     360                     365

Thr Lys Asn Gln Val Ser Leu Thr Cys Leu Val Lys Gly Phe Tyr Pro
              370                     375                     380

Ser Asp Ile Ala Val Glu Trp Glu Ser Asn Gly Gln Pro Glu Asn Asn
385                     390                     395                     400

Tyr Lys Thr Thr Pro Pro Val Leu Asp Ser Asp Gly Ser Phe Phe Leu
              405                     410                     415

Tyr Ser Arg Leu Thr Val Asp Lys Ser Arg Trp Gln Glu Gly Asn Val
              420                     425                     430

Phe Ser Cys Ser Val Met His Glu Ala Leu His Asn His Tyr Thr Gln
              435                     440                     445

Lys Ser Leu Ser Leu Ser Leu Gly
       450                     455

<210> SEQ ID NO 38
<211> LENGTH: 1385
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
gctagcacca tgggctggag ctgcatcatc ctgttcctgg tggccaccgc caccggcgtg      60
cacagccagg tgcagctgaa ggagagcggc cccggcctgg tggcccccag ccagagcctg     120
agcatcacct gcaccgtgag cggcttcagc ctgatcgact acggcgtgaa ctggatccgc     180 cagcccccg gcaagggcct ggagtggctg ggcgtgatct ggggcgacgg caccacctac     240
tacaacagcg ccctgaagag ccgcctgagc atccgcaagg acaacagcca gagccaggtg     300
ttcctgaaga tgaacagcct gcagaccgac gacaccgcca tgtactactg cgcccgcatc     360
gtgtactggg gccagggcac cctggtgacc gtgagcgccg ccagcaccaa gggcccttcc     420
gtgttccctc tggccccttg ctcccggtcc acctccgagt ccaccgccgc tctgggctgc     480
ctggtgaagg actacttccc tgagcctgtg accgtgtcct ggaactctgg cgccctgacc     540
tccggcgtgc acaccttccc tgccgtgctg cagtcctccg gcctgtactc cctgtcctcc     600
gtggtgaccg tgccttcctc ctccctgggc accaagacct acacctgtaa cgtggaccac     660
aagccttcca acaccaaggt ggacaagcgg gtggagtcca gtacggccc tccttgccct     720 tcctgccctg ccctgagtt cctgggcgga cctagcgtgt tcctgttccc tcctaagcct     780
aaggacaccc tgatgatctc ccggacccct gaggtgacct gtgtggtggt ggacgtgtcc     840
caggaggacc ctgaggtcca gttcaactgg tacgtggacg gcgtggaggt gcacaacgcc     900
aagaccaagc ctcgggagga gcagttcaat tccacctacc gggtggtgtc tgtgctgacc     960
gtgctgcacc aggactggct gaacggcaaa gaatacaagt gtaaggtctc caacaagggc    1020 ctgcctcct ccatcgagaa aaccatctcc aaggccaagg ccagcctag ggagcctcag    1080 gtgtacaccc tgcctcctag ccaggaagag atgaccaaga accaggtgtc cctgacctgt    1140
ctggtgaagg gcttctaccc ttccgacatc gccgtggagt gggagtccaa cggccagcct    1200

-continued

```
gagaacaact acaagaccac ccctcctgtg ctggactccg acggctcctt cttcctgtac    1260
tccaggctga ccgtggacaa gtcccggtgg caggagggca acgtcttttc ctgctccgtg    1320
atgcacgagg ccctgcacaa ccactacacc cagaagtccc tgtccctgtc tctgggctga    1380
agctt                                                                 1385
```

```
<210> SEQ ID NO 39
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Met Gly Trp Ser Cys Ile Ile Leu Phe Leu Val Ala Thr Ala Thr Gly
1               5                   10                  15

Val His Ser Asp Ile Val Met Thr Gln Ala Ala Pro Ser Val Ala Val
                20                  25                  30

Thr Pro Gly Ala Ser Val Ser Ile Ser Cys Arg Ser Ser Lys Ser Leu
            35                  40                  45

Leu His Ser Ser Gly Lys Thr Tyr Leu Tyr Trp Phe Leu Gln Arg Pro
        50                  55                  60

Gly Gln Ser Pro Gln Leu Leu Ile Tyr Arg Met Ser Asn Leu Ala Ser
65                  70                  75                  80

Gly Val Pro Asp Arg Phe Ser Gly Ser Gly Ser Gly Thr Ala Phe Thr
                85                  90                  95

Leu Arg Ile Ser Arg Val Glu Ala Glu Asp Val Gly Val Tyr Tyr Cys
                100                 105                 110

Met Gln His Leu Glu Tyr Pro Tyr Thr Phe Gly Gly Gly Thr Lys Leu
            115                 120                 125

Glu Ile Lys Arg Thr Val Ala Ala Pro Ser Val Phe Ile Phe Pro Pro
        130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
            195                 200                 205

Asp Tyr Glu Lys His Lys Val Tyr Ala Cys Glu Val Thr His Gln Gly
        210                 215                 220

Leu Ser Ser Pro Val Thr Lys Ser Phe Asn Arg Gly Glu Cys
225                 230                 235
```

```
<210> SEQ ID NO 40
<211> LENGTH: 731
<212> TYPE: DNA
<213> ORGANISM: Artificial Sequence
<220> FEATURE:
<223> OTHER INFORMATION: Description of Artificial Sequence: Synthetic
      polypeptide

<400> SEQUENCE: 40
gctagcacca tgggctggag ctgcatcatc ctgttcctgg tggccaccgc caccggcgtg    60
cacagcgaca tcgtgatgac ccaggccgcc cccagcgtgg ccgtgacccc cggcgccagc   120
```

-continued

```
gtgagcatca gctgccgcag cagcaagagc ctgctgcaca gcagcggcaa gacctacctg      180
tactggttcc tgcagcgccc cggccagagc ccccagctgc tgatctaccg catgagcaac      240
ctggccagcg gcgtgcccga ccgcttcagc ggcagcggca gcggcaccgc cttcaccctg      300
cgcatcagcc gcgtggaggc cgaggacgtg ggcgtgtact actgcatgca gcacctggag      360 taccectaca ccttcggcgg cggcaccaag ctggagatca gcgtacggt ggccgctcct      420 tccgtgttca tcttccctcc ctccgacgag cagctgaagt ccggcaccgc ctccgtggtg      480
tgtctgctga acaacttcta ccctcgggag gccaaggtgc agtggaaggt ggacaacgcc      540
ctgcagtccg gcaactccca ggagtccgtc accgagcagg actccaagga cagcacctac      600
tccctgtcct ccaccctgac cctgtccaag gccgactacg agaagcacaa ggtgtacgcc      660
tgtgaggtga cccaccaggg cctgtccagc cctgtgacca gtccttcaa ccggggcgag      720 tgctgaagct t                                                            731
```

```
<210> SEQ ID NO 41
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Gly Trp Ser Cys Ile Ile Leu Phe Leu Val Ala Thr Ala Thr Gly
1               5                   10                  15

Val His Ser Asp Ile Val Met Thr Gln Ala Ala Pro Ser Val Ala Val
                20                  25                  30

Thr Pro Gly Ala Ser Val Ser Ile Ser Cys Arg Ser Ser Lys Ser Leu
            35                  40                  45

Leu His Ser Ser Gly Lys Thr Tyr Leu Tyr Trp Phe Leu Gln Arg Pro
        50                  55                  60

Gly Gln Ser Pro Gln Leu Leu Ile Tyr Arg Leu Ser Asn Leu Ala Ser
65                  70                  75                  80

Gly Val Pro Asp Arg Phe Ser Gly Ser Gly Ser Gly Thr Ala Phe Thr
                85                  90                  95

Leu Arg Ile Ser Arg Val Glu Ala Glu Asp Val Gly Val Tyr Tyr Cys
            100                 105                 110

Met Gln His Leu Glu Tyr Pro Tyr Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

-continued

```
<210> SEQ ID NO 42
<211> LENGTH: 731
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
gctagcacca tgggctggag ctgcatcatc ctgttcctgg tggccaccgc caccggcgtg     60
cacagcgaca tcgtgatgac ccaggccgcc cccagcgtgg ccgtgacccc cggcgccagc    120
gtgagcatca gctgccgcag cagcaagagc ctgctgcaca gcagcggcaa gacctacctg    180
tactggttcc tgcagcgccc cggccagagc ccccagctgc tgatctaccg cctgagcaac    240
ctggccagcg gcgtgcccga ccgcttcagc ggcagcggca gcggcaccgc cttcaccctg    300
cgcatcagcc gcgtggaggc cgaggacgtg ggcgtgtact actgcatgca gcacctggag    360
tacccctaca ccttcggcgg cggcaccaag ctggagatca gcgtacggt ggccgctcct     420 tccgtgttca tcttccctcc ctccgacgag cagctgaagt ccggcaccgc ctccgtggtg    480
tgtctgctga caacttcta ccctcgggag gccaaggtgc agtggaaggt ggacaacgcc     540
ctgcagtccg gcaactccca ggagtccgtc accgagcagg actccaagga cagcacctac    600
tccctgtcct ccaccctgac cctgtccaag gccgactacg agaagcacaa ggtgtacgcc    660
tgtgaggtga cccaccaggg cctgtccagc cctgtgacca gtccttcaa ccggggcgag     720 tgctgaagct t                                                         731

<210> SEQ ID NO 43
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Met Gly Trp Ser Cys Ile Ile Leu Phe Leu Val Ala Thr Ala Thr Gly
1               5                   10                  15

Val His Ser Asp Ile Val Met Thr Gln Ala Ala Pro Ser Val Ala Val
            20                  25                  30

Thr Pro Gly Ala Ser Val Ser Ile Ser Cys Arg Ser Ser Lys Ser Leu
        35                  40                  45

Leu His Ser Ser Gly Lys Thr Tyr Leu Tyr Trp Phe Leu Gln Arg Pro
    50                  55                  60

Gly Gln Ser Pro Gln Leu Leu Ile Tyr Arg Leu Ser Ser Leu Ala Ser
65                  70                  75                  80

Gly Val Pro Asp Arg Phe Ser Gly Ser Gly Ser Gly Thr Ala Phe Thr
                85                  90                  95

Leu Arg Ile Ser Arg Val Glu Ala Glu Asp Val Gly Val Tyr Tyr Cys
            100                 105                 110

Met Gln His Leu Glu Tyr Pro Tyr Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175
```

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 44
<211> LENGTH: 731
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
gctagcacca tgggctggag ctgcatcatc ctgttcctgg tggccaccgc caccggcgtg        60
cacagcgaca tcgtgatgac ccaggccgcc cccagcgtgg ccgtgacccc cggcgccagc       120
gtgagcatca gctgccgcag cagcaagagc ctgctgcaca gcagcggcaa gacctacctg       180
tactggttcc tgcagcgccc cggccagagc ccccagctgc tgatctaccg cctgagcagc       240
ctggccagcg gcgtgcccga ccgcttcagc ggcagcggca gcggcaccgc cttcaccctg       300
cgcatcagcc gcgtggaggc cgaggacgtg ggcgtgtact actgcatgca gcacctggag       360
tacccctaca ccttcggcgg cggcaccaag ctggagatca gcgtacggt ggccgctcct        420 tccgtgttca tcttccctcc ctccgacgag cagctgaagt ccggcaccgc ctccgtggtg       480
tgtctgctga caacttcta ccctcgggag gccaaggtgc agtggaaggt ggacaacgcc        540
ctgcagtccg gcaactccca ggagtccgtc accgagcagg actccaagga cagcacctac       600
tccctgtcct ccaccctgac cctgtccaag gccgactacg agaagcacaa ggtgtacgcc       660
tgtgaggtga cccaccaggg cctgtccagc cctgtgacca agtccttcaa ccggggcgag       720
tgctgaagct t                                                             731

<210> SEQ ID NO 45
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Gly Trp Ser Cys Ile Ile Leu Phe Leu Val Ala Thr Ala Thr Gly
1               5                   10                  15

Val His Ser Gln Val Gln Leu Lys Glu Ser Gly Pro Gly Leu Val Ala
            20                  25                  30

Pro Ser Glu Ser Leu Ser Ile Thr Cys Thr Val Ser Gly Phe Ser Leu
        35                  40                  45

Ile Asp Tyr Gly Val Asn Trp Ile Arg Gln Pro Pro Gly Lys Gly Leu
    50                  55                  60

Glu Trp Leu Gly Val Ile Trp Gly Asp Gly Thr Thr Tyr Tyr Asn Pro
65                  70                  75                  80

Ser Leu Lys Ser Arg Leu Ser Ile Ser Lys Asp Asn Ser Lys Ser Gln
            85                  90                  95

-continued

Val Phe Leu Lys Val Thr Ser Leu Thr Thr Asp Asp Thr Ala Met Tyr
            100                 105                 110

Tyr Cys Ala Arg Ile Val Tyr Trp Gly Gln Gly Thr Leu Val Thr Val
            115                 120                 125

Ser Ala Ala Ser Thr Lys Gly Pro Ser Val Phe Pro Leu Ala Pro Cys
            130                 135                 140

Ser Arg Ser Thr Ser Glu Ser Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
            195                 200                 205

Lys Thr Tyr Thr Cys Asn Val Asp His Lys Pro Ser Asn Thr Lys Val
            210                 215                 220

Asp Lys Arg Val Glu Ser Lys Tyr Gly Pro Pro Cys Pro Ser Cys Pro
225                 230                 235                 240

Ala Pro Glu Phe Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser Gln Glu Asp Pro Glu Val Gln Phe Asn Trp Tyr
            275                 280                 285

Val Asp Gly Val Glu Val His Asn Ala Lys Thr Lys Pro Arg Glu Glu
            290                 295                 300

Gln Phe Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Gly Leu Pro Ser Ser Ile Glu Lys Thr Ile Ser Lys Ala Lys Gly Gln
            340                 345                 350

Pro Arg Glu Pro Gln Val Tyr Thr Leu Pro Pro Ser Gln Glu Glu Met
            355                 360                 365

Thr Lys Asn Gln Val Ser Leu Thr Cys Leu Val Lys Gly Phe Tyr Pro
            370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Arg Leu Thr Val Asp Lys Ser Arg Trp Gln Glu Gly Asn Val
            420                 425                 430

Phe Ser Cys Ser Val Met His Glu Ala Leu His Asn His Tyr Thr Gln
            435                 440                 445

Lys Ser Leu Ser Leu Ser Leu Gly
    450                 455

<210> SEQ ID NO 46
<211> LENGTH: 1385
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46

-continued

```
gctagcacca tgggctggag ctgcatcatc ctgttcctgg tggccaccgc caccggcgtg      60
cacagccagg tgcagctgaa ggagagcggc cccggcctgg tggcccccag cgagagcctg     120
agcatcacct gcaccgtgag cggcttcagc ctgatcgact acggcgtgaa ctggatccgc     180 cagcccccccg gcaagggcct ggagtggctg ggcgtgatct ggggcgacgg caccacctac     240 tacaaccccca gcctgaagag ccgcctgagc atcagcaagg acaacagcaa gagccaggtg     300
ttcctgaagg tgaccagcct gaccaccgac gacaccgcca tgtactactg cgcccgcatc     360
gtgtactggg gccagggcac cctggtgacc gtgagcgccg ccagcaccaa gggcccttcc     420
gtgttccctc tggcccccttg ctcccggtcc acctccgagt ccaccgccgc tctgggctgc     480
ctggtgaagg actacttccc tgagcctgtg accgtgtcct ggaactctgg cgccctgacc     540
tccggcgtgc acaccttccc tgccgtgctg cagtcctccg gcctgtactc cctgtcctcc     600
gtggtgaccg tgccttcctc ctccctgggc accaagacct acacctgtaa cgtggaccac     660
aagccttcca acaccaaggt ggacaagcgg gtggagtcca agtacggccc tccttgccct     720
tcctgccctg cccctgagtt cctgggcgga cctagcgtgt tcctgttccc tcctaagcct     780
aaggacaccc tgatgatctc ccggacccct gaggtgacct gtgtggtggt ggacgtgtcc     840
caggaggacc ctgaggtcca gttcaactgg tacgtggacg gcgtggaggt gcacaacgcc     900
aagaccaagc ctcgggagga gcagttcaat tccacctacc gggtggtgtc tgtgctgacc     960
gtgctgcacc aggactggct gaacggcaaa gaatacaagt gtaaggtctc caacaagggc    1020 ctgcccctcct ccatcgagaa aaccatctcc aaggccaagg ccagcctag ggagcctcag    1080 gtgtacaccc tgcctcctag ccaggaagag atgaccaaga accaggtgtc cctgacctgt    1140
ctggtgaagg gcttctaccc ttccgacatc gccgtggagt gggagtccaa cggccagcct    1200
gagaacaact acaagaccac ccctcctgtg ctggactccg acggctcctt cttcctgtac    1260
tccaggctga ccgtggacaa gtcccggtgg caggagggca acgtctttttc ctgctccgtg    1320 atgcacgagg ccctgcacaa ccactacacc cagaagtccc tgtccctgtc tctgggctga    1380
agctt                                                                 1385
```

<210> SEQ ID NO 47
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

```
Met Gly Trp Ser Cys Ile Ile Leu Phe Leu Val Ala Thr Ala Thr Gly
1               5                   10                  15

Val His Ser Glu Val Gln Leu Lys Glu Ser Gly Pro Gly Leu Val Ala
            20                  25                  30

Pro Gly Gly Ser Leu Ser Ile Thr Cys Thr Val Ser Gly Phe Ser Leu
        35                  40                  45

Ile Asp Tyr Gly Val Asn Trp Ile Arg Gln Pro Pro Gly Lys Gly Leu
    50                  55                  60

Glu Trp Leu Gly Val Ile Trp Gly Asp Gly Thr Thr Tyr Tyr Asn Ala
65                  70                  75                  80

Pro Leu Lys Gly Arg Leu Ser Ile Ser Lys Asp Asn Ser Lys Ser Gln
                85                  90                  95

Val Phe Leu Gln Met Asn Ser Leu Lys Thr Asp Asp Thr Ala Met Tyr
```

-continued

```
                100              105                110

Tyr Cys Ala Arg Ile Val Tyr Trp Gly Gln Gly Thr Leu Val Thr Val
        115                 120                 125

Ser Ser Ala Ser Thr Lys Gly Pro Ser Val Phe Pro Leu Ala Pro Cys
    130                 135                 140

Ser Arg Ser Thr Ser Glu Ser Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
                180                 185                 190

Tyr Ser Leu Ser Ser Val Val Thr Val Pro Ser Ser Ser Leu Gly Thr
        195                 200                 205

Lys Thr Tyr Thr Cys Asn Val Asp His Lys Pro Ser Asn Thr Lys Val
    210                 215                 220

Asp Lys Arg Val Glu Ser Lys Tyr Gly Pro Pro Cys Pro Ser Cys Pro
225                 230                 235                 240

Ala Pro Glu Phe Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
                260                 265                 270

Val Val Asp Val Ser Gln Glu Asp Pro Glu Val Gln Phe Asn Trp Tyr
                275                 280                 285

Val Asp Gly Val Glu Val His Asn Ala Lys Thr Lys Pro Arg Glu Glu
        290                 295                 300

Gln Phe Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Gly Leu Pro Ser Ser Ile Glu Lys Thr Ile Ser Lys Ala Lys Gly Gln
                340                 345                 350

Pro Arg Glu Pro Gln Val Tyr Thr Leu Pro Pro Ser Gln Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Arg Leu Thr Val Asp Lys Ser Arg Trp Gln Glu Gly Asn Val
                420                 425                 430

Phe Ser Cys Ser Val Met His Glu Ala Leu His Asn His Tyr Thr Gln
        435                 440                 445

Lys Ser Leu Ser Leu Ser Leu Gly
    450                 455
```

```
<210> SEQ ID NO 48
<211> LENGTH: 1385
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
```

-continued

```
gctagcacca tgggctggag ctgcatcatc ctgttcctgg tggccaccgc caccggcgtg       60
cacagcgagg tgcagctgaa ggagagcggc cccggcctgg tggcccccgg cggcagcctg      120
agcatcacct gcaccgtgag cggcttcagc ctgatcgact acggcgtgaa ctggatccgc      180
cagccccccg gcaagggcct ggagtggctg ggcgtgatct ggggcgacgg caccaccctac     240 tacaacgccc ccctgaaggg ccgcctgagc atcagcaagg acaacagcaa gagccaggtg      300
ttcctgcaga tgaacagcct gaagaccgac gacaccgcca tgtactactg cgcccgcatc      360
gtgtactggg gccagggcac cctggtgacc gtgagcagcg ccagcaccaa gggcccttcc      420
gtgttccctc tggcccccttg ctccgcggtcc acctccgagt ccaccgccgc tctgggctgc     480
ctggtgaagg actacttccc tgagcctgtg accgtgtcct ggaactctgg cgccctgacc      540
tccggcgtgc acaccttccc tgccgtgctg cagtcctccg gcctgtactc cctgtcctcc      600
gtggtgaccg tgccttcctc ctccctgggc accaagacct acacctgtaa cgtggaccac      660
aagccttcca acaccaaggt ggacaagcgg gtggagtcca agtacggccc tccttgccct      720
tcctgccctg cccctgagtt cctgggcgga cctagcgtgt tcctgttccc tcctaagcct      780
aaggacaccc tgatgatctc ccggacccct gaggtgacct gtgtggtggt ggacgtgtcc      840
caggaggacc ctgaggtcca gttcaactgg tacgtggacg gcgtggaggt gcacaacgcc      900
aagaccaagc ctcgggagga gcagttcaat tccacctacc gggtggtgtc tgtgctgacc      960
gtgctgcacc aggactggct gaacggcaaa gaatacaagt gtaaggtctc caacaagggc     1020 ctgcccctcct ccatcgagaa aaccatctcc aaggccaagg ccagcctag ggagcctcag     1080 gtgtacaccc tgcctcctag ccaggaagag atgaccaaga accaggtgtc cctgacctgt     1140
ctggtgaagg gcttctaccc ttccgacatc gccgtggagt gggagtccaa cggccagcct     1200
gagaacaact acaagaccac ccctcctgtg ctggactccg acggctcctt cttcctgtac     1260
tccaggctga ccgtggacaa gtcccggtgg caggagggca acgtcttttc ctgctccgtg     1320
atgcacgagg ccctgcacaa ccactacacc cagaagtccc tgtccctgtc tctgggctga     1380
agctt                                                                  1385

<210> SEQ ID NO 49
<211> LENGTH: 5
<212> TYPE: PRT
<213> ORGANISM: Homo sapiens

<400> SEQUENCE: 49

Glu Leu Leu Gly Gly
1               5

<210> SEQ ID NO 50
<211> LENGTH: 5
<212> TYPE: PRT
<213> ORGANISM: Homo sapiens

<400> SEQUENCE: 50

Met Ile Ser Arg Thr
1               5

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag
```

```
<400> SEQUENCE: 51

His His His His His His
1               5

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Pro Gly Lys Ala Pro Gln Leu Leu Ile Tyr Arg Met Ser Asn Leu
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Pro Gly Lys Ala Pro Lys Leu Leu Ile Tyr Ala Ala Ser Ser Leu
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser Leu Ile Asp Tyr Gly Val Asn Trp Ile Arg Gln Pro Pro Gly
1               5                   10                  15

<210> SEQ ID NO 55
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Asp Ile Val Met Thr Gln Ala Ala Pro Ser Val Ala Val Thr Pro Gly
1               5                   10                  15

Gln Ser Val Ser Ile Ser Cys Arg Ser Ser Lys Ser Leu Leu His Ser
            20                  25                  30

Ser Gly Lys Thr Tyr Leu Tyr Trp Phe Leu Gln His Pro Gly Lys Ala
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Thr Ile
65                  70                  75                  80

Ser Gly Val Gln Ala Glu Asp Val Gly Val Tyr Tyr Cys Met Gln His
                85                  90                  95

Leu Glu Tyr Pro Tyr Thr Phe Gly Gly Gly Thr Lys Leu Glu Ile Lys
            100                 105                 110
```

<210> SEQ ID NO 56
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gln Val Gln Leu Gln Glu Ser Gly Pro Gly Leu Val Ala Pro Ser Gln
1               5                   10                  15

Ser Leu Ser Ile Thr Cys Thr Val Ser Gly Phe Ser Leu Ile Asp Tyr
                20                  25                  30

Gly Val Asn Trp Ile Arg Gln Pro Pro Gly Lys Gly Leu Glu Trp Leu
            35                  40                  45

Gly Val Ile Trp Gly Asp Gly Thr Thr Tyr Tyr Asn Ser Ala Leu Lys
        50                  55                  60

Ser Arg Leu Ser Ile Ser Lys Asp Thr Ser Lys Ser Gln Val Phe Leu
65                  70                  75                  80

Lys Met Asn Ser Leu Thr Thr Asp Asp Thr Ala Met Tyr Tyr Cys Ala
                85                  90                  95

Arg Ile Val Tyr Trp Gly Gln Gly Thr Leu Val Thr Val Ser Ala Ala
            100                 105                 110

Lys

<210> SEQ ID NO 57
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Val Gln Leu Gln Glu Ser Gly Pro Gly Leu Val Ala Pro Ser Gln
1               5                   10                  15

Ser Leu Ser Ile Thr Cys Thr Val Ser Gly Phe Ser Leu Ile Asp Tyr
                20                  25                  30

Gly Val Asn Trp Ile Arg Gln Pro Pro Gly Lys Gly Leu Glu Trp Leu
            35                  40                  45

Gly Val Ile Trp Gly Asp Gly Thr Thr Tyr Tyr Pro Ser Ala Leu Lys
        50                  55                  60

Ser Arg Leu Ser Ile Ser Lys Asp Thr Ser Lys Ser Gln Val Phe Leu
65                  70                  75                  80

Lys Met Asn Ser Leu Thr Thr Asp Asp Thr Ala Met Tyr Tyr Cys Ala
                85                  90                  95

Arg Ile Val Tyr Trp Gly Gln Gly Thr Leu Val Thr Val Ser Ala Ala
            100                 105                 110

Lys

<210> SEQ ID NO 58
<211> LENGTH: 16
<212> TYPE: PRT
<213> ORGANISM: Artificial Sequence
<220> FEATURE:
<223> OTHER INFORMATION: Synthetic peptide

<400> SEQUENCE: 58

Arg Ser Ser Lys Ser Leu Leu His Ser Ser Gly Lys Thr Tyr Leu Tyr

-continued

```
1               5                    10                   15

<210> SEQ ID NO 59
<211> LENGTH: 7
<212> TYPE: PRT
<213> ORGANISM: Artificial Sequence
<220> FEATURE:
<223> OTHER INFORMATION: Synthetic peptide

<400> SEQUENCE: 59

Arg Met Ser Asn Leu Ala Ser
1               5

<210> SEQ ID NO 60
<211> LENGTH: 9
<212> TYPE: PRT
<213> ORGANISM: Artificial Sequence
<220> FEATURE:
<223> OTHER INFORMATION: Synthetic peptide

<400> SEQUENCE: 60

Met Gln His Leu Glu Tyr Pro Tyr Thr
1               5

<210> SEQ ID NO 61
<211> LENGTH: 10
<212> TYPE: PRT
<213> ORGANISM: Artificial Sequence
<220> FEATURE:
<223> OTHER INFORMATION: Synthetic peptide

<400> SEQUENCE: 61

Gly Phe Ser Leu Ile Asp Tyr Gly Val Asn
1               5                    10

<210> SEQ ID NO 62
<211> LENGTH: 9
<212> TYPE: PRT
<213> ORGANISM: Artificial Sequence
<220> FEATURE:
<223> OTHER INFORMATION: Synthetic peptide

<400> SEQUENCE: 62

Val Ile Trp Gly Asp Gly Thr Thr Tyr
1               5

<210> SEQ ID NO 63
<211> LENGTH: 3
<212> TYPE: PRT
<213> ORGANISM: Artificial Sequence
<220> FEATURE:
<223> OTHER INFORMATION: Synthetic peptide

<400> SEQUENCE: 63

Ile Val Tyr
1

<210> SEQ ID NO 64
<211> LENGTH: 7
<212> TYPE: PRT
<213> ORGANISM: Artificial Sequence
<220> FEATURE:
<223> OTHER INFORMATION: Synthetic peptide

<400> SEQUENCE: 64

Arg Leu Ser Asn Leu Ala Ser
1               5
```

-continued

```
<210> SEQ ID NO 65
<211> LENGTH: 8
<212> TYPE: PRT
<213> ORGANISM: Artificial Sequence
<220> FEATURE:
<223> OTHER INFORMATION: Synthetic peptide

<400> SEQUENCE: 65

Arg Leu Ser Ser Asn Leu Ala Ser
1               5

<210> SEQ ID NO 66
<211> LENGTH: 6
<212> TYPE: PRT
<213> ORGANISM: Artificial Sequence
<220> FEATURE:
<223> OTHER INFORMATION: Synthetic peptide

<400> SEQUENCE: 66

Arg Met Ser Asn Leu Ala
1               5

<210> SEQ ID NO 67
<211> LENGTH: 6
<212> TYPE: PRT
<213> ORGANISM: Artificial Sequence
<220> FEATURE:
<223> OTHER INFORMATION: Synthetic peptide

<400> SEQUENCE: 67

Arg Leu Ser Asn Leu Ala
1               5

<210> SEQ ID NO 68
<211> LENGTH: 6
<212> TYPE: PRT
<213> ORGANISM: Artificial Sequence
<220> FEATURE:
<223> OTHER INFORMATION: Synthetic peptide

<400> SEQUENCE: 68

Arg Leu Ser Ser Leu Ala
1               5

<210> SEQ ID NO 69
<211> LENGTH: 17
<212> TYPE: PRT
<213> ORGANISM: Artificial Sequence
<220> FEATURE:
<223> OTHER INFORMATION: Synthetic peptide

<400> SEQUENCE: 69

Arg Ser Ser Lys Ser Leu Leu His Ser Ser Gly Lys Thr Tyr Leu Tyr
1               5                   10                  15

Trp
```